United States Patent
Deadman et al.

(10) Patent No.: US 7,112,572 B2
(45) Date of Patent: Sep. 26, 2006

(54) MULTIVALENT METAL SALTS OF BORONIC ACIDS

(75) Inventors: John Joseph Deadman, Melbourne (AU); David Jonathan Madge, Cambridge (GB); Mark Dolman, Swindon (GB); Sanjay Kumar Kakkar, London (GB); Anthony James Kennedy, London (GB); Sophie Marie Combe-Marzelle, London (GB); Suresh Babubhai Chahwala, London (GB); Oliver Vimpany Arnold Boucher, London (GB)

(73) Assignee: Trigen Limited, London (GB)

( * ) Notice: Subject to any disclaimer, the term of this patent is extended or adjusted under 35 U.S.C. 154(b) by 0 days.

(21) Appl. No.: 10/659,179

(22) Filed: Sep. 9, 2003

(65) Prior Publication Data

US 2004/0147453 A1    Jul. 29, 2004

(30) Foreign Application Priority Data

| Sep. 9, 2002 | (GB) | ................................. 0220764.5 |
| Sep. 9, 2002 | (GB) | ................................. 0220822.1 |
| Apr. 4, 2003 | (GB) | ................................. 0307817.7 |
| May 16, 2003 | (GB) | ................................. 0311237.2 |
| Jul. 4, 2003 | (GB) | ................................. 0315691.6 |

(51) Int. Cl.
C07F 5/02 (2006.01)
A61K 38/04 (2006.01)

(52) U.S. Cl. ............................. 514/19; 514/64; 546/13; 548/405

(58) Field of Classification Search ...................... 514/2
See application file for complete search history.

(56) References Cited

U.S. PATENT DOCUMENTS

| 4,499,082 A | 2/1985 | Shenvi et al. |
| 4,701,545 A | 10/1987 | Matteson et al. |
| 4,935,493 A | 6/1990 | Bachovchin et al. |
| 4,963,655 A | 10/1990 | Kinder et al. |
| 5,169,841 A | 12/1992 | Kleeman et al. |
| 5,187,157 A | 2/1993 | Kettner et al. |
| 5,444,049 A | 8/1995 | de Nanteuil et al. |
| 5,462,964 A | 10/1995 | Fevig et al. |
| 5,563,127 A | 10/1996 | Amparo et al. |
| 5,574,014 A | 11/1996 | Claeson et al. |
| 5,585,360 A | 12/1996 | de Nanteuil et al. |
| 5,639,739 A | 6/1997 | Dominguez et al. |
| 5,658,885 A | 8/1997 | Lee et al. |
| 5,681,978 A | 10/1997 | Matteson et al. |
| 5,731,439 A | 3/1998 | Carini et al. |
| 5,780,454 A | 7/1998 | Adams et al. |
| 5,814,622 A | 9/1998 | de Nanteuil et al. |
| 6,066,730 A | 5/2000 | Adams et al. |
| 6,083,903 A | 7/2000 | Adams et al. |
| 6,114,308 A | 9/2000 | Claeson et al. |
| 6,297,217 B1 | 10/2001 | Adams et al. |
| 6,313,096 B1 | 11/2001 | Claeson et al. |
| 6,417,174 B1 | 7/2002 | Shoichet et al. |
| 6,617,317 B1 | 9/2003 | Adams et al. |
| 6,713,446 B1 | 3/2004 | Gupta et al. |
| 6,747,150 B1 | 6/2004 | Adams et al. |
| 2004/0138175 A1* | 7/2004 | Madge et al. .................. 514/64 |
| 2004/0147453 A1* | 7/2004 | Deadman et al. .............. 514/19 |
| 2005/0119226 A1 | 6/2005 | Walter et al. |
| 2005/0176651 A1* | 8/2005 | Madge et al. .................. 514/19 |
| 2005/0282757 A1* | 12/2005 | Combe-Marzelle et al. .. 514/18 |
| 2005/0288253 A1* | 12/2005 | Madge et al. .................. 514/64 |

FOREIGN PATENT DOCUMENTS

| EP | 0 235 692 | 2/1987 |
| EP | 0471651 | 2/1992 |
| EP | 0 599 633 | 11/1993 |
| WO | WO 89/09612 | 10/1989 |
| WO | WO 92/07869 | 5/1992 |
| WO | WO 94/21650 | 9/1994 |
| WO | WO 94/21668 | 9/1994 |
| WO | WO 94/25049 | 11/1994 |
| WO | WO 95/09634 | 4/1995 |
| WO | WO 95/09858 | 4/1995 |
| WO | WO 95/09859 | 4/1995 |
| WO | WO 96/12499 | 5/1996 |
| WO | WO 96/13266 | 5/1996 |
| WO | WO 96/20689 | 7/1996 |
| WO | WO 97/05161 | 2/1997 |
| WO | WO 98/00443 | 1/1998 |
| WO | WO 98/31688 | 7/1998 |
| WO | WO 99/26652 | 6/1999 |
| WO | WO 00/35904 | 6/2000 |
| WO | WO 00/35905 | 6/2000 |
| WO | WO 00/41715 | 7/2000 |
| WO | WO 01/02424 | 1/2001 |

(Continued)

OTHER PUBLICATIONS

Skordalakes et al. Crystallographic Structures of Human a-Thrombin Complexed to Peptide Boronic Acids Lacking a Positive Charge at P1. Evidence of Novel Interactions. J Am Chem Soc 1997, vol. 119, pp. 9935-9936.*

(Continued)

Primary Examiner—Bruce R. Campell
Assistant Examiner—Marcela M Cordero Garcia
(74) Attorney, Agent, or Firm—Klarquist Sparkman, LLP

(57) ABSTRACT

Salts of a pharmaceutically acceptable divalent metal and an organoboronic acid drug. Examples of such metals are calcium, magnesium and zinc. The organoboronic acid drug may be a boropeptide protease inhibitor. The salts may be formulated in oral dosage form.

92 Claims, 6 Drawing Sheets

FOREIGN PATENT DOCUMENTS

| | | |
|---|---|---|
| WO | WO 01/41796 | 6/2001 |
| WO | WO 02/36157 | 5/2002 |
| WO | WO 02/059130 | 8/2002 |
| WO | WO 02/059131 | 8/2002 |
| WO | WO 03/007984 | 1/2003 |

OTHER PUBLICATIONS

Deadman et al. Characterization of a Class of Peptide Boronates with Neutral P1 Side Chains as Highly Selective Inhibitors of Thrombin. J Med Chem 1995, vol. 38, pp. 1511-1522.*

Claeson et al. Benzyloxycarbonyl-D-Phe-Pro-methoxypropylboroglycine: a novel inhibitor of thrombin with high selectivity containing a neutral side chain at the P1 position. Biochem J. 1993, vol. 290, pp. 309-312.*

Claeson et al., *Thromb Haemostas*, vol. 65, p. 1289, 1991.

Claeson et al., "Novel peptide mimetics as highly efficient inhibitors of thrombin based on modified D-Phe-Pro-Arg sequences," in *Peptides, Chemistry and Biology*, Smith J A, Rivier J E, Eds., Escom: Leiden pp. 824-825, 1992.

Claeson et al., *Biochem J.* 290:309-312, 1993.

Claeson et al., *The Design of Synthetic Inhibitors of Thrombin* 340:83-89, 1993.

Claeson, *Blood Coagulation and Fibrinolysis* 5:411-436, 1994.

Coburn, *Exp. Opin. Ther. Patents* 11(5):721-738, 2001.

Contreras et al., *J. Org. Chem.* 246:213-217, 1983.

Deadman et al., *J. Medicinal Chemistry* 38:1511-1522, 1995.

Deadman et al., *J. Enzyme Inhibition* 9:29-41, 1995.

Elgendy et al., *Thromb Haemostas* 65:775, 1991.

Elgendy et al., *Tetrahedron Letters* 33(29):4209-4212, 1992.

Elgendy et al., *The Design of Synthetic Inhibitors of Thrombin* 340:173-178, 1993.

Elgendy et al., *Tetrahedron* 50(12):3803-3812, 1994.

Esmail et al., *Thrombosis and Haemostasis* 6:1318, 1995.

Esmail et al., *Thrombosis and Haemostasis* 5:91-92, 1997.

Esmail et al., *Thrombosis and Haemostasis* 5:498-499, 1997.

Gerrard et al., *Thrombosis and Haemostasis* 6:1307, 1995.

Gustafsson et al., *Thrombosis Research* 101:171-181, 2001.

Katz et al., *Biochemistry* 34(26):8264-8280, 1995.

Martichonok et al., *J. Am. Chem. Soc.* 118:950-958, 1996.

Matt et al., *Bioorg. Med. Chem.* 8:2291-2303, 2000.

Matteson, *Chem. Rev.* 89:1535-1551, 1989.

Matteson et al., *J. Org. Chem.* 61:6047-6051, 1996.

Metternich et al., *Naunyn-Schmiedeberg's Arch Pharmocol* 97:345, 1992.

Philipp et al., *The Design of Synthetic Inhibitors of Thrombin* 340:67-77, 1993.

Rewinkel et al., *Current Pharmaceutical Design* 5:1043-1075, 1999.

Saitoh et al., *Pharmaceutical Research* 16(11):1786-1789, 1999.

Sanderson et al., *Current Medicinal Chemistry* 5:289-304, 1998.

Skordalakes et al., *Biochemistry* 37(41):14420-14427, 1998.

Spencer et al., *Tetrahedron* 58:1551-1556, 2002.

Stahl et al., *Handbook of Pharmaceutical Salts Properties, Selection, and Use*, Verlag Helvetica Chimica Acta, Postfach, CH-8042 Züirch, Switzerland, 2002.

Tapparelli et al., *The Journal of Biological Chemistry* 268(7):4734-4741, 1993.

Tapparelli et al., *Trends Pharmacol. Sci.* 14:366-376, 1993.

Trigen Limited, *TRI 50b Non Confidential Information* pp. 1-12, Jul. 2002.

Trigen Limited, "Looking for a career in Biotechnology?" poster exhibited at XVIIth International Symposium on Medicinal Chemistry, Barcelona, Spain, Sep. 5, 2002.

Tripathy et al., *Synthesis* pp. 200-206, 1990.

Wu et al., *Journal of Pharmaceutical Sciences* 89(6):758-765, Jun. 2000.

Yang et al., *Pharmaceutical Research* 16(9):1331-1343, 1999.

Yang et al., *Medicinal Research Reviews* 23(3):346-368, 2003.

Bastin et al., "Salt Selection and Optimisation Procedures for Pharmaceutical New Chemical Entities," *Organic Process Research & Development* 4:427-435, 2000.

Berge et al., "Pharmaceutical Salts," *Journal of Pharmaceutical Sciences* 66(1):1-19, 1977.

Brikh et al., "Boronated thiophenols: a preparation of 4-mercaptophenylboronic acid and derivatives," *Journal of Organometallic Chemistry* 581:82-86, 1999.

Davies et al., "Peroxides of Elements other than Carbon. Part XII. The Autoxidation of Optically Active 1-Phenylethylboronic Acid," *J Chem Soc* pp. 17-22, 1967.

Elgendy et al., "Design of a novel class of bifunctional thrombin inhibitors, synthesised by the first application of peptide boronates of solid phase chemistry," *Tetrahedron Letters* 38(18):3305-3308, 1997.

Hsiao et al., "A Facile Synthesis of *tert*-Butyl 2-[Benzyloxycarbonyl)amino]-3-(4,4,5,5-tetramethyl-1,3,2-dioxaborolan-2-yl)propionate: An Orthogonally Protected Boronic Acid Analog of Aspartic Acid," *Synthesis* 7:1043-1046, 1998.

Kettner et al., "Inhibition of the Serine Proteases Leukocyte Elastase, Pancreatic Elastase, Cathepsin G, and Chymotrypsin by Peptide Boronic Acids," *The Journal of Biological Chemistry* 259(24)15106-15114, 1984.

Kettner et al., "The Selective Inhibition of Thrombin of Peptides of Boroarginine," *The Journal of Biological Chemistry* 265(30):18289-18297, 1990.

Lappert, "Organic Compounds of Boron," *Chem. Review* 56:959-1064, 1956.

Martichonok et al., "Cysteine Proteases such as Papain are not Inhibited by Substrate Analogue Peptidyl Boronic Acids," *Bioorganic and Medicinal Chemistry* 5(4):679-684, 1997.

Snyder et al., "Organoboron Compounds, and the Study of Reaction Mechanisms. Primary Aliphatic Boronic Acids," *Am Chem Soc* 60:105-111, 1938.

Snyder et al., "Aryl Boronic Acids. II. Aryl Boronic Anhydrides and their Amine Complexes," *Am Chem Soc* 80:3611-3615, 1958.

Wityak et al., "Synthesis of Thrombin Inhibitor DuP 714," *J. Org. Chem.* 60:3717-3722, 1995.

Davies, *The Pharmaceutical Journal* 266:322-323, 2001.

* cited by examiner

MULTIVALENT METAL SALTS OF BORONIC ACIDS

BACKGROUND

The present disclosure relates to pharmaceutically useful products obtainable from organoboronic acids. The disclosure also relates to the use of members of the aforesaid class of products, to their formulation, their preparation, their synthetic intermediates and to other subject matter.

The disclosure further relates to oral pharmaceutical formulations containing the described products.

Boronic Acid Compounds

It has been known for some years that boronic acid compounds and their derivatives, e.g. esters, have biological activities, notably as inhibitors or substrates of proteases. For example, Koehler et al. *Biochemistry* 10:2477, 1971 report that 2-phenylethane boronic acid inhibits the serine protease chymotrypsin at millimolar levels. The inhibition of chymotrypsin and subtilisin by arylboronic acids (phenylboronic acid, m-nitro-phenylboronic acid, m-aminophenylboronic acid, m-bromophenylboronic acid) is reported by Phillip et al, *Proc. Nat. Acad. Sci. USA* 68:478–480, 1971. A study of the inhibition of subtilisin Carlsberg by a variety of boronic acids, especially phenyl boronic acids substituted by Cl, Br, $CH_3$, $H_2N$, MeO and others, is described by Seufer-Wasserthal et al, *Biorg. Med. Chem.* 2(1):35–48, 1994.

In describing inhibitors or substrates of proteases, P1, P2, P3, etc. designate substrate or inhibitor residues which are amino-terminal to the scissile peptide bond, and S1, S2, S3, etc., designate the corresponding subsites of the cognate protease in accordance with: Schechter, I. and Berger, A. On the Size of the Active Site in Proteases, *Biochem. Biophys. Res. Comm.*, 27:157–162, 1967. In thrombin, the S1 binding site or "specificity pocket" is a well defined slit in the enzyme, whilst the S2 and S3 binding subsites (also respectively called the proximal and distal hydrophobic pockets) are hydrophobic and interact strongly with, respectively, Pro and (R)-Phe, amongst others.

Pharmaceutical research into serine protease inhibitors has moved from the simple arylboronic acids to boropeptides, i.e. peptides containing a boronic acid analogue of an α-amino carboxylic acid. The boronic acid may be derivatised, often to form an ester. Shenvi (EP-A-145441 and U.S. Pat. No. 4,499,082) disclosed that peptides containing an α-aminoboronic acid with a neutral side chain were effective inhibitors of elastase and has been followed by numerous patent publications relating to boropeptide inhibitors of serine proteases. Specific, tight binding boronic add inhibitors have been reported for elastase ($K_i$, 0.25 nM), chymotrypsin ($K_i$, 0.25 nM), cathepsin G ($K_i$, 21 nM), α-lytic protease ($K_i$, 0.25 nM), dipeptidyl aminopeptidase type IV ($K_i$, 16 pM) and more recently thrombin (Ac-D-Phe-Pro-boroArg-OH (DuP 714 initial $K_i$ 1.2 nM).

Claeson et al (U.S. Pat. No. 5,574,014 and others) and Kakkar et al (WO 92/07869 and family members including U.S. Pat. No. 5,648,338) disclose thrombin inhibitors having a neutral C-terminal side chain, for example an alkyl or alkoxyalkyl side chain.

Modifications of the compounds described by Kakkar et al are included in WO 96/25427, directed to peptidyl serine protease inhibitors in which the P2-P1 natural peptide linkage is replaced by another linkage. As examples of non-natural peptide linkages may be mentioned —$CO_2$—, —$CH_2O$—, —NHCO—, —$CHYCH_2$—, —CH=CH—, —$CO(CH_2)_pCO$— where p is 1, 2 or 3, —COCHY—, —$CO_2$—$CH_2NH$—, —CHY—NX—, —N(X)$CH_2$—N(X)CO—, —CH=C(CN)CO—, —CH(OH)—NH—, —CH(CN)—NH—, —CH(OH)—$CH_2$— or —NH—CHOH—, where X is H or an amino protecting group and Y is H or halogen, especially F. Particular non-natural peptide linkages are —$CO_2$— or —$CH_2O$—.

Metternich (EP 471651 and U.S. Pat. No. 5,288,707, the latter being assigned to Trigen Limited) discloses variants of Phe-Pro-BoroArg boropeptides in which the P3 Phe is replaced by an unnatural hydrophobic amino acid such as trimethylsilylalanine, p-tert.butyl-diphenyl-silyloxymethyl-phenylalanine or p-hydroxymethylphenylalanine and the P1 side chain may be neutral (alkoxyalkyl, alkylthioalkyl or trimethylsilylalkyl).

The replacement of the P2 Pro residue of borotripeptide thrombin inhibitors by an N-substituted glycine is described in Fevig J M et al *Bioorg. Med. Chem.* 8: 301–306 and Rupin A et al *Thromb. Haemost.* 78(4):1221–1227, 1997. See also U.S. Pat. No. 5,585,360 (de Nanteuil et al).

Amparo (WO 96/20698 and family members including U.S. Pat. No. 5,698,538) discloses peptidomimetics of the structure Aryl-linker-Boro(Aa), where Boro(Aa) may be an aminoboronate residue with a non-basic side chain, for example BoroMpg. The linker is of the formula —$(CH_2)_m$CONR— (where m is 0 to 8 and R is H or certain organic groups) or analogues thereof in which the peptide linkage —CONR— is replaced by —CSNR—, —$SO_2NR$—, —$CO_2$—, —C(S)O— or —$SO_2O$—. Aryl is phenyl, naphthyl or biphenyl substituted by one, two or three moieties selected from a specified group. Most typically these compounds are of the structure Aryl-$(CH_2)_n$—CONH—$CHR^2$—$BY^1Y^2$, where $R^2$ is for example a neutral side chain as described above and n is 0 or 1.

Non-peptide boronates have been proposed as inhibitors of proteolytic enzymes in detergent compositions. WO 92/19707 and WO 95/12655 report that arylboronates can be used as inhibitors of proteolytic enzymes in detergent compositions. WO 92/19707 discloses compounds substituted meta to the boronate group by a hydrogen bonding group, especially acetamido (—$NHCOCH_3$), sufonamido (—$NHSO_2CH_3$) and alkylamino. WO 95/12655 teaches that ortho-substituted compounds are superior.

Boronate enzyme inhibitors have wide application, from detergents to bacterial sporulation inhibitors to pharmaceuticals. In the pharmaceutical field, there is patent literature describing boronate inhibitors of serine proteases, for example thrombin, factor Xa, kallikrein, elastase, plasmin as well as other serine proteases like prolyl endopeptidase and Ig AI Protease. Thrombin is the last protease in the coagulation pathway and acts to hydrolyse four small peptides form each molecule of fibrinogen, thus deprotecting its polymerisation sites. Once formed, the linear fibrin polymers may be cross-linked by factor XIIIa, which is itself activated by thrombin. In addition, thrombin is a potent activator of platelets, upon which it acts at specific receptors. Thrombin also potentiates its own production by the activation of factors V and VIII.

Other aminoboronate or peptidoboronate inhibitors or substrates of serine proteases are described in:
U.S. Pat. No. 4,935,493
EP 341661
WO 94/25049
WO 95/09859
WO 96/12499
WO 96/20689
Lee S-L et al, *Biochemistry* 36:13180–13186, 1997

Dominguez C et al, *Bioorg. Med. Chem. Lett.* 7:79–84, 1997
EP 471651
WO 94/20526
WO 95/20603
WO97/05161
U.S. Pat. No. 4,450,105
U.S. Pat. No. 5,106,948
U.S. Pat. No. 5,169,841.

Peptide boronic acid inhibitors of hepatic C virus protease are described in WO 01/02424.

Matteson D S *Chem. Rev.* 89: 1535–1551, 1989 reviews the use of α-halo boronic esters as intermediates for the synthesis of inter alia amino boronic acids and their derivatives. Matteson describes the use of pinacol boronic esters in non-chiral synthesis and the use of pinanediol boronic esters for chiral control, including in the synthesis of amino and amido boronate esters.

Contreras et al *J. Organomet. Chem.* 246: 213–217, 1983 describe how intramolecular N→B coordination was demonstrated by spectroscopic studies on cyclic boronic esters prepared by reacting $Me_2CHCMe_2$—$BH_2$ with diethanolamines.

Boronic acid and ester compounds have displayed promise as inhibitors of the proteasome, a multicatalytic protease responsible for the majority of intracellular protein turnover. Ciechanover, *Cell,* 79:13–21, 1994, teaches that the proteasome is the proteolytic component of the ubiquitin-proteasome pathway, in which proteins are targeted for degradation by conjugation to multiple molecules of ubiquitin. Ciechanover also teaches that the ubiquitin-proteasome pathway plays a key role in a variety of important physiological processes.

Adams et al, U.S. Pat. No. 5,780,454 (1998), U.S. Pat. No. 6,066,730 (2000), U.S. Pat. No. 6,083,903 (2000) and equivalent WO 96/13266, and U.S. Pat. No. 6,297,217 (2001) describe peptide boronic ester and acid compounds useful as proteasome inhibitors. These documents also describe the use of boronic ester and acid compounds to reduce the rate of muscle protein degradation, to reduce the activity of $NF-_\kappa B$ in a cell, to reduce the rate of degradation of p53 protein in a cell, to inhibit cyclin degradation in a cell, to inhibit the growth of a cancer cell, to inhibit antigen presentation in a cell, to inhibit $NF-_\kappa B$ dependent cell adhesion, and to inhibit HIV replication. Brand et al, WO 98/35691, teaches that proteasome inhibitors, including boronic acid compounds, are useful for treating infarcts such as occur during stroke or myocardial infarction. Elliott et al, WO 99/15183, teaches that proteasome inhibitors are useful for treating inflammatory and autoimmune diseases.

Unfortunately, organoboronic acids can be relatively difficult to obtain in analytically pure form. Thus, alkylboronic acids and their boroxines are often air-sensitive. Korcek et al, *J. Chem. Soc. Perkin Trans.* 2:242, 1972, teaches that butylboronic acid is readily oxidized by air to generate 1-butanol and boric acid.

It is known that derivatisation of boronic acids as cyclic esters provides oxidation resistance. For example, Martichonok V et al *J. Am. Chem. Soc.* 118: 950–958, 1996 state that diethanolamine derivatisation provides protection against possible boronic acid oxidation. U.S. Pat. No. 5,681,978 (Matteson D S et al) teaches that 1,2-diols and 1,3 diols, for example pinacol, form stable cyclic boronic esters that are not easily oxidised.

Wu et al, *J. Pharm. Sci.,* 89:758–765, 2000, discuss the stability of the compound N-(2-pyrazine) carbonyl-phenylalanine-leucine boronic acid (LDP-341, also known as bortezomib), an anti-cancer agent. It is described how "dur-ing an effort to formulate [LDP-341] for parenteral administration, the compound showed erratic stability behaviour". The degradation pathways were investigated and it was concluded that the degradation was oxidative, the initial oxidation being attributed to peroxides or molecular oxygen and its radicals.

WO 02/059131 discloses boronic acid products which are described as stable. In particular, these products are certain boropeptides and/or boropeptidomimetics in which the boronic acid group has been derivatised with a sugar. The disclosed sugar derivatives, which have hydrophobic amino acid side chains, are of the formula

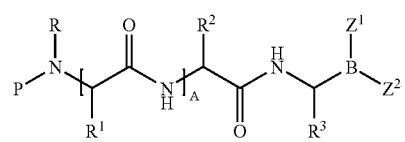

wherein:

P is hydrogen or an amino-group protecting moiety;

R is hydrogen or alkyl;

A is 0, 1 or 2;

$R^1$, $R^2$ and $R^3$ are independently hydrogen, alkyl, cycloalkyl, aryl or —$CH_2$—$R^5$;

$R^5$, in each instance, is one of aryl, aralkyl, alkaryl, cycloalkyl, heterocyclyl, heteroaryl, or —W—$R^6$, where W is a chalcogen and $R^6$ is alkyl;

where the ring portion of any of said aryl, aralkyl, alkaryl, cycloalkyl, heterocyclyl, or heteroaryl in $R^1$, $R^2$, $R^3$ or $R^5$ can be optionally substituted; and $Z^1$ and $Z^2$ together form a moiety derived from a sugar, wherein the atom attached to boron in each case is an oxygen atom.

Some of the disclosed compounds are sugar derivatives of LDP-341 (see above).

Many drugs comprise an active moiety which is a carboxylic acid. There are a number of differences between carboxylic acids and boronic acids, whose effects on drug delivery, stability and transport (amongst others) have not been investigated. One feature of trivalent boron compounds is that the boron atom is $sp^2$ hybridised, which leaves an empty $2p_z$ orbital on the boron atom. A molecule of the type $BX_3$ can therefore act as an electron-pair acceptor, or Lewis acid. It can use the empty $2p_z$ orbital to pick up a pair of nonbonding electrons from a Lewis base to form a covalent bond. $BF_3$ therefore reacts with Lewis bases such as $NH_3$ to form acid-base complexes in which all of the atoms have a filled shell of valence electrons.

Boric acid, accordingly, can act as a Lewis acid, accepting $OH^-$:

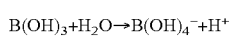

Further, boronic acids of the type $RB(OH)_2$ are dibasic and have two pKa's. Another point of distinction about boron compounds is the unusually short length of bonds to boron, for which three factors may be responsible:

1. Formation of pπ—pπ bonds;
2. Ionic-covalent resonance;
3. Reduced repulsions between non-bonding electrons.

The presumed equilibria of boronic and carboxylic acids in aqueous KOH are shown below (excluding formation of $RBO_2^{2-}$):

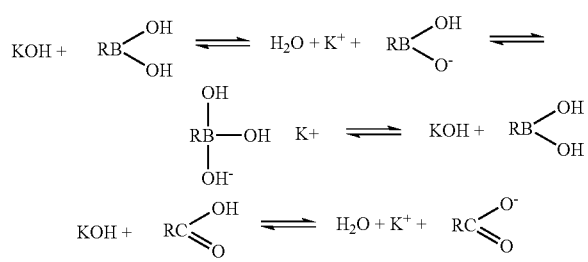

Thrombosis

Hemostasis is the normal physiological condition of blood in which its components exist in dynamic equilibrium. When the equilibrium is disturbed, for instance following injury to a blood vessel, certain biochemical pathways are triggered leading, in this example, to arrest of bleeding via clot formation (coagulation). Coagulation is a dynamic and complex process in which proteolytic enzymes such as thrombin play a key role. Blood coagulation may occur through either of two cascades of zymogen activations, the extrinsic and intrinsic pathways of the coagulation cascade. Factor VIIa in the extrinsic pathway, and Factor IXa in the intrinsic pathway are important determinants of the activation of factor X to factor Xa, which itself catalyzes the activation of prothrombin to thrombin, whilst thrombin in turn catalyses the polymerization of fibrinogen monomers to fibrin polymer. The last protease in each pathway is therefore thrombin, which acts to hydrolyze four small peptides (two FpA and two FpB) from each molecule of fibrinogen, thus deprotecting its polymerization sites. Once formed, the linear fibrin polymers may be cross-linked by factor XIIIa, which is itself activated by thrombin. In addition, thrombin is a potent activator of platelets, upon which it acts at specific receptors. Thrombin activation of platelets leads to aggregation of the cells and secretion of additional factors that further accelerate the creation of a hemostatic plug. Thrombin also potentiates its own production by the activation of factors V and VIII (see Hemker and Beguin in: Jolles, et. al., "Biology and Pathology of Platelet Vessel Wall Interactions," pp. 219–26 (1986), Crawford and Scrutton in: Bloom and Thomas, "Haemostasis and Thrombosis," pp. 47–77, (1987), Bevers, et. al., Eur. J. Biochem. 122:429–36, 1982, Mann, Trends Biochem. Sci. 12:229–33, 1987).

Proteases are enzymes which cleave proteins at specific peptide bonds. Cuypers et al., J. Biol. Chem. 257:7086, 1982, and the references cited therein, classify proteases on a mechanistic basis into five classes: serine, cysteinyl or thiol, acid or aspartyl, threonine and metalloproteases. Members of each class catalyse the hydrolysis of peptide bonds by a similar mechanism, have similar active site amino acid residues and are susceptible to class-specific inhibitors. For example, all serine proteases that have been characterised have an active site serine residue.

The coagulation proteases thrombin, factor Xa, factor VIIa, and factor IXa are serine proteases having trypsin-like specificity for the cleavage of sequence-specific Arg-Xxx peptide bonds. As with other serine proteases, the cleavage event begins with an attack of the active site serine on the scissile bond of the substrate, resulting in the formation of a tetrahedral intermediate. This is followed by collapse of the tetrahedral intermediate to form an acyl enzyme and release of the amino terminus of the cleaved sequence. Hydrolysis of the acyl enzyme then releases the carboxy terminus.

As indicated above, platelets play two important roles in normal hemostasis. First, by aggregating, they constitute the initial hemostatic plug which immediately curtails bleeding from broken blood vessels. Secondly, the platelet surface can become activated and potentiate blood clotting, a property referred to as platelet procoagulant activity. This may be observed as an increase in the rate of activation of prothrombin by factor Xa in the presence of factor Va and $Ca^{2+}$, referred to as the prothrombinase reaction. Normally, there are few (if any) clotting factors on the surface of unstimulated platelets but, when platelets are activated, negatively charged phospholipids (phosphatidylserine and phospatidylinositol) that are normally on the cytoplasmic side of the membrane become available and provide a surface on which two steps of the coagulation sequence occur. The phospholipid on the surface of activated platelets profoundly accelerates the reactions leading to the formation of thrombin, so that thrombin can be generated at a rate faster than its neutralisation by antithrombin III. The reactions that occur on the platelet surfaces are not easily inhibited by the natural anticoagulants in blood such as antithrombin III, either with or without heparin. (See Kelton and Hirsch in: Bloom and Thomas, "Haemostasis and Thrombosis," pp. 737–760, (1981); Mustard et al in: Bloom and Thomas, "Haemostasis and Thrombosis," pp. 503526, (1981); Goodwin et al; Biochem. J. 308:15–21, 1995).

A thrombus can be considered as an abnormal product of a normal mechanism and can be defined as a mass or deposit formed from blood constituents on a surface of the cardiovascular system, for example of the heart or a blood vessel. Thrombosis can be regarded as the pathological condition wherein improper activity of the hemostatic mechanism results in intravascular thrombus formation. Three basic types of thrombi are recognised:

the white thrombus which is usually seen in arteries and consists chiefly of platelets;

the red thrombus which is found in veins and is composed predominantly of fibrin and red cells;

the mixed thrombus which is composed of components of both white and red thrombi.

The composition of thrombi is influenced by the velocity of blood flow at their sites of formation. In general white platelet-rich thrombi form in high flow systems, while red coagulation thrombi form in regions of stasis. The high shear rate in arteries prevents the accumulation of coagulation intermediates on the arterial side of the circulation: only platelets have the capacity to form thrombi binding to the area of damage via von Willebrand factor. Such thrombi composed only of platelets are not stable and disperse. If the stimulus is strong then the thrombi will form again and then disperse continually until the stimulus has diminished. For the thrombus to stabilise, fibrin must form. In this respect, small amounts of thrombin can accumulate within the platelet thrombus and activate factor Va and stimulate the platelet procoagulant activity. These two events lead to an overall increase in the rate of activation of prothrombin by factor Xa of 300,000 fold. Fibrin deposition stabilises the platelet thrombus. Indirect thrombin inhibitors, for example heparin, are not clinically effective at inhibiting stimulation of platelet procoagulant activity. Accordingly, a therapeutic agent which inhibits platelet procoagulant activity would be useful for treating or preventing arterial thrombotic conditions.

On the venous side of circulation, the thrombus is comprised of fibrin: thrombin can accumulate because of the slower flow on the venous side and platelets play only a minor role.

Thrombosis is thus not considered to be a single indication but, rather, is a class of indications embracing distinct sub-classes for which differing therapeutic agents and/or protocols may be appropriate. Thus, regulatory authorities treat disorders such as, for example, deep vein thrombosis, cerebrovascular arterial thrombosis and pulmonary embolism as distinct indications for the purposes of licensing medicines. Two main sub-classes of thrombosis are arterial thrombosis and venous thrombosis. Arterial thrombosis includes such specific disorders as acute coronary syndromes [for example acute myocardial infarction (heart attack, caused by thrombosis in a coronary artery)], cerebrovascular arterial thrombosis (stroke, caused by thrombosis in the cerebrovascular arterial system) and peripheral arterial thrombosis. Examples of conditions caused by venous thrombosis are deep vein thrombosis and pulmonary embolism.

The management of thrombosis commonly involves the use of antiplatelet drugs (inhibitors of platelet aggregation) to control future thrombogenesis and thrombolytic agents to lyse the newly formed clot, either or both such agents being used in conjunction or combination with anticoagulants. Anticoagulants are used also preventatively (prophylactically) in the treatment of patients thought susceptible to thrombosis.

Currently, two of the most effective classes of drugs in clinical use as anticoagulants are the heparins and the vitamin K antagonists. The heparins are ill-defined mixtures of sulfated polysaccharides that bind to, and thus potentiate, the action of antithrombin III. Antithrombin III is a naturally occurring inhibitor of the activated clotting factors IXa, Xa, XIa, thrombin and probably XIIa (see Jaques, *Pharmacol. Rev.* 31:99–166, 1980). The vitamin K antagonists, of which warfarin is the most well-known example, act indirectly by inhibiting the post-ribosomal carboxylations of the vitamin K dependent coagulation factors II, VII, IX and X (see Hirsch, *Semin. Thromb. Hemostasis* 12:1–11, 1986). While effective therapies for the treatment of thrombosis, heparins and vitamin K antagonists have the unfortunate side effects of bleeding, heparin-induced thrombocytopenia (in the case of heparin) and marked interpatient variability, resulting in a small and unpredictable therapeutic safety margin.

The use of direct acting inhibitors of thrombin and other serine protease enzymes of the coagulation system is expected to alleviate these problems. To that end, a wide variety of serine protease inhibitors have been tested, including boropeptides, i.e. peptides containing a boronic acid analogue of an α-amino acid. Whilst direct acting boronic acid thrombin inhibitors have been discussed earlier in this specification, they are further described in the following section.

Neutral P1 Residue Boropeptide Thrombin Inhibitors

Claeson et al (U.S. Pat. No. 5,574,014 and others) and Kakkar et al (WO 92/07869 and family members including U.S. Pat. No. 5,648,338) disclose lipophilic thrombin inhibitors having a neutral (uncharged) C-terminal (P1) side chain, for example an alkoxyalkyl side chain.

The Claeson et al and Kakkar et al patent families disclose boronate esters containing the amino acid sequence D-Phe-Pro-BoroMpg [(R)-Phe-Pro-BoroMpg], which are highly specific inhibitors of thrombin. Of these compounds may be mentioned in particular Cbz-(R)-Phe-Pro-BoroMpg-OPinacol (also known as TRI 50b). The corresponding free boronic acid is known as TRI 50c. For further information relating to TRI 50b and related compounds, the reader is referred to the following documents:

Elgendy S et al., in *The Design of Synthetic Inhibitors of Thrombin*, Claeson G et al Eds, *Advances in Experimental Medicine*, 340:173–178, 1993.

Claeson G et al, *Biochem J.* 290:309–312, 1993

Tapparelli C et al, *J Biol Chem*, 268:4734–4741, 1993

Claeson G, in *The Design of Synthetic Inhibitors of Thrombin*, Claeson G et al Eds, *Advances in Experimental Medicine*, 340:83–91, 1993

Phillip et al, in *The Design of Synthetic Inhibitors of Thrombin*, Claeson G et al Eds, *Advances in Experimental Medicine*, 340:67–77, 1993

Tapparelli C et al, *Trends Pharmacol. Sci.* 14:366–376, 1993

Claeson G, *Blood Coagulation and Fibrinolysis* 5:411–436, 1994

Elgendy et al, *Tetrahedron* 50:3803–3812, 1994

Deadman J et al, *J. Enzyme Inhibition* 9:29–41, 1995

Deadman J et al, *J. Medicinal Chemistry* 38:1511–1522, 1995.

The tripeptide sequence of TRI 50b has three chiral centres. The Phe residue is considered to be of (R)-configuration and the Pro residue of natural (S)-configuration, at least in compounds with commercially useful inhibitor activity; the Mpg residue is believed to be of (R)-configuration in isomers with commercially useful inhibitor activity. Thus, the active, or most active, TRI 50b stereoisomer is considered to be of R,S,R configuration and may be represented as:

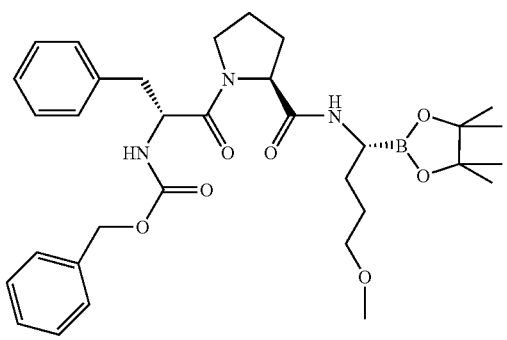

(RSR)-TRI 50b: Cbz-(R)-Phe-(S)-Pro-(R)-boroMpg Pinacol

Whilst indirect acting thrombin inhibitors have been found useful for the treatment of patients susceptible to or suffering from venous thrombosis, the same is not true of arterial thrombosis, because it would be necessary to raise the dosage used in the treatment of venous thrombosis by many times in order to treat (prevent) arterial thrombosis. Such raised dosages typically cause bleeding, which makes indirect acting thrombin inhibitors unsuitable or less preferable for treating arterial thrombosis. Heparin and its low molecular weight derivatives are indirect thrombin inhibitors, and so are unsuitable to treat arterial thrombosis. Oral direct thrombin inhibitors are in development for arterial indications but may have lower than desirable therapeutic indices, i.e. may have higher than desirable levels of bleeding at therapeutic doses.

Oral Absorption

Absorption in the gastrointestinal tract can be by an active or a passive route. Active absorption by transport mechanisms tends to be variable between individuals and with intestinal content (Gustafsson et al, *Thrombosis Research*, 101:171–181, 2001). The upper intestine has been identified as the principal site of oral drug absorption. In particular, the duodenum is the customary target site for absorption of orally administered drugs because of its large surface area. The intestinal mucosa acts as a barrier that controls passive transcellular absorption: the absorption of ionic species is blocked whilst the transcellular absorption of lipophilic molecules is favoured (Palm K et al., *J. Pharmacol and Exp. Therapeutics*, 291:435–443, 1999).

Orally administered drugs are required to be consistently and adequately absorbed. Variability of absorption between individuals or between different occasions in the same individual is unwelcome. Similarly, drugs which have a low level of bioavailability (only a small portion of the administered active agent is absorbed) are generally unacceptable.

Non-ionised compounds are favoured for passive absorption, a route associated with invariability, and are therefore preferred for consistent absorption. Lipophilic species are particularly favoured by passive absorption mechanisms and, accordingly, non-ionic, lipophilic drugs are indicated to be most favoured for consistent and high oral absorption.

Many organoboronic acid compounds may be classified as lipophilic or hydrophobic. Typically, such compounds include amongst others:

boropeptides of which all or a majority of the amino acids are hydrophobic boropeptides of which at least half of the amino acids are hydrophobic and which have a hydrophobic N-terminal substituent (amino protecting group)

non-peptides based on hydrophobic moieties.

Typical functionalities required for interaction of drugs with their physiological targets are functional groups such as carboxylic and sulphonic acids. These groups exist as the protonated form in the stomach (at pH 2–3), but will be ionised to some extent at the higher pH of the intestinal fluid. One strategy that has been used to avoid the ionisation of the carboxylates or sulphonates is to present them as ester forms, which are cleaved once absorbed into the vascular lumen.

For example, the direct acting thrombin inhibitor melagatran, which has sub-optimal gastrointestinal absorption, has terminal carboxy and amidino groups and is a pure zwitterion at pH 8–10 when the carboxylic acid and amidino groups are both charged. A prodrug H 376/95 was therefore developed which has protecting groups for the carboxylic acid and for the amidine and is a more lipophilic molecule than melagatran. The prodrug has a permeability coefficient across cultured epithelial Caco-2 cells 80 times higher than that of melagatran and oral bioavailability 2.7–5.5 times higher than that of melagatran as well as much smaller variability in the area under the drug plasma concentration vs. time curve (Gustafsson et al, *Thrombosis Research*, 101:171–181, 2001).

Boronic acids are divalent functional groups, with boron-oxygen bond lengths (1.6 Å) more typical of single bonds, unlike superficially comparable C—O and S—O bonds in carboxylic and sulphonic acids. Consequently the boronic acid group has two ionisation potentials. The boronic acid group will be partly ionised at pH's of the duodenal fluid and not suited to the desired passive duodenal uptake. Thus, a charged boronate inhibitor H-D-PheProBoroArg is absorbed by a predominantly active transport mechanism (Saitoh, H. and Aungst, B. J., *Pharm. Res.*, 16:1786–1789, 1999).

Oral Absorption of Boropeptides, Boropeptidomimetics and other Organoboronates

The boronate ester group of TRI 50b is rapidly cleaved in the conditions of the plasma to form the corresponding boronic acid group, which is considered to be the active moiety which inhibits the catalytic site of thrombin.

The peptide boronic acid formed by such cleavage of TRI 50b (the acid is designated TRI 50c) is relatively insoluble in water, especially at acidic or neutral pH, and tends to be poorly absorbed in the stomach and duodenum. The acid has the structure Cbz-Phe-Pro-BoroMpg-OH.

Whereas the peptide boronic acid Cbz-Phe-Pro-BoroMpg-OH is partly ionised under duodenal conditions and, to that extent, unfavoured for passive transport, esters of the acid are designed for a high rate of passive (thus consistent) transport. The tripeptide sequence Phe-Pro-Mpg has a non-basic P1 side chain (specifically, methoxypropyl), such that the tripeptide consists of three non-polar amino acids. The esters of the peptide boronic acid are non-ionisable and the ester-forming species further impart lipophilic properties, so encouraging a high rate of passive transport.

Computational techniques have confirmed that TRI 50b and other diol esters of Cbz-Phe-Pro-BoroMpg-OH can be predicted to have good bioavailability. Thus, polar surface area (PSAd) is a parameter predictive of bioavailability and PSAd values of greater than 60 Å correlate well with passive transcellular transport and with bioavailability of known drugs (Kelder, *J. Pharm. Res.*, 16:1514–1519, 1999). Measurements for diol esters of the above peptide boronic acid, including the pinacol ester TRI 50b, show that the diol esters have PSAd values well above 60 Å, predictive of passive transport and good bioavailability as shown in Table 1:

TABLE 1

PSAd values of selected diol esters f Cbz-Phe-Pro-BoroMpg-OH

| Diol | PSAd Value |
| --- | --- |
| Pinacol | 98.74 |
| Pinanediol | 90.64 |

The corresponding monohydroxy alcohol (e.g. alkanol) esters were considered too unstable, spontaneously cleaving to liberate the acid in-vitro. Esters of diols such as pinanediol and pinacol have enhanced kinetic stability over esters of monohydroxy alcohols, in that after partial hydrolysis to the mono-ester derivative they will tend to reassociate by a facile intra-molecular reaction.

BRIEF SUMMARY OF THE DISCLOSURE

To counterbalance the highly desirable features of TRI 50b, it has been discovered that TRI 50b tends to hydrolyse. Thus in acid conditions, for example HPLC assay, TRI 50b is converted to the acid form with a short half life, which implies potential hydrolysis in the duodenum and elsewhere in the gastrointestinal tract into ionic species which would resist passive transport and, if anything, be absorbed by active transport, indicative at best of variable bioavailability.

The instability of TRI 50b to hydrolysis also presents potential disadvantages in preparation of the compound and its formulation, as well as in the storage of pharmaceutical formulations containing it.

Another challenging difficulty which has been posed by TRI 50b is that the data show significant variation in bioavailability between subjects. Such variability can make a drug candidate unacceptable and it would therefore be desirable to reduce the observed variability.

An ideal solution to the instability of TRI 50b would be development of a diol ester more stable to hydrolysis, as such a diol ester like TRI 50b can be predicted to be oxidation resistant as compared with TRI 50c. In this regard, it is known that ring size can affect boronate stability and glycolato boron has been shown to have enhanced aqueous stability compared to pinacol (D. S. Matteson, Stereodirected Synthesis with Organoboranes, Springer-Verlag, 1995, ch. 1). Similarly, the pinanediol ester is more stable than the pinacol; this is believed to be because the pinanediol group is highly sterically hindered and disfavours nucleophilic attack on the boron. In fact transesterification from pinacol to pinanediol has been reported (Brosz, C S, *Tet. Assym,* 8:1435–1440, 1997) whereas the reverse process is unfavourable. The pinanediol ester however is considered too slow to cleave in plasma and there remains a need to provide an improved diol ester.

Another solution to the instability of TRI 50b would be to administer in its place TRI 50c. However, TRI 50c data suggest that TRI 50c too suffers from variability in bioavailability.

TRI 50c suffers further from instability, in that there is a problematic tendency for the boropeptide moiety itself to degrade via de-boronation (carbon-boron bond cleavage), by a pathway previously considered to be oxidative as taught by the literature teaching (e.g. Wu et al, discussed above). The level of degradation can be remarkably high.

The properties discussed above of TRI 50b and TRI 50c will not be restricted to such compounds but will be shared by other boropeptide esters and acids, even if the properties of such other boropeptides differ quantitatively.

The present disclosure is predicated on, amongst other things, the finding that certain organoboronic acid products are indicated to be of enhanced stability. Another basis of the disclosure is the provision of organoboronic acid products having unexpectedly favourable bioavailability.

The benefits of the present disclosure include a solution to the problem of boronate diol ester and especially TRI 50b instability, that is to say the presently disclosed products provide inter alia pharmacologically active compounds which are more stable than TRI 50b and other comparable esters in the sense of stability to hydrolysis. The disclosure further includes a solution to the problem of organoboronic acid instability, that is to say the presently disclosed products provide inter alia pharmacologically active compounds which are more stable to deboronation than TRI 50c. The stability provided within the framework of the disclosure is not absolute but is improved relative to the comparator compounds. The benefits offered by the disclosure further include the provision of unexpected products which, contrary to expectation, have a particularly low variability in oral bioavailability.

In one aspect, disclosed herein is a salt of a pharmaceutically acceptable multivalent (at least divalent) metal and an organoboronic acid drug. As a class, such salts are not only contrary to the direction of the prior art but additionally have an improved level of stability which cannot be explained or predicted on the basis of known chemistry. The salts are indicated to have unexpectedly high and consistent oral bioavailability not susceptible of explanation on the basis of known mechanisms.

The disclosure includes amongst other things a class of salts of which the drug (the free acid) has no charged group at physiological pH other than its boronate (boronic acid) moiety and an amino moiety. The disclosure includes a class of salts of which the drug (the free acid) is a peptide boronate all of whose amino acid residues have uncharged side chains.

In certain embodiments the organoboronic acid is hydrophobic. Particular organoboronic acids have a partition coefficient between 1-n-octanol and water expressed as log P of greater than 1.0 at physiological pH and 25° C. Some useful hydrophobic organoboronic adds have a partition coefficient of at least 1.5. A class of useful hydrophobic organoboronic acids has a partition coefficient of no more than 5.

One particular class of salts comprises those wherein the organoboronic acid comprises a boropeptide or boropeptidomimetic. Boropeptide drugs which may beneficially be prepared as salts include without limitation those of the formula $X-(aa)_n-B(OH)_2$, where X is H or an amino-protecting group, n is 2, 3 or 4, (especially 2 or 3) and each aa is independently a hydrophobic amino acid, whether natural or unnatural.

Disclosed as certain examples are multivalent metal salts of hydrophobic boronic acid inhibitors of thrombin. Such inhibitors may contain hydrophobic amino acids, and this class of amino acids includes those whose side chain is hydrocarbyl, hydrocarbyl containing an in-chain oxygen and/or linked to the remainder of the molecule by an in-chain oxygen or heteroaryl, or any of the aforesaid groups when substituted by hydroxy, halogen or trifluoromethyl. Representative hydrophobic side chains include alkyl, alkoxyalkyl, either of the aforesaid when substituted by at least one aryl or heteroaryl, aryl, heteroaryl, aryl substituted by at least one alkyl and heteroaryl substituted by at least one alkyl. Proline and other imino acids which are ring-substituted by nothing or by one of the moieties listed in the previous sentence are also hydrophobic.

Some hydrophobic side chains contain from 1 to 20 carbon atoms, e.g. non-cyclic moieties having 1, 2, 3 or 4 carbon atoms. Side chains comprising a cyclic group typically but not necessarily contain from 5 to 13 ring members and in many cases are phenyl or alkyl substituted by one or two phenyls.

Included are inhibitors which contain hydrophobic non-peptide moieties, which are typically based on moieties which may form a side chain of a hydrophobic amino acid, as described above.

Hydrophobic compounds may contain, for example, one amino group and/or one acid group (e.g.—COOH, $—B(OH)_2$). Generally, they do not contain multiple polar groups of any one type.

One class of hydrophobic organoboronic acids have a partition coefficient between 1-n-octanol and water expressed as log P of greater than 1 at physiological pH and 25° C. For example, TRI 50c has a partition coefficient of approximately 2.

Some sub-classes of hydrophobic organoboronic acids are those described by Formulae (I) and (III)) below, under the heading "Detailed Description of Several Examples".

The disclosure includes base addtion salts of peptide boronic acids which have a partition coefficient between 1-n-octanol and water expressed as log P of greater than 1.0 at physiological pH and 25° C. Some useful peptide boronic acids have a partition coefficient of at least 1.5. A class of useful hydrophobic peptide boronic acids has a partition coefficient of no more than 5.

In a sub-class of the salts of boropeptides/boropeptidomimetics, the organoboronic acid is of the formula (I):

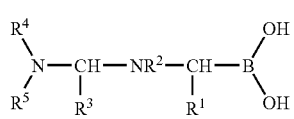

where:
R$^1$ is H or a neutral side group;
R$^2$ is H or C$_1$–C$_{13}$ hydrocarbyl optionally containing in-chain oxygen or sulfur and optionally substituted by a substituent selected from halo, hydroxy and trifluoromethyl;
or R$^1$ and R$^2$ together form a C$_1$–C$_{13}$ moiety which in combination with N—CH forms a 4–6 membered ring and which is selected from alkylene (whether branched or linear) and alkylene containing an in-chain sulfur or linked to N—CH through a sulfur;
R$^3$ is the same as or different from R$^1$ provided that no more than one of R$^1$ and R$^2$ is H, and is H or a neutral side group;
R$^4$ is H or C$_1$–C$_{13}$ hydrocarbyl optionally containing in-chain oxygen or sulfur and optionally substituted by a substituent selected from halo, hydroxy and trifluoromethyl;
or R$^3$ and R$^4$ together form a C$_1$–C$_{13}$ moiety which in combination with N—CH forms a 4–6 membered ring and which is selected from alkylene (whether branched or linear) and alkylene containing an in-chain sulfur or linked to N—CH through a sulfur; and
R$^5$ is X-E- wherein E is nothing or a hydrophobic moiety selected from the group consisting of amino acids (natural or unnatural) and peptides of two or more amino acids (natural or unnatural) of which more than half are hydrophobic and X is H or an amino-protecting group.

Also disclosed are pharmaceutically acceptable multivalent metal salts of a peptide boronic add of formulae (II), (III) or (IV) below.

The boronic acids of formulae (III) and (IV) inhibit thrombin. They exhibit anti-thrombotic activity in both venous and arterial contexts, and are considered to inhibit platelet pro-coagulant activity. One example of a boronic acid of formulae (III) and (IV) is TRI 50c.

The Examples in this disclosure contain data showing that the calcium salt of TRI 50c is markedly less soluble than the potassium salt and yet has higher oral bioavailability and higher consistency of oral bioavailability. The finding of an inverse relationship between solubility and bioavailability of two salts is particularly unpredictable. There is no known property of organoboronic acid drugs which accounts for this finding. The disclosure therefore includes amongst other subject matter a TRI 50c derivative which enhances stability as compared with TRI 50b and reduces the variability in absorption which has been observed with TRI 50b and TRI 50c, and advantageously enables adequately consistent and high bioavailability.

The Examples in this disclosure also contain data demonstrating that the calcium salt of TRI 50c is markedly more stable than TRI 50c. Again, there is no known property which accounts for this finding.

The families of compounds represented by formulae (III) and (IV) represent near neighbours of TRI 50c which can be predicted to have particularly similar properties to TRI 50c.

Calcium is a representative of a class of pharmaceutically acceptable multivalent metals. It is also a representative of a class of pharmaceutically acceptable divalent metals; as other members of the class may be mentioned magnesium and zinc.

TRI 50c is distinguished from most other organic acid drugs in that the acid group of TRI 50c is a boronic acid and not a carboxylic acid. The data in this disclosure are indicative of multivalent metal salts of organoboronic acid drugs providing a technical effect, not linked to solubility, which enhances the amount and consistency of bioavailability. It does not follow that, because the effect is not linked to solubility, there will in every individual case be for that acid a quantitative relationship between solubility and bioavailability like that observed for TRI 50c.

There is a debate in the literature as to whether boronates in aqueous solution form the 'trigonal' B(OH)$_2$ or 'tetrahedral' B(OH)$_3^-$ boron species, but NMR evidence seems to indicate that at a pH below the first pKa of the boronic acid the main boron species is the neutral B(OH)$_2$. In the duodenum the pH is likely to be between 6 and 7, so the trigonal species is likely to be predominant here. In any event, the symbol —B(OH)$_2$ includes tetrahedral as well as trigonal boron species, and throughout this specification symbols indicating trigonal boron species embrace also tetrahedral species. The symbol may further include boronic groups in anhydride form.

The salts may be in the form of solvates, particularly hydrates.

The salts may comprise, or consist essentially of, acid salts in which the boronic acid is singly deprotonated. The disclosure therefore includes products having a metal/boronate stoichiometry consistent with the boronate groups in the product predominantly (more than 50 mol %) carrying a single negative charge.

Oral formulations of the salts are also provided herein. In particular, there are provided oral formulations comprising the salts in the solid phase, for example particulate salts formulated as compressed tablets or as capsules.

According to a further aspect of the present disclosure, there is provided a method of treatment of a condition where anti-thrombotic activity is required which method comprises oral administration of a therapeutically effective amount of a multivalent metal salt of a boronic acid of formula (III) to a person suffering from, or at risk of suffering from, such a condition.

The salts described herein include products obtainable by (having the characteristics of a product obtained by) reaction of the boronic acid with a base of a multivalent metal and the term "salt" herein is to be understood accordingly. The term "salt" in relation to the disclosed products, therefore, does not necessarily imply that the products contain discrete cations and anions and is to be understood as embracing products which are obtainable using a reaction of a boronic acid and a base. The disclosure embraces products which, to a greater or lesser extent, are in the form of a coordination compound. The disclosure thus provides also products obtainable by (having the characteristics of a product obtained by) reaction of an organoboronic acid drug with a multivalent metal base a well as the therapeutic, including prophylactic, use of such products.

The present disclosure is not limited as to the method of preparation of the salts, provided that they contain a boronate species derived from boronic acid (I) and a counter-ion. Such boronate species may be boronate anions in any equilibrium form thereof. The term "equilibrium form" refers to differing forms of the same compounds which may be represented in an equilibrium equation (e.g. boronic acid in equilibrium with a boronic anhydride and in equilibrium with different boronate ions). Boronates in the solid phase may form anhydrides and the disclosed boronate salts when in the solid phase may comprise boronate anhydrides, as a boronic equilibrium species. It is not required that the salts be prepared by reaction of a base containing the counter-ion and the boronic acid (I). Further, the disclosure includes salt products which might be regarded as indirectly prepared by such an acid/base reaction as well as salts obtainable by (having the characteristics of products obtained by) such indirect preparation. As examples of possibly indirect preparation may be mentioned processes in which, after initial recovery of the salt, it is purified and/or treated to modify its physicochemical properties, for example to modify solid form or hydrate form, or both.

In some embodiments the salts comprise anhydride species; in others they are essentially free of anhydride species.

The salts may be in isolated form. The salts may have a purity, e.g. as determined by the method of Example 13, of at least about 90%, e.g. of greater than or equal to about 95%. In the case of pharmaceutical formulations, such salt forms may be combined with pharmaceutically acceptable diluents, excipients or carriers.

The disclosure includes a method for preparing the salts from the corresponding boronic acid as an intermediate, as well as the intermediate boronic acid of Formula (III) and a method for preparing it.

Further aspects and embodiments of the disclosure are set forth in the following description and claims.

Throughout the description and claims of this specification, the words "comprise" and "contain" and variations of the words, for example "comprising" and "comprises", mean "including but not limited to", and are not intended to (and do not) exclude other moieties, additives, components, integers or steps.

This patent application contains data indicating that the stability (resistance to deboronation) of organoboronic acids may be increased by providing them in the form of salts with multivalent metals. The salt may be an acid salt. This stabilisation technique forms part of the disclosure and is applicable, inter alia, to organoboronic acids described under the heading "BACKGROUND" and to organoboronic adds described in publications mentioned under that heading.

DETAILED DESCRIPTION OF SEVERAL EXAMPLES

Glossary

Figure 1:
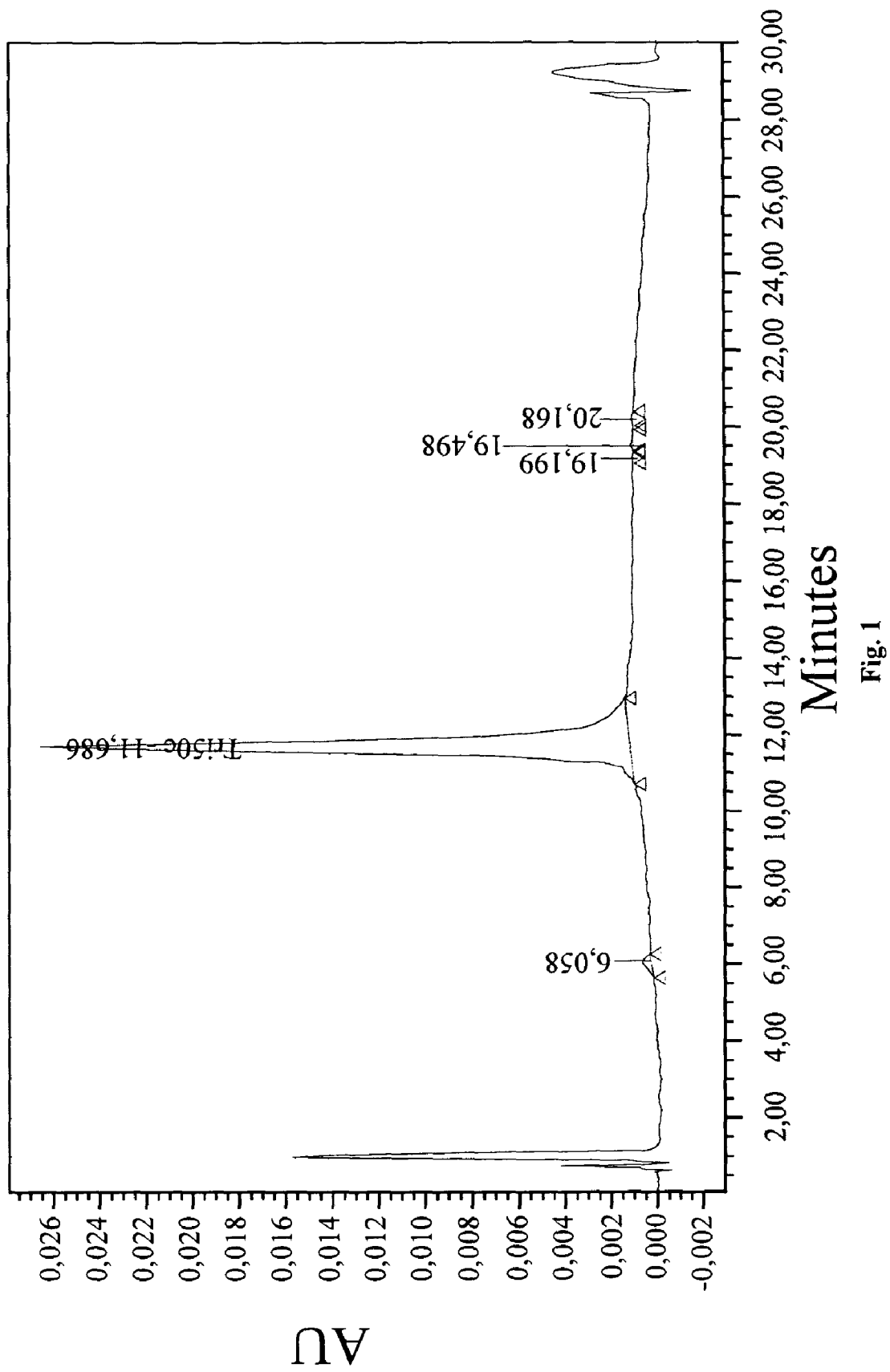
FIG. 1 is an HPLC plot referred to in Example 13, showing an impurity profile of encapsulated TRI 50c calcium salt after having been maintained in blister packaging for 1.5 month at 25° C. and 60% relative humidity.

The following terms and abbreviations are used in this specification:

The expression "acid salt" as applied to a salt of a boronic acid refers to salts of which a single —OH group of the trigonally-represented acid group —B(OH)$_2$ is deprotonated. Thus salts wherein the boronate group carries a single negative charge and may be represented as —B(OH)(O$^-$) or as [—B(OH)$_3$]$^-$ are acid salts. The expression encompasses salts of a metal having a valency n wherein the molar ratio of boronic acid to cation is approximately n to 1. In practical terms, the observed stoichiometry is unlikely to be exactly n:1 but will be consistent with a notional n:1 stoichiometry. For example, the observed mass of the metal might vary from the calculated mass for a n:1 stoichiometry by no more than about 10%, e.g. no more than about 7.5%; in some cases an observed mass of a metal might vary from the calculated mass by no more than about 1%. Calculated masses are suitably based on the trigonal form of the boronate. (At an atomic level, a salt stoichiometrically consistent with being an acid salt might contain boronates in a mix of protonation states, whose average approximates to single deprotonation and such "mixed" salts are included in the term "acid salt"). Examples of acid salts are hemimagnesium salts and hemicalcium salts.

α-Aminoboronic acid or Boro(aa) refers to an amino acid in which the CO$_2$ group has been replaced by BO$_2$.

The term "amino-group protecting moiety" refers to any group used to derivatise an amino group, especially an N-terminal amino group of a peptide or amino acid. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The expression "thrombin inhibitor" refers to a product which, within the scope of sound pharmacological judgement, is potentially or actually pharmaceutically useful as an inhibitor of thrombin, and includes reference to substance which comprises a pharmaceutically active species and is described, promoted or authorised as a thrombin inhibitor. Such thrombin inhibitors may be selective, that is they are regarded, within the scope of sound pharmacological judgement, as selective towards thrombin in contrast to other proteases; the term "selective thrombin inhibitor" includes reference to substance which comprises a pharmaceutically active species and is described, promoted or authorised as a selective thrombin inhibitor. The terms "protease inhibitor" and "selective protease inhibitor" have analogous meanings.

The term "heteroaryl" refers to a ring system which has at least one (e.g. 1, 2 or 3) in-ring heteroatoms and has a conjugated in-ring double bond system. The term "heteroatom" includes oxygen, sulfur and nitrogen, of which sulfur is sometimes less preferred.

"Natural amino acid" means an L-amino acid (or residue thereof) selected from the following group of neutral (hydrophobic or polar), positively charged and negatively charged amino acids:

Hydrophobic Amino Acids
A=Ala=alanine
V=Val=valine
I=Ile=isoleucine
L=Leu=leucine
M=Met=methionine
F=Phe=phenylalanine
P=Pro=proline
W=Trp=tryptophan
Polar (Neutral or Uncharged) Amino Acids
N=Asn=asparagine
C=Cys=cysteine
Q=Gln=glutamine
G=Gly=glycine
S=Ser=serine
T=Thr=threonine
Y=Tyr=tyrosine
Positively Charged (Basic) Amino Acids
R=Arg=arginine
H=His=histidine
K=Lys=lysine
Negatively Charged Amino Acids
D=Asp=aspartic acid
E=Glu=glutamic acid.
ACN=acetonitrile
Amino acid=α-amino acid
Cbz=benzyloxycarbonyl
Cha=cyclohexylalanine (a hydrophobic unnatural amino acid)
Charged (as applied to drugs or fragments of drug molecules, e.g. amino acid residues)=carrying a charge at physiological pH, as in the case of an amino, amidino or carboxy group
Dcha=dicyclohexylalanine (a hydrophobic unnatural amino acid)
Dpa=diphenylalanine (a hydrophobic unnatural amino acid)
Drug=a pharmaceutically useful substance, whether the active in vivo principle or a prodrug i.v.=intravenous
Mpg=3-methoxypropylglycine (a hydrophobic unnatural amino acid)
Multivalent=valency of at least two, for example two or three
Neutral (as applied to drugs or fragments of drug molecules, e.g. amino acid residues)=uncharged=not carrying a charge at physiological pH
Pinac=Pinacol=2,3-dimethyl-2,3-butanediol
Pinanediol=2,3-pinanediol=2,6,6-trimethylbicyclo [3.1.1] heptane-2,3-diol
Pip=pipecolinic acid
p.o.=per os=by way of the mouth (thus an oral formulation is administered p.o.)
s.c.=subcutaneous
THF=tetrahydrofuran
Thr=thrombin The Compounds The products of the disclosure comprise a salt of a pharmaceutically acceptable multivalent (at least divalent) metal and an organoboronic acid drug (where the term "drug" embraces prodrugs). As previously stated, the term "salt" refers to a product containing a multivalent metal and an organoboronate species, for example a product having the characteristics of a product of a reaction between an organoboronic acid and a base comprising a multivalent metal (for example a +2 ion); in particular, such characteristics comprise the identity of the multivalent metal and of the drug species.

One class of products comprises those salts which are acid salts. A second class of products comprises those salts which, whether or not acid, are salts of a boronic acid of formula III. A third class of products comprises all the salts in contexts relating to their oral administration, for example when present in oral formulations.

The acid may for example be any boronic acid drug mentioned under the heading "BACKGROUND" or in any document referred to under that heading, e.g. it may be TRI 50c or LDP-341. It may be a boronic acid described in WO 01/02424. In this paragraph, reference to a boronic acid described in the prior art includes reference to the free acids of boronate esters described in the prior art. It may be any other boronic acid drug.

In certain embodiments the organoboronic acid is hydrophobic.

Disclosed herein are embodiments in which the organoboronic acid comprises an aminoboronic acid linked through a peptide linkage to an organic moiety, which organic moiety may be hydrophobic. The organic moiety can comprise an amino acid whose C-terminal carboxy group forms part of said peptide linkage. The disclosure therefore includes salts of compounds of formula (XIII) and a multivalent, e.g. divalent, metal:

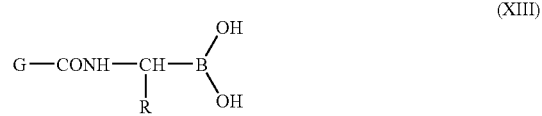

(XIII)

In formula (XII), G is an organic moiety, for example comprising together with —CO— a residue of an optionally N-terminally substituted amino acid or peptide (e.g. dipeptide), a suitable N-terminal substituent being for example an X group as described below. R is a side chain of an amino acid (whether natural or unnatural). G and R may be hydrophobic. R may be an $R^1$ group as described below.

One specific class of salts comprises those wherein the organoboronic acid comprises a boropeptide or boropeptidomimetic. For example, in a sub-class of these salts the organoboronic acid is of the formula (I):

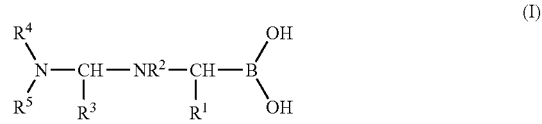

(I)

where:
$R^1$ is H or a non-charged side group;
$R^2$ is H or $C_1$–$C_{13}$ hydrocarbyl optionally containing in-chain oxygen or sulfur and optionally substituted by a substituent selected from halo, hydroxy and trifluoromethyl;
or $R^1$ and $R^2$ together form a $C_1$–$C_{13}$ moiety which in combination with N—CH forms a 4–6 membered ring and which is selected from alkylene (whether branched or linear) and alkylene containing an in-chain sulfur or linked to N—CH through a sulfur;

$R^3$ is the same as or different from $R^1$ provided that no more than one of $R^1$ and $R^2$ is H;

$R^4$ is H or a $C_1$–$C_{13}$ hydrocarbyl group optionally containing in-chain oxygen or sulfur and optionally substituted by a substituent selected from halo, hydroxy and trifluoromethyl;

or $R^3$ and $R^4$ together form a $C_1$–$C_{13}$ moiety which in combination with N—CH forms a 4–6 membered ring and which is selected from alkylene (whether branched or linear) and alkylene containing an in-chain sulfur or linked to N—CH through a sulfur; and $R^5$ is X-E- wherein E is nothing or a hydrophobic moiety selected from the group consisting of amino acids (natural or unnatural) and peptides of two or more amino acids (natural or unnatural) of which more than half are hydrophobic, in which peptides the nitrogen(s) of the peptide linkage(s) may be substituted by a $C_1$–$C_{13}$ hydrocarbyl optionally containing in-chain oxygen or sulfur and optionally substituted by a substituent selected from halo, hydroxy and trifluoromethyl (an example of such an N-substituent is 1C to 6C alkyl), and X is H or an amino-protecting group.

Said $C_1$–$C_{13}$ hydrocarbyl optionally containing in-chain oxygen or sulfur may be selected from alkyl; alkyl substituted by cycloalkyl, aryl or heterocyclyl; cycloalkyl; aryl; and/or heterocyclyl. Heterocyclyl may be heteroaryl.

$R^1$ may be non polar. In some embodiments, $R^1$ contains up to 20 carbon atoms. $R^1$ may have affinity for the S1 subsite of a protease.

In one class of compounds, $R^1$ is a moiety other than hydrogen selected from a group of formula A or B:

(A)

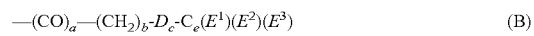
(B)

wherein
a is 0 or 1;
e is 1;
b and d are independently 0 or an integer such that (b+d) is from 0 to 4 or, as the case may be,
(b+e) is from 1 to 4;
c is 0 or 1;
D is O or S;
E is H, $C_1$–$C_6$ alkyl, or a saturated or unsaturated cyclic group which normally contains up to 14 members and particularly is a 5–6 membered ring (e.g. phenyl) or an 8–14 membered fused ring system (e.g. naphthyl), which alkyl or cyclic group is optionally substituted by up to 3 groups (e.g. 1 group) independently selected from $C_1$–$C_6$ trialkylsilyl, —CN, —$R^{13}$, —$R^{12}OR^{13}$, —$R^{12}COR^{13}$, —$R^{12}CO_2R^{13}$ and —$R^{12}O_2CR^{13}$, wherein $R^{12}$ is —$(CH_2)_f$— and $R^{13}$ is —$(CH_2)_gH$ or by a moiety whose non-hydrogen atoms consist of carbon atoms and in-ring heteroatoms and number from 5 to 14 and which contains a ring system (e.g. an aryl group) and optionally an alkyl and/or alkylene group, wherein f and g are each independently from 0 to 10, g particularly being at least 1 (although —OH may also be mentioned as a substituent), provided that (f+g) does not exceed 10, more particularly does not exceed 6 and most particularly is 1, 2, 3 or 4, and provided that there is only a single substituent if the substituent is a said moiety containing a ring system, or E is $C_1$–$C_6$ trialkylsilyl; and $E^1$, $E^2$ and $E^3$ are each independently selected from —$R^{15}$ and -J-$R^{15}$, where J is a 5–6 membered ring and $R^{15}$ is selected from $C_1$–$C_6$ trialkylsilyl, —CN, —$R^{13}$, —$R^{12}OR^{13}$, —$R^{12}COR^{13}$, —$R^{12}CO_2R^{13}$, —$R^{12}O_2CR^{13}$, and one or two halogens (e.g. in the latter case to form a -J-$R^{15}$ moiety which is dichlorophenyl), where $R^{12}$ and $R^{13}$ are, respectively, an $R^{12}$ moiety and an $R^{13}$ moiety as defined above (in some acids where $E^1$, $E^2$ and $E^3$ contain an $R^{13}$ group, g is 0 or 1);

in which moiety of Formula (A) or (B) any ring is carbocyclic or aromatic, or both, and any one or more hydrogen atoms bonded to a carbon atom is optionally replaced by halogen, especially F.

In certain examples, a is 0. If a is 1, c may be 0. In particular examples, (a+b+c+d) and (a+b+c+e) are no more than 4 and are more especially 1, 2 or 3. (a+b+c+d) may be 0.

Exemplary groups for E, $E^1$, $E^2$ and $E^3$ include aromatic rings such as phenyl, naphthyl, pyridyl, quinolinyl and furanyl, for example; non-aromatic unsaturated rings, for example cyclohexenyl; saturated rings such as cyclohexyl, for example. E may be a fused ring system containing both aromatic and non-aromatic rings, for example fluorenyl. One class of E, $E^1$, $E^2$ and $E^3$ groups are aromatic (including heteroaromatic) rings, especially 6-membered aromatic rings. In some compounds, $E^1$ is H whilst $E^2$ and $E^3$ are not H; in those compounds, examples of $E^2$ and $E^3$ groups are phenyl (substituted or unsubstituted) and $C_1$–$C_4$ alkyl, e.g. methyl.

In one class of embodiments, E contains a substituent which is $C_1$–$C_6$ alkyl, ($C_1$–$C_5$ alkyl)carbonyl, carboxy $C_1$–$C_5$ alkyl, aryl (including heteroaryl), especially 5-membered or preferably 6-membered aryl (e.g. phenyl or pyridyl), or arylalkyl (e.g. arylmethyl or arylethyl where aryl may be heterocyclic and is preferably 6-membered).

In another class of embodiments, E contains a substituent which is $OR^{13}$, wherein $R^{13}$ can be a 6-membered ring, which may be aromatic (e.g. phenyl) or is alkyl (e.g. methyl or ethyl) substituted by such a 6-membered ring.

A class of moieties of formula A or B are those in which E is a 6-membered aromatic ring optionally substituted, particularly at the 2-position or 4-position, by —$R^{13}$ or —$OR^{13}$.

The disclosure also includes salts in which $R^1$ comprises a cyclic group in which 1 or 2 hydrogens have been replaced by halogen, e.g. F or Cl.

The disclosure further includes a class of salts in which the $R^1$ groups of formula (A) or (B) are of the following formulae (C), (D) or (E):

$C_qH_{2q}CHT_2$ (C)

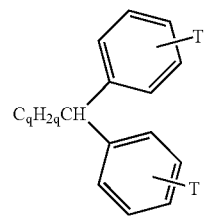
(D)

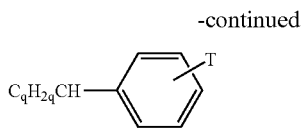

wherein q is from 0 to 5, e.g. is 0, 1 or 2, and each T is independently hydrogen, one or two halogens (e.g. F or Cl), —SiMe$_3$, —CN, —R$^{13}$, —OR$^{13}$, —COR$^{13}$, —CO$_2$R$^{13}$ or —O$_2$CR$^{13}$. In some embodiments of structures (D) and (E), T is at the 4-position of the phenyl group(s) and is —R$^{13}$, —OR$^{13}$, —COR$^{13}$, —CO$_2$R$^{13}$ or —O$_2$CR$^{13}$, and R$^{13}$ is C$_1$–C$_{10}$ alkyl and more particularly C$_1$–C$_6$ alkyl. In one sub-class, T is —R$^{13}$ or —OR$^{13}$, for example in which f and g are each independently 0, 1, 2 or 3; in some R$^1$ groups of this sub-class, T is —R$^{12}$OR$^{13}$ and R$^{13}$ is H.

In one class of the moieties, R$^1$ is of formula (C) and each T is independently R$^{13}$ or OR$^{13}$ and R$^{13}$ is C$_1$–C$_4$ alkyl. In some of these compounds, R$^{13}$ is branched alkyl and in others it is straight chain. In some moieties, the number of carbon atoms is from 1 to 4. In another class of moieties, R$^1$ is of formula (E) and T is —CN or one or two halogens; in these compounds, q may be 0 or 1, for example.

One class of compounds have R$^2$ as H and R$^3$ as not H. Where R$^3$ is not H, it is preferably conjoined with R$^4$ to form a said moiety. Where R$^3$ is H, R$^4$ is preferably a said hydrocarbyl group, for example a C$_4$–C$_6$ hydrocarbyl group comprising a C$_5$–C$_6$ hydrocarbyl ring; the hydrocarbyl group may be saturated, for example an exemplary R$^4$ group for these compounds is cyclopentyl.

In particular examples, R$^4$ is H or R$^3$ and R$^4$ together form a said C$_1$–C$_{13}$ moiety.

Where R$^3$ does not join together with R$^4$ to form a said C$_1$–C$_{13}$ moiety, in some embodiments it contains up to 20 carbon atoms.

R$^3$ may be a group of formula (A) or (B) as defined above, for example a group of formula (C), (D) or (E). In one class of compounds, R$^3$ is of formula (C).

In one class of salts E is nothing.

In another class, E is comprises a sequence of one or more hydrophobic amino acids, for example such hydrophobic amino acids may have a side chain having up to 20 carbon atoms. In some compounds, E comprises a sequence of one or more hydrophobic amino acids (e.g. 1 amino acid) each of which has a side chain of formula (A) or (B) as defined above, e.g. a group of formula (C), (D) or (E), or is an imino acid, for example of the type formed when R$^1$ and R$^2$ of Formula (I) are joined together. In one class of salts, E consists of an amino acid having a side chain of formula (D); In another class of salts, E consists of an amino acid having a side chain is of formula (E).

One specific class of salts comprises those in which the organoboronic acid is of the formula (II):

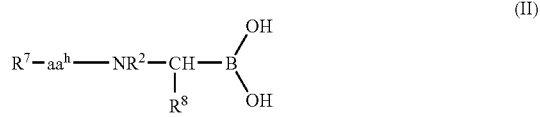

wherein
R$^7$ is X-E'- wherein X is hydrogen or an amino-protecting group and E' is absent or is a hydrophobic amino acid;

R$^8$ is an optionally substituted moiety containing from 1 to 5 carbon atoms selected from the group consisting of alkyl, alkoxy and alkoxyalkyl, the optional substituents being hydroxy or, preferably, halogen (F, Cl, Br, I) and the alkyl moieties being branched or straight chain; and aa$^h$ is a hydrophobic amino acid, or is glycine N-substituted by a C$_1$–C$_{13}$ hydrocarbyl group optionally containing in-chain oxygen or sulfur and optionally substituted by a substituent selected from halo, hydroxy and trifluoromethyl.

R$^7$ may be X—, or X-Phe or X-Dpa.

R$^8$ is preferably not substituted. R$^8$ is preferably a C$_4$ group, e.g. alkyl or alkoxyalkyl, such as 2-methylpropyl or 3-methoxypropyl, for example. In variants of Formula (II), R$^8$ is phenyl or benzyl, in either case optionally substituted by —CN or by one or two halogens (e.g. chlorine).

When aa$^h$ is N-substituted glycine, the N-substituent is for example a C$_3$–C$_6$ hydrocarbyl group comprising a C$_3$–C$_6$ hydrocarbyl ring; the hydrocarbyl group may be saturated, for example an exemplary R$^4$ group for these compounds is cycloalkyl, e.g. cyclopentyl.

The hydrophobic amino acids may be the same or different and for example be selected from amino acids having a side chain of formula (A) or (B) as defined above, e.g. of formula (C), (D) or (E), and from imino acids as described previously. The disclosure includes a class of salts wherein the organoboronic acid is of formula (II) and the hydrophobic amino acids, being the same or different, have a side chain containing up to 20 carbon atoms and often containing up to 13 carbon atoms or are imino acids. The hydrophobic amino acids may have a side chain as described previously for hydrophobic amino adds contained in the fragment X-E of Formula (I). In a subset of salts containing formula (II) acids, the hydrophobic amino acid is hydrocarbyl or heteroaryl, or which includes both hydrocarbyl and heteroaryl residues. The hydrocarbyl residues optionally contain in-chain oxygen; they may be substituted by, for example, halogen (e.g. 1, 2 or 3 halogen atoms) or hydroxy (but usually not more than one hydroxy group). Alternatively, hydrophobic amino acids may be proline or another imino acid.

In certain variants, R$^7$ contains a hydrophobic amino acid which is not Pro or another imino acid. In such embodiments, the hydrophobic amino acid of R$^7$ suitably has a side chain of formula (A) or (B) described previously [e.g. of formula (D) or (E)].

aa$^h$ may for example be a natural hydrophobic amino acid, e.g. Pro or Phe.

In certain examples X is R$^6$—(CH$_2$)$_p$—C(O)—, R$^6$—(CH$_2$)$_p$—S(O)$_2$—, R$^6$—(CH$_2$)$_p$—NH—C(O)— or R$^6$—(CH$_2$)$_p$—O—C(O)— wherein p is 0, 1, 2, 3, 4, 5 or 6 (of which 0 and 1 are preferred) and R$^6$ is H or a 5 to 13-membered cyclic group optionally substituted by 1, 2 or 3 substituents selected from halogen, amino, nitro, hydroxy, a C$_5$–C$_6$ cyclic group, C$_1$–C$_4$ alkyl and C$_1$–C$_4$ alkyl containing, and/or linked to the 5 to 13-membered cyclic group through, an in-chain O, the aforesaid alkyl groups optionally being substituted by a substituent selected from halogen, amino, nitro, hydroxy and a C$_5$–C$_6$ cyclic group. More particularly X is R$^6$—(CH$_2$)$_p$—C(O)— or R$^6$—(CH$_2$)$_p$—O—C(O)— and p is 0 or 1. Said 5 to 13-membered cyclic group is often aromatic or heteroaromatic, for example is a 6-membered aromatic or heteroaromatic group. In many cases, the group is not substituted.

Exemplary X groups are (2-pyrazine) carbonyl, (2-pyrazine) sulfonyl and benzyloxycarbonyl.

The organoboronic acid may be a protease inhibitor, for example a serine protease inhibitor. Thus the disclosure includes salts of a multivalent metal and an organoboronic acid inhibitor of a coagulation serine protease, for example thrombin or Factor Xa. As examples of such organoboronic acids may be mentioned peptide boronates, particularly dipeptides and tripeptides, which in either case may have a protecting group (a non-hydrogen X group) on the N-terminal amino moiety.

In a preferred class of boronic acids, which are anti-thrombotic and include TRI 50c, the acid has a neutral moiety capable of binding to the thrombin S subsite linked to a hydrophobic moiety capable of binding to the thrombin S2 and S3 subsites. The acid may for example be of formula (III):

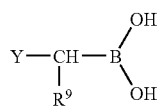
(III)

wherein

Y comprises a moiety which, together with the fragment —CH($R^9$)—B(OH)$_2$, has affinity for the substrate binding site of thrombin; and $R^9$ is a straight chain alkyl group interrupted by one or more ether linkages (e.g. 1 or 2) and in which the total number of oxygen and carbon atoms is 3, 4, 5 or 6 (e.g. 5) or $R^9$ is —(CH$_2$)$_m$—W where m is 2, 3, 4 or 5 (e.g. 4) and W is —OH or halogen (F, Cl, Br or I). As examples of straight chain alkyl interrupted by one or more ether linkages (—O—) may be mentioned alkoxyalkyl (one interruption) and alkoxyalkoxyalkyl (two interruptions). $R^9$ is an alkoxyalkyl group in one subset of compounds, e.g. alkoxyalkyl containing 4 carbon atoms.

In a class of boronic acids, Y is linked to —CH(R9)—B(OH)$_2$ by a peptide linkage. Such acids may be represented by formula (XII):

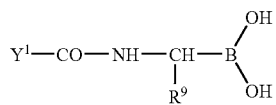
(XII)

wherein $Y^1$ comprises a hydrophobic moiety which, together with the aminoboronic acid residue —NHCH($R^9$)—B(OH)$_2$, has affinity for the substrate binding site of thrombin and $R^9$ is as defined above.

Typically, therefore, the moiety represented by symbol Y in formula (III) comprises an amino acid residue (whether natural or unnatural) which binds to the S2 subsite of thrombin and is linked to the fragment —CH($R^9$)—B(OH)$_2$ by a peptide linkage, the amino acid residue being N-terminally linked to a moiety which binds the S3 subsite of thrombin.

In one class of Formula (III) acids, Y is an optionally N-terminally protected dipeptide residue which binds to the S3 and S2 binding sites of thrombin and is linked to —CH(R9)—B(OH)$_2$ by a peptide linkage, the peptide linkages in the acid optionally and independently being N-substituted by a $C_1$–$C_{13}$ hydrocarbyl optionally containing in-chain oxygen or sulfur and optionally substituted by a substituent selected from halo, hydroxy and trifluoromethyl.

The N-terminal protecting group, when present, may be a group X as defined above (other than hydrogen). Normally, the acid contains no N-substituted peptide linkages; where there is an N-substituted peptide linkage, the substituent is often 1C to 6C alkyl. One class of acids has an N-terminal protecting group (e.g. an X group) and unsubstituted peptide linkages.

Where Y is a dipeptide residue, the S3-binding amino acid residue may be of (R)-configuration and/or the S2-binding residue may of (S)-configuration. The fragment —NHCH($R^9$)—B(OH) may of (R)-configuration. The disclosure is not restricted to chiral centres of these conformations, however.

The disclosure therefore includes medicaments comprising salts, e.g. metal salts, of organoboronic acids which are thrombin inhibitors, particularly selective thrombin inhibitors, having a neutral P1 (S1-binding) moiety. For more information about moieties which bind to the S3, S2 and S1 sites of thrombin, see for example Tapparelli C et al, *Trends Pharmacol. Sci.* 14: 366–376, 1993; Sanderson P et al, *Current Medicinal Chemistry*, 5: 289–304, 1998; Rewinkel J et al, *Current Pharmaceutical Design*, 5:1043–1075, 1999; and Coburn C *Exp. Opin. Ther. Patents* 11(5): 721–738, 2001. The thrombin inhibitory salts of the disclosure are not limited to those having S3, S2 and S1 affinity groups described in the publications listed in the preceding sentence.

The organoboronic acids which are thrombin inhibitors, for example the acids of formula (III), may have a Ki for thrombin of about 100 nM or less, e.g. about 20 nM or less.

A subset of the Formula (III) acids comprises the acids of Formula (IV):

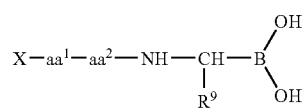
(IV)

X is a moiety bonded to the N-terminal amino group and may be H to form NH$_2$. The identity of X is not critical but may be a particular X moiety described above. In one example there may be mentioned benzyloxycarbonyl.

$aa^1$ is an amino acid residue having a hydrocarbyl side chain containing no more than 20 carbon atoms (e.g. up to 15 and optionally up to 13 C atoms) and comprising at least one cyclic group having up to 13 carbon atoms. In certain examples, the cyclic group(s) of $aa^1$ have/has 5 or 6 ring members. For instance, the cyclic group(s) of $aa^1$ may be aryl groups, particularly phenyl. Typically, there are one or two cyclic groups in the $aa^1$ side chain. Certain side chains comprise, or consist of, methyl substituted by one or two 5- or 6-membered rings.

More particularly, $aa^1$ is Phe, Dpa or a wholly or partially hydrogenated analogue thereof. The wholly hydrogenated analogues are Cha and Dcha.

$aa^2$ is an imino acid residue having from 4 to 6 ring members. Alternatively, $aa^2$ is Gly N-substituted by a $C_3$–$C_{13}$ hydrocarbyl group, e.g. a $C_3$–$C_8$ hydrocarbyl group comprising a $C_3$–$C_6$ hydrocarbyl ring; the hydrocarbyl group may be saturated, for example exemplary N-substituents are cyclopropyl, cyclobutyl, cyclopentyl and cyclohexyl. As a hydrocarbyl group containing one or more unsaturated bonds may be mentioned phenyl and methyl or ethyl substituted by phenyl, e.g. 2-phenylethyl, as well as β,β-dialkylphenylethyl.

An exemplary class of products comprises those in which aa² is a residue of an imino acid of formula (V)

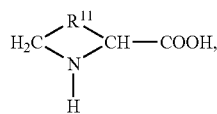

where $R^{11}$ is —$CH_2$—, $CH_2$—$CH_2$—, —S—$CH_2$— or —$CH_2$—$CH_2$—$CH_2$—, which group when the ring is 5 or 6-membered is optionally substituted at one or more —$CH_2$— groups by from 1 to 3 $C_1$-$C_3$ alkyl groups, for example to form the $R^{11}$ group —S—$C(CH_3)_2$—. Of these imino acids, azetidine-2-carboxylic acid, especially (s)-azetidine-2-carboxylic acid, and more particularly proline are illustrative.

It will be appreciated from the above that a very preferred class of products consists of those in which aa¹-aa² is Phe-Pro. In another preferred class, aa¹-aa² is Dpa-Pro. In other products, aa¹-aa² is Cha-Pro or Dcha-Pro. Of course, also included are corresponding product classes in which Pro is replaced by (s)-azetidine-2-carboxylic acid.

$R^9$ is as defined in relation to formula (III). In one class of compounds [whether of formula (III) or formula (IV)], $R^9$ is a group of the formula —$(CH_2)_s$-Z. Integer s is 2, 3 or 4 and Z is —OH, —OMe, —OEt or halogen (F, Cl, I or, preferably, Br). Particularly illustrative Z groups are —OMe and —OEt, especially —OMe. In certain examples s is 3 for all Z groups and, indeed, for all formula (III) or (IV) compounds. Particular $R^9$ groups are 2-bromoethyl, 2-chloroethyl, 2-methoxyethyl, 4-bromobutyl, 4-chlorobutyl, 4-methoxybutyl and, especially, 3-bromopropyl, 3-chloropropyl and 3-methoxypropyl. In a specific example, $R^9$ is 3-methoxypropyl. In another example, 2-Ethoxyethyl is the preferred $R^9$ group.

Accordingly, a specific class of salts consists of those of acids of the formula X-Phe-Pro-Mpg-B(OH)₂, especially Cbz-Phe-Pro-Mpg-B(OH)₂; also included are analogues of these compounds in which Mpg is replaced by a residue with another of the $R^9$ groups and/or Phe is replaced by Dpa or another aa¹ residue.

The aa¹ moiety of the salt is preferably of (R)-configuration. The aa² moiety is preferably of (S)-configuration. Particularly preferred salts have aa¹ of (R)-configuration and aa² of (S)-configuration. The chiral centre —NH—CH($R^1$)—B— is preferably of (R)-configuration. It is considered that commercial formulations will have the chiral centres in (R,S,R) arrangement, as for example in the case of salts of

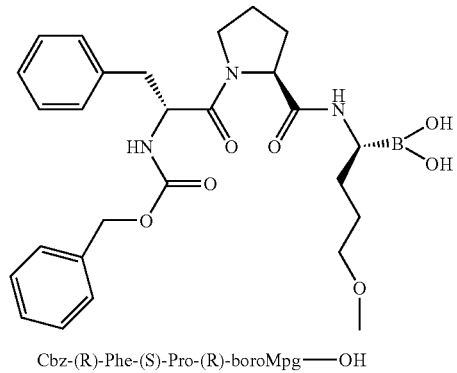

Cbz-(R)-Phe-(S)-Pro-(R)-boroMpg—OH

The disclosure includes multivalent metal salts of Cbz-(R)-Phe-(S)-Pro-(R)-boroMpg-OH (and of other compounds of the formula X-(R)-Phe-(S)-Pro-(R)-boroMpg-OH) which are at least 90% pure, e.g. at least 95% pure.

In broad terms, the salts described herein may be considered to correspond to reaction products of an organoboronic acid as described above with a base of a multivalent metal, i.e. a metal having a valency of two or more; the salts are however not limited to products resulting from such a reaction and may be obtained by alternative routes. The metal is especially:
1. a Group II metal (alkaline earth metal);
2. another pharmaceutically acceptable divalent metal, e.g. zinc; or
3. a Group III metal.

One exemplary class of salts comprises divalent metal salts. A particularly illustrative class of salts comprises the calcium salts. Another particularly illustrative class of salts comprises the magnesium salts. A further class of salts comprises the zinc salts.

Specific salts are of the acid boronate though in practice the add salts may contain a very small proportion of the doubly deprotonated boronate. The term "acid boronate" refers to trigonal —B(OH)₂ groups in which one of the B—OH groups is deprotonated as well as to corresponding tetrahedral groups in equilibrium therewith. Acid boronates have a stoichiometry consistent with single deprotonation.

The disclosure further includes therefore products (compositions of matter) which comprise salts which may be represented by formula (VI):

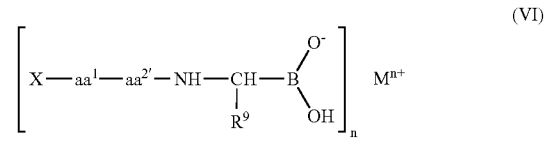

where $M^{n+}$ is a divalent or trivalent metal cation, aa²' is a residue of an imino acid of formula V, n is 2 or 3 as the case may be, and aa¹, X and $R^9$ are as defined above. As previously indicated, the boronate may comprise a tetrahedral species. Accordingly, illustrative products have a stoichiometry consistent with the above formula.

The disclosure additionally includes calcium and magnesium salts of boronic acid drugs having an observed stoichiometry consistent with the salt being of (being representable by) the formula "(boronate⁻)₂ $Ca^{2+}$" or "(boronate⁻)₂ $Mg^{2+}$". In other salts of this type, the metal is zinc. One class of salts having such stoichiometry comprises salts of boronic acids of formula (IV), as for example in the case of a salt of the formula:

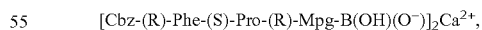

[Cbz-(R)-Phe-(S)-Pro-(R)-Mpg-B(OH)(O⁻)]₂Ca²⁺, such salt being designated TGN 167. The disclosure includes salts of the above formula in which Ca²⁺ is replaced by Mg²⁺. Also included are corresponding zinc salts. It will be understood that the above representation is a notional representation of a product whose observed stoichiometry is unlikely to be literally and exactly 2:1. In the above formula, the trigonally-represented boronate represents boronates which are trigonal, tetrahedral or mixed trigonal/tetrahedral.

Particularly exemplary are products which comprise:
(i) species selected from (a) acids of formula (IX): X—(R)-Phe-(S)-Pro-(R)-Mpg-B(OH)₂ where X is H or an amino-protecting group, especially Cbz, (b) boronate anions thereof, and (c) any equilibrium form of the aforegoing (e.g. an anhydride); and
(ii) divalent metal ions, particularly calcium ions, in combination with said species, the species and the metal ions having an observed stoichiometry consistent with a notional species:metal stoichiometry of 2:1.

Considering the metals in turn:

1. Divalent. e.g. Alkaline Earth Metal (Group II Metal) Salts

One example of a divalent metal is calcium. Another suitable divalent metal is magnesium. Also contemplated is zinc. The divalent metals are usually used in a boronic acid:metal ratio of substantially 2:1, in order to achieve the preferred monovalent boronate moiety. Salts containing mixtures of divalent metals, e.g. mixtures of alkaline earth metals, are also contemplated.

Further disclosed are products (compositions of matter) which comprise salts which may be represented by the formula (VII):

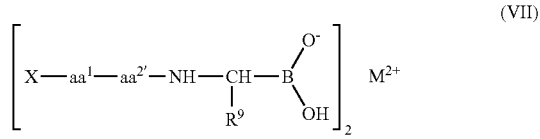

(VII)

where $M^{2+}$ is a divalent metal cation, e.g. an alkaline earth metal or zinc cation, and $aa^1$, $aa^{2'}$, X and $R^9$ are as defined above, as well as salts in which both hydroxy groups of the boronate group are deprotonated and mixtures of such salts. As previously indicated, the boronate may comprise a tetrahedral species.

2. Group III Metals

Suitable Group III metals include aluminium and gallium. Salts containing mixtures of Group III metals are also contemplated.

The disclosure includes products comprising salts of the formula (VIII):

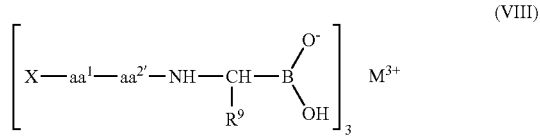

(VIII)

where $M^{3+}$ is a Group III metal ion and $aa^1$, $aa^{2'}$, X and $R^9$ are as defined above, as well as salts in which both hydroxy groups of the boronate group are in salt form and mixtures of such salts. As previously indicated, the boronate may comprise a tetrahedral species.

The salts in solid form may contain a solvent, e.g. water. There are included a class of products in which the salts are essentially anhydrous. Also included is a class in which the salts are hydrates.

Use of the Products of the Disclosure

The salts are useful for formulations, especially for oral formulations, for administering the drug part of the salt. Typically, they are useful as protease inhibitors.

The Salts of Thrombin Inhibitors

As described above, disclosed herein are salts of boronic acids which are thrombin inhibitors. For example, the salts of the boronic acids of formula (IV) are potent thrombin inhibitors. They are therefore useful for inhibiting thrombin. The disclosure therefore provides thrombin inhibitory compounds which have potential for controlling haemostasis and especially for inhibiting coagulation, for example in the treatment or prevention of secondary events after myocardial infarction. The medical use of the compounds may be prophylactic (including to treat thombosis as well as to prevent occurrence of thrombosis) as well as therapeutic (including to prevent re-occurrence of thrombosis or secondary thrombotic events).

The thrombin inhibitory salts may be employed when an anti-thrombogenic agent is needed. Further, it has been found that these salts are beneficial in that the class is useful for treating arterial thrombosis by therapy or prophylaxis. The disclosed thrombin inhibiting salts are thus indicated in the treatment or prophylaxis of thrombosis and hypercoagulability in blood and tissues of animals including man. The term "thrombosis" includes inter alia atrophic thrombosis, arterial thrombosis, cardiac thrombosis, coronary thrombosis, creeping thrombosis, infective thrombosis, mesenteric thrombosis, placental thrombosis, propagating thrombosis, traumatic thrombosis and venous thrombosis.

It is known that hypercoagulability may lead to thromboembolic diseases.

Examples of venous thromboembolism which may be treated or prevented with compounds of the disclosure include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the disclosure are useful for maintaining patency of indwelling catheters.

Examples of cardiogenic thromboembolism which may be treated or prevented with compounds of the disclosure include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of conditions involving arterial thrombosis include unstable angina (severe constrictive pain in chest of coronary origin), myocardial infarction (heart muscle cell death resulting from insufficient blood supply), ischemic heart disease (local ischemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterio-venous (mixed) thrombosis, anti-thrombotic compounds of the disclosure are useful for maintaining patency in arteriovenous shunts.

Other conditions associated with hypercoagulability and thromboembolic diseases which may be mentioned inherited or acquired deficiencies in heparin cofactor II, circulating antiphospholipid antibodies (Lupus anticoagulant), homocysteinemia, heparin induced thrombocytopenia and defects in fibrinolysis.

Particular uses which may be mentioned include the therapeutic and/or prophylactic treatment of venous thrombosis and pulmonary embolism. Preferred indications envisaged for the anti-thrombotic products of the disclosure (notably the salts of the boronic acids of formula IV, for example the salts of TRI 50c) include:

Prevention of venous thromboembolic events (e.g. deep vein thrombosis and/or pulmonary embolism). Examples include patients undergoing orthopaedic surgery such as total hip replacement, total knee replacement, major hip or knee surgery; patients undergoing general surgery at high risk for thrombosis, such as abdominal or pelvic surgery for cancer; and in patients bedridden for more than 3 days and with acute cardiac failure, acute respiratory failure, infection.

Prevention of thrombosis in the haemodialysis circuit in patients, in patients with end stage renal disease.

Prevention of cardiovascular events (death, myocardial infarction, etc) in patients with end stage renal disease, whether or not requiring haemodialysis sessions.

Prevention of venous thrombo-embolic events in patients receiving chemotherapy through an indwelling catheter.

Prevention of thromboembolic events in patients undergoing lower limb arterial reconstructive procedures (bypass, endarteriectomy, transluminal angioplasty, etc).

Treatment of venous thromboembolic events.

Prevention of cardiovascular events in acute coronary syndromes (e.g. unstable angina, non Q wave myocardial ischaemia/infarction), in combination with another cardiovascular agent, for example aspirin (acetylsalicylic acid; aspirin is a registered trade mark in Germany), thrombolytics (see below for examples), anti-platelet agents (see below for examples).

Treatment of patients with acute myocardial infarction in combination with acetylsalicylic acid, thrombolytics (see below for examples).

The presently disclosed thrombin inhibitors are thus indicated both in the therapeutic and/or prophylactic treatment of all the aforesaid disorders.

In one method, the presently disclosed thrombin inhibitors are used for the treatment of patients by haemodialysis, by providing the product in the dialysis solution, as described in relation to other thrombin inhibitors in WO 00/41715. The present disclosure therefore includes dialysing solutions and dialysing concentrates which comprise the presently disclosed anti-thrombotic product, as well as a method of treatment by dialysis of a patient in need of such treatment, which method comprises the use of a dialysing solution including a low molecular weight thrombin inhibitor. Also included is the use of an anti-thrombotic product of the disclosure for the manufacture of a medicament for the treatment by dialysis of a patient, in which the anti-thrombotic product of the disclosure is provided in the dialysing solution.

In another method, the presently disclosed thrombin inhibitors are used to combat undesirable cell proliferation, as described in relation to other thrombin inhibitors in WO 01/41796. The undesirable cell proliferation is typically undesirable hyperplastic cell proliferation, for example proliferation of smooth muscle cells, especially vascular smooth muscle cells. The thrombin inhibitors particularly find application in the treatment of intimal hyperplasia, one component of which is proliferation of smooth muscle cells. Restenosis can be considered to be due to neointimal hyperplasia; accordingly intimal hyperplasia in the present context includes restenosis.

The thrombin inhibitors are also contemplated for the treatment of ischemic disorders. More particularly, they may be used in the treatment (whether therapeutic or prophylactic) of an ischemic disorder in a patient having, or at risk of, non-valvular atrial fibrillation (NVAF) as described in relation to other thrombin inhibitors in WO 02/36157. Ischemic disorders are conditions whose results include a restriction in blood flow to a part of the body. The term will be understood to include thrombosis and hypercoagulability in blood, tissues and/or organs. Particular uses that may be mentioned include the prevention and/or treatment of ischemic heart disease, myocardial infarction, systemic embolic events in e.g. the kidneys or spleen, and more particularly of cerebral ischemia, including cerebral thrombosis, cerebral embolism and/or cerebral ischemia associated with non-cerebral thrombosis or embolism (in other words the treatment (whether therapeutic or prophylactic) of thrombotic or ischemic stroke and of transient ischemic attack), particularly in patients with, or at risk of, NVAF.

The thrombin inhibitors are also contemplated for the treatment of rheumatic/arthritic disorders, as described in relation to other thrombin inhibitors in WO 03/007984. Thus, a thrombin inhibitory salt may be used in the treatment of chronic arthritis, rheumatoid arthritis, osteoarthritis or ankylosing spondylitis Moreover, the thrombin inhibitors of the disclosure are expected to have utility in prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general. Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

The thrombin inhibitors are further indicated in the treatment of conditions where there is an undesirable excess of thrombin without signs of hypercoagulability, for example in neurodegenerative diseases such as Alzheimer's disease. In addition to its effects on the coagulation process, thrombin is known to activate a large number of cells (such as neutrophils, fibroblasts, endothelial cells and smooth muscle cells). Therefore, the presently disclosed compounds may also be useful for the therapeutic and/or prophylactic treatment of idiopathic and adult respiratory distress syndrome, pulmonary fibrosis following treatment with radiation or chemotherapy, septic shock, septicaemia, inflammatory responses, which include, but are not limited to, edema, acute or chronic atherosclerosis such as coronary arterial disease, cerebral arterial disease, peripheral arterial disease, reperfusion damage, and restenosis after percutaneous transluminal angioplasty (PTA).

The thrombin inhibitory salts may also be useful in the treatment of pancreatitis.

The salts of the boronic acids of formula (III) are further considered to be useful for inhibiting platelet procoagulant activity. Also provided is a method for inhibiting platelet pro-coagulant activity by administering a salt of a formula (III) or formula (IV) boronic acid to a mammal at risk of, or suffering from, arterial thrombosis, particularly a human patient. Further provided is the use of such salts for the manufacture of medicaments for inhibiting platelet procoagulant activity.

The use of the formula (III) or formula (IV) products as inhibitors of platelet pro-coagulant activity is predicated on the observation that the formula (III) or formula (IV) acids are effective at inhibiting arterial thrombosis as well as venous thrombosis.

Indications involving arterial thrombosis include acute coronary syndromes (especially myocardial infarction and unstable angina), cerebrovascular thrombosis and peripheral arterial occlusion and arterial thrombosis occurring as a result of atrial fibrillation, valvular heart disease, arteriovenous shunts, indwelling catheters or coronary stents. Accordingly, in another aspect, there is provided a method of treating a disease or condition selected from this group of indications, comprising administering to a mammal, especially a human patient, a thrombin inhibitory salt according to the present disclosure. The disclosure includes products for use in an arterial environment, e.g. a coronary stent or other arterial implant, having a coating which comprises an antithrombin salt according to the present disclosure.

The salts of the formula (III) or formula (IV) boronic acids may be used prophylactically to treat an individual believed to be at risk of suffering from arterial thrombosis or a condition or disease involving arterial thrombosis or therapeutically (including to prevent re-occurrence of thrombosis or secondary thrombotic events).

The disclosure therefore includes the use of selective thrombin inhibitors (organoboronic acid salts) described herein for treatment of the above disorders by prophylaxis or therapy as well as their use in pharmaceutical formulations and the manufacture of pharmaceutical formulations.

In the case of those uses described above which are anti-coagulant in nature, there may be used in place of a thrombin inhibitor of the disclosure another anti-coagulant salt of the disclosure.

Administration and Pharmaceutical Formulations

The salts may be administered to a host, for example, in the case where the drug has anti-thrombogenic activity, to obtain an anti-thrombogenic effect. In the case of larger animals, such as humans, the salts may be administered alone or in combination with pharmaceutically acceptable diluents, excipients or carriers. The term "pharmaceutically acceptable" includes acceptability for both human and veterinary purposes, of which acceptability for human pharmaceutical use is preferred. In the case of oral administration, the compounds, particularly the salts of amino- or peptido-boronic acids, are preferably administered in a form which prevents the salt from contact with the acidic gastric juice, such as enterically coated formulations, which thus prevent release of the salt until it reaches the duodenum.

The enteric coating is suitably made of carbohydrate polymers or polyvinyl polymers, for example. Examples of enteric coating materials include, but are not limited to, cellulose acetate phthalate, cellulose acetate succinate, cellulose hydrogen phthalate, cellulose acetate trimellitate, ethyl cellulose, hydroxypropyl-methylcellulose phthalate, hydroxypropylmethylcellulose acetate succinate, carboxymethyl ethylcellulose, starch acetate phthalate, amylose acetate phthalate, polyvinyl acetate phthalate, polyvinyl butyrate phthalate, styrene-maleic acid copolymer, methylacrylate-methacrylic acid copolymer (MPM-05), methylacrylate-methacrylic acid-methylmethacrylate copolymer (MPM-06), and methylmethacrylate-methacrylic acid copolymer (Eudragit® L & S). Optionally, the enteric coating contains a plasticiser. Examples of the plasticiser include, but are not limited to, triethyl citrate, triacetin, and diethyl phthalate.

The presently disclosed anti-thrombotic salts may be combined and/or co-administered with any cardiovascular treatment agent. There are large numbers of cardiovascular treatment agents available in commercial use, in clinical evaluation and in pre-clinical development, which could be selected for use with the presently disclosed product for the prevention of cardiovascular disorders by combination drug therapy. Such agent can be one or more agents selected from, but not limited to several major categories, namely, a lipid-lowering drug, including an IBAT (ileal $Na^+$/bile acid cotransporter) inhibitor, a fibrate, niacin, a statin, a CETP (cholesteryl ester transfer protein) inhibitor, and a bile acid sequestrant, an anti-oxidant, including vitamin E and probucol, a IIb/IIIa antagonist (e.g. abciximab, eptifibatide, tirofiban), an aldosterone inhibitor (e.g. spirolactone and epoxymexrenone), an adenosine A2 receptor antagonist (e.g. losartan), an adenosine A3 receptor agonist, a beta-blocker, acetylsalicylic acid, a loop diuretic and an ACE (angiotensin converting enzyme) inhibitor.

The anti-thrombotic salts may be combined and/or co-administered with any antithrombotic agent with a different mechanism of action, such as the antiplatelet agents acetylsalicylic acid, ticlopidine, clopidogrel, thromboxane receptor and/or synthetase inhibitors, prostacyclin mimetics and phosphodiesterase inhibitors and ADP-receptor ($P_2$ T) antagonists.

The thrombin inhibitory salts may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

The anti-thrombotic salts may be combined and/or co-administered with a cardioprotectant, for example an adenosine A1 or A3 receptor agonist.

There is also provided a method for treating an inflammatory disease in a patient that comprises treating the patient with an anti-thrombotic product and an NSAID, e.g., a COX-2 inhibitor. Such diseases include but are not limited to nephritis, systemic lupus, erythematosus, rheumatoid arthritis, glomerulonephritis, vasculitis and sacoidosis. Accordingly, the anti-thrombotic salts of the disclosure may be combined and/or co-administered with an NSAID.

Typically, therefore, the salts of the formula (III) and formula (IV) acids may be administered to a host to obtain a thrombin-inhibitory effect, or in any other thrombin-inhibitory or anti-thrombotic context mentioned herein.

Actual dosage levels of active ingredients in the pharmaceutical compositions may be varied so as to obtain an amount of the active compound(s) that is effective to achieve the desired therapeutic response for a particular patient, composition, and mode of administration (referred to herein as a "therapeutically effective amount"). The selected dosage level will depend upon the activity of the particular compound, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

For example, it is currently contemplated that, in the case of oral administration of salts of TRI 50c, the salts might for instance be administered in an amount of from 0.5 to 2.5 mg/Kg twice daily, calculated as TRI 50c. Other salts might be administered in equivalent molar amounts. However, the presently described methods are not limited to administration in such quantities or regimens and includes dosages and regimens outside those described in the previous sentence.

According to a further aspect there is provided an oral pharmaceutical formulation including a product as described herein, in admixture with a pharmaceutically acceptable adjuvant, diluent or carrier.

Solid dosage forms for oral administration include capsules, tablets (also called pills), powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules and tablets, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, the oral formulations may contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavouring and perfuming agents. Suspensions, in addition to the active compounds, may contain suspending agents such as ethoxylated isostearyl alcohols, polyoxyethylene sorbitol and sorbitan esters, microcrystalline cellulose, aluminium metahydroxide, bentonite, agar-agar, and tragacanth and mixtures thereof.

The presently disclosed product may be presented as solids in finely divided solid form, for example they may be micronised. Powders or finely divided solids may be encapsulated.

The active compound may be given as a single dose, in multiple doses or as a sustained release formulation.

It will be understood from the aforegoing that there are provided pharmaceutical products comprising an alkaline earth metal salt, particularly calcium salt, of a boronic acid of Formula (III) or (IV) in dry fine particle form, suitable for oral administration. The alkaline earth metal salt is suitably an acid salt.

Synthesis

1. Peptide/Peptidomimetic Synthesis

The synthesis of boropeptides, including, for example, Cbz-D-Phe-Pro-BoroMpg-OPinacol is familiar to those skilled in the art and described in the prior art mentioned above, including Claeson et al (U.S. Pat. No. 5,574,014 and others) and Kakkar et al (WO 92/07869 and family members including U.S. Pat. No. 5,648,338). It is described also by Elgendy et al *Adv. Exp. Med. Biol.* (*USA*) 340:173–178, 1993; Claeson, G. et al *Biochem. J.* 290:309–312, 1993; Deadman et al *J. Enzyme Inhibition* 9:29–41, 1995, and by Deadman et al *J. Med. Chem.* 38:1511–1522, 1995.

Stereoselective synthesis with S or R configuration at the chiral B-terminal carbon may be conducted using established methodology (Elgendy et al *Tetrahedron. Lett.* 33:4209–4212, 1992; WO 92/07869 and family members including U.S. Pat. No. 5,648,338) using (+) or (−)-pinanediol as the chiral director (Matteson et al *J. Am. Chem. Soc.* 108:810–819, 1986; Matteson et al *Organometallics.* 3:1284–1288, 1984). Another approach is to resolve the requisite aminoboronate intermediate (e.g. Mpg-BOPinacol) to selectively obtain the desired (R)-isomer and couple it to the dipeptide moiety (e.g. Cbz-(R)-Phe-(S)-Pro, which is the same as Cbz-D-Phe-L-Pro) which will form the remainder of the molecule.

The reader is referred also to other prior documents mentioned previously in this specification, for example the US patents of Adams et al.

The boropeptides may be synthesised initially in the form of boronic acid esters, particularly esters with diols. Such diol esters may be converted to the peptide boronic acid as described next.

2. Ester to Acid Conversion

A peptide boronate ester such as Cbz-(R)-Phe-Pro-BoroMpg-OPinacol may be hydrolysed to form the corresponding acid.

A novel technique for converting a diol ester of a peptide boronic acid of formula (I) into the add comprises dissolving the diol ester in an ether and particularly a dialkyl ether, reacting the thus-dissolved diol with a diolamine, for example a dialkanolamine, to form a product precipitate, recovering the precipitate, dissolving it in a polar organic solvent and reacting the thus-dissolved product with an aqueous medium, e.g. an aqueous acid, to form the peptide boronic acid. The boronic acid may be recovered from the organic layer of the mixture resulting from the reaction, for example by removing the solvent, e.g. by evaporation under vacuum or distillation. The reaction between the diol ester and the diolamine may be carried out under reflux, for example.

The identity of the diol is not critical. As suitable diols may be mentioned aliphatic and aromatic compounds having hydroxy groups that are substituted on adjacent carbon atoms or on carbon atoms substituted by another carbon. That is to say, suitable diols include compounds having at least two hydroxy groups separated by at least two connecting carbon atoms in a chain or ring. One class of diols comprises hydrocarbons substituted by exactly two hydroxy groups. One such diol is pinacol and another is pinanediol; there may also be mentioned neopentylglycol, 1,2-ethanediol, 1,2-propanediol, 1,3-propanediol, 2,3-butane-diol, 1,2-diisopropylethanediol, 5,6-decanediol and 1,2-dicyclohexylethanediol.

The alkyl groups of the dialkyl ether preferably have 1, 2, 3 or 4 carbon atoms and the alkyl groups may be the same or different. An exemplary ether is diethyl ether.

The alkyl groups of the dialkanolamine preferably have 1, 2, 3 or 4 carbon atoms and the alkyl groups may be the same or different. An exemplary dialkanolamine is diethanolamine. The diethanolamine/boronic acid reaction product hydrolyses in water at room temperature and the rate of hydrolysis may be accelerated by adding acid or base.

The polar organic solvent is preferably $CHCl_3$. Other examples are polyhalogenated alkanes generally and ethyl acetate. In principle, any polar organic solvent is acceptable other than alcohols.

The aqueous acid is suitably a strong inorganic acid at a pH in the region of 1 such as hydrochloric acid, for example.

After reaction with the acid, the reaction mixture is suitably washed with, for example, $NH_4Cl$ or another mild base.

An example of a specific procedure is as follows:
1. The pinacol or pinanediol ester of the selected peptide boronic acid is dissolved in diethyl ether.
2. Diethanolamine is added and the mixture is refluxed at 40° C.
3. The precipitated product is removed (filtered), washed (usually several times) with diethyl ether or another polar organic solvent other than an alcohol, and dried (e.g. by evaporation under vacuum).
4. The dry product is dissolved in a polar organic solvent other than an alcohol, e.g. $CHCl_3$. Aqueous acid or base is added, e.g. hydrochloric acid (pH 1), and the mixture is stirred for e.g. approximately 1 h at room temperature.
5. The organic layer is removed and washed with $NH_4Cl$ solution.
6. The organic solvent is distilled off and the residual solid product is dried.

The above process results in the formation of what may conveniently be referred to as a "diolamine adduct" of the peptide boronic acids of formula (I), especially such adducts with diethanolamine, and such adducts are themselves included in the disclosure. The molecular structure of such adducts is not known: they might comprise a compound in which the two oxygens and the nitrogen of the diolamine are all coordinated to the boron; they might comprise ions. The adducts are however considered to be esters. A particular novel product included in the disclosure is that obtainable by reacting a pinacol or pinanediol ester of a compound of Formula (IX), particularly (R,S,R)-TRI 50c, and diethanolamine, i.e. the novel product is an (R,S,R)-TRI 50c/diethanolamine "adduct" where the acid is (R,S,R)-TRI 50c.

The diolamine materials of the disclosure may be defined as a composition of matter comprising:

(i) a species of formula (X)

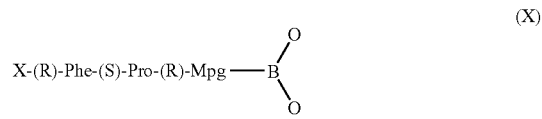

(X)

wherein X is H or an amino protecting group, the boron atom is optionally coordinated additionally with a nitrogen atom, and the valency status of the terminal oxygens is open (they may be attached to a second covalent bond, be ionised as —$O^-$, or have some other, for example intermediate, status); and, in bonding association therewith (ii) a species of formula (XI)

(XI)

wherein the valency status of the nitrogen atom and the two oxygen atoms is open. It will be appreciated that the terminal oxygen atoms of the species of formula (X) and the oxygen atoms of the species of formula (XI) may be the same oxygen atoms, in which case the species of formula (XI) forms a diol ester with the species of formula (X).

It will be appreciated that the aforegoing technique comprises an example of a method for recovering an organoboronic add product, the method comprising providing in a solvent a dissolved mixture comprising the organoboronic add in a soluble form and a compound having two hydroxy groups and an amino group (i.e. a diolamine), causing or allowing the organoboronic acid and the diolamine to react to form a precipitate, and recovering the precipitate. The soluble form of the organoboronic acid may be a diol ester, as discussed above. The solvent may be an ether, as discussed above. The organoboronic acid may be one of the organoboronic acids referred to in this specification, for example it may be of Formula III. The method described in this paragraph is novel and forms an aspect of the disclosure. A recovery method is filtration.

The reaction between the diolamine and the soluble form of the organoboronic acid is suitable carried out at an elevated temperature, for example under reflux.

Another aspect of the present disclosure is a method for recovering an organoboron species, comprising providing, in a form soluble in an ether, an organoboronic acid, for example a drug such as, e.g., a compound of formula (III) or (IV);

forming a solution of the soluble form in the ether;

combining the solution with a dialkanolamine and allowing or causing the dialkanolamine to react with the soluble form of the organoboronic acid to form an insoluble precipitate; and recovering the precipitate.

The term "soluble" in the preceding paragraph refers to species which are substantially more soluble in the reaction medium than is the precipitated product. In variants of the method, the ether is replaced by toluene or another aromatic solvent.

The diethanolamine precipitation technique described above is an example of another novel method, which is a method for recovering from ether solution a pinacol or pinanediol ester of a peptide boronic acid, comprising dissolving diethanolamine in the solution, allowing or causing a precipitate to form and recovering the precipitate. The disclosure encompasses variants of this methods in which another diol than pinacol or pinanediol is used.

The precipitated material, i.e. the "adduct", may be converted into the free organoboronic acid, for example by contacting it with an acid. The acid may be an aqueous acid, for example an aqueous inorganic acid, e.g. as described above. The precipitate may be dissolved, for example in an organic solvent, prior to being contacted with the acid.

The disclosure therefore provides a method for making an organoboronic acid, comprising converting its diolamine reaction product to the acid.

The acid resulting from the methods described in the previous two paragraphs may be converted to a salt of the acid with a multivalent metal, which salt may in turn be formulated into a pharmaceutical composition in oral dosage form.

3. Salt Synthesis

In general, the salts may be prepared by contacting the relevant boronic acid with a relevant base, e.g. the metal hydroxide (alternatively, metal carbonates might be used, for example). Sometimes it is more convenient to contact the acid with a relevant metal alkoxide (e.g. methoxide), for which purpose the corresponding alkanol is a suitable solvent. Illustrative salts are acid salts (one —BOH proton replaced) and, to make these salts, the acid and the base are usually reacted in substantially the appropriate stoichiometric quantities. Generally stated, therefore, the usual acid: base molar ratio is substantially n:1, where n is the valency of the metal cation of the base.

In one procedure, a solution of the peptide boronic acid in a water-miscible organic solvent, for example acetonitrile or an alcohol (e.g. ethanol, methanol, a propanol, for example iso-propanol, or another alkanol), is combined with an aqueous solution of the base. The acid and the base are allowed to react and the salt is recovered. The reaction is typically carried out at ambient temperature (e.g. at a temperature of from 15 to 30° C., e.g. 15 to 25° C.), but an elevated temperature may be used, for example up to the boiling point of the reaction mixture but more usually lower, e.g. a temperature of up to 40° C. or 50° C. The reaction mixture may be allowed to stand or be agitated (usually stirred).

The time during which the acid and the base are allowed to react is not critical but it has been found desirable to maintain the reaction mixture for at least one hour. A period of from one to two hours is usually suitable but longer reaction times may be employed.

The salt may be recovered from the reaction mixture by any suitable method, for example evaporation or precipitation. Precipitation may be carried out by adding an excess of a miscible solvent in which the salt has limited solubility. In one preferred technique, the salt is recovered by evaporating the reaction mixture to dryness. The salt is preferably thereafter purified, for example by redissolving the salt before filtering the resulting solution and drying it, for example by evacuating it to dryness. The redissolution may be performed using water, e.g. distilled water. The salt may then be further purified, for example in order to remove residual water by further redissolution in a suitable solvent, which is advantageously ethyl acetate or THF followed by evaporating to dryness. The purification procedure may be carried out at ambient temperature (say, 15 to 30° C., e.g. 15 to 25° C.), or at a modestly elevated temperature, such as e.g. a temperature not exceeding 40° C. or 50° C.; for example the salt may be dissolved in water and/or solvent by agitating with or without warming to, for example, 37° C.

Also included is a method for drying the salts of the disclosure and other peptide boronic acid salts, comprising dissolving them in an organic solvent, e.g. ethyl acetate or THF, and then evaporating to dryness, e.g. by evacuation.

Generally, preferred solvents for use in purifying the salts are ethyl acetate or THF, or perhaps another organic solvent.

A general procedure for synthesising multivalent metal salts of Cbz-Phe-Pro-BoroMpg-OH is as follows:

Cbz-Phe-Pro-BoroMpg-OH (20.00 g, 38.1 mM) is dissolved in acetonitrile (200 ml) with stirring at room temperature. To this solution is added the requisite base as a solution in distilled water (190 ml) [0.1M solution for a divalent metal; 0.67M solution for a trivalent metal]. The resultant clear solution is allowed to react for example by being left to stand or being agitated, for a usual period, in either case, of from one to two hours. The reaction is typically carried out at ambient temperature (e.g. 15–30° C., e.g. 15 to 25° C.) but alternatively the temperature may be elevated (e.g. up to 30° C., 40° C. or 50° C.). The reaction mixture is then evacuated to dryness under vacuum with its temperature not exceeding 37° C., typically to yield a white brittle solid or an oil/tacky liquid. The oil/tacky liquid is redissolved in the minimum amount of distilled water necessary (200 ml to 4 L), typically with warming (e.g. to 30–40° C.), usually for up to 2 hours. The solution is filtered, suitably through filter paper, and evacuated to dryness, again with the temperature of the solution not exceeding 37° C., or freeze dried. The resultant product is dried under vacuum overnight to normally yield a white brittle solid. If the product is present as an oil or tacky solid then it is dissolved in ethyl acetate and evacuated to dryness to produce the product as a white solid. The white solid is typically a coarse, amorphous powder.

In variations of the aforegoing general procedure, the acetonitrile is replaced by another water-miscible organic solvent, notably an alcohol, as discussed above, especially ethanol, methanol, iso-propanol or another propanol.

The above synthetic procedures are applicable also to preparing alkali metal salts of TRI 50c and other boronic acids described herein, for example those of formula (III). These alkali metal salts are useful as a starting material for alternative syntheses of multivalent metal salts, where direct synthesis from the acid is inconvenient, as in the case of a multivalent metal hydroxide which is less soluble in a selected reaction medium for salt formation (e.g. zinc hydroxide). When an alkali metal salt is being made as starting material, the stoichiometry of the reaction used to make the alkali metal salt is usually adjusted to 1:1, in order to prepare an acid salt. In such an "indirect" synthesis from an alkali metal salt, especially the sodium salt or alternatively the potassium salt, the boronate alkali metal salt in solution is contacted with a salt of the relevant metal (normally a salt having a pharmaceutically acceptable anion, e.g. chloride). The salt of the "target" metal (e.g. zinc) is typically used in a stoichiometry (boronic acid:target metal) of n:1, where n is the valency of the metal. The multivalent metal salt of the boronic acid is then recovered, for example it will often precipitate out (when the multivalent metal salt is less soluble in the reaction medium than is the alkali metal salt). The resulting precipitate may then be separated from the liquid, e.g. by filtration, and purified.

The preparation of the multivalent metal salts from the corresponding alkali metal salts is novel. The alkali metal salts and their aqueous solutions also form part of the present disclosure. The alkali metal salts are an advantageous as compared to the corresponding acids in that they are more resistant to degradation (their boropeptide moieties are less prone to degrade than are those of the corresponding free acids).

Also provided is the use of a peptide boronic acid drug, for example a thrombin inhibitor or an acid of formula (I), to make a salt as disclosed herein. Included also is a method of preparing a product, comprising contacting a peptide boronic acid drug, e.g. of formula (I), (II), (III), (IV) or (IX), with a base capable of making such a salt.

The peptide boronic acid used to prepare the pharmaceutical preparations is typically of GLP or GMP quality, or in compliance with GLP (good laboratory practice) or GMP (good manufacturing practice). Such acids are included in the disclosure.

Similarly the acids are usually sterile and/or acceptable for pharmaceutical use, and one aspect of the present disclosure resides in a composition of matter which is sterile or acceptable for pharmaceutical use, or both, and comprises a peptide boronic acid of formula (IV). Such a composition of matter may be in particulate form or in the form of a liquid solution or dispersion.

The intermediate acid may be in isolated form and such isolated acids are included in the present disclosure, especially isolated acids which are a peptide boronic acid of formula (IX):

$$X\text{---}(R)\text{-}Phe\text{-}(S)\text{-}Pro\text{-}(R)\text{-}Mpg\text{-}B(OH)_2 \quad \text{(IX)}$$

wherein X is H (to form $NH_2$) or an amino-protecting group.

One typical way of providing the intermediate acids is as a particulate composition consisting predominantly of such a peptide boronic acid, and these compositions are included in the disclosure. The peptide boronic acid often forms at least 75% by weight of the composition and typically at least 85% by weight of the composition, e.g. at least 95% by weight of the composition.

Another typical way of providing the intermediate acids is as a liquid composition consisting of, or consisting essentially of, a peptide boronic acid of formula (II) and a liquid vehicle in which it is dissolved or suspended. The liquid vehicle may be an aqueous medium, e.g. water, or an alcohol, for example methanol, ethanol, isopropanol, or another propanol, another alkanol or a mixture of the aforegoing.

The compositions of the intermediate acids are generally sterile. The compositions may contain the peptide boronic acid in finely divided form, to facilitate further processing.

Separation of Stereoisomers

The stereoisomers of a peptide boronic ester or a synthetic intermediate aminoboronate may be resolved in, for example, any known way. In particular, stereoisomers of boronic esters may be resolved by HPLC.

EXAMPLES

Examples 1 to 3

Introductory Remarks

Apparatus

Throughout the following procedures of Examples 1 to 3, standard laboratory glassware and, where appropriate, specialised apparatus for handling and transferring of air sensitive reagents are used.

All glassware is heated at 140–160° C. for at least 4 hours before use and then cooled either in a desiccator or by assembling hot and purging with a stream of dry nitrogen.

Solvents

The organic solvents used in the procedures of Examples 1 to 3 are all dry. Suitably, they are dried over sodium wire before use.

Dryness

In the drying procedures of Example 1 to 3, products are tested for dryness (including dryness in terms of organic solvent) by observing weight loss on drying. The following procedure was followed to determine loss on drying: a sample was placed in a vacuum drier and dried at 40° C. at 100 mbar for 2 hours. Products are considered dry when the decrease in weight upon drying is less than 0.5% of the total weight of the starting material.

Examples 1 to 3 describe performance of the following reaction scheme and conversion of the resultant TRI 50c to a calcium salt thereof:

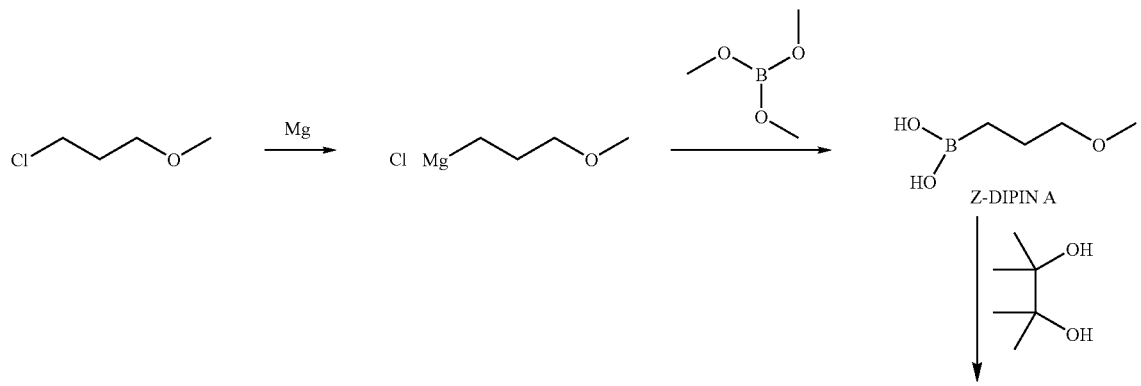

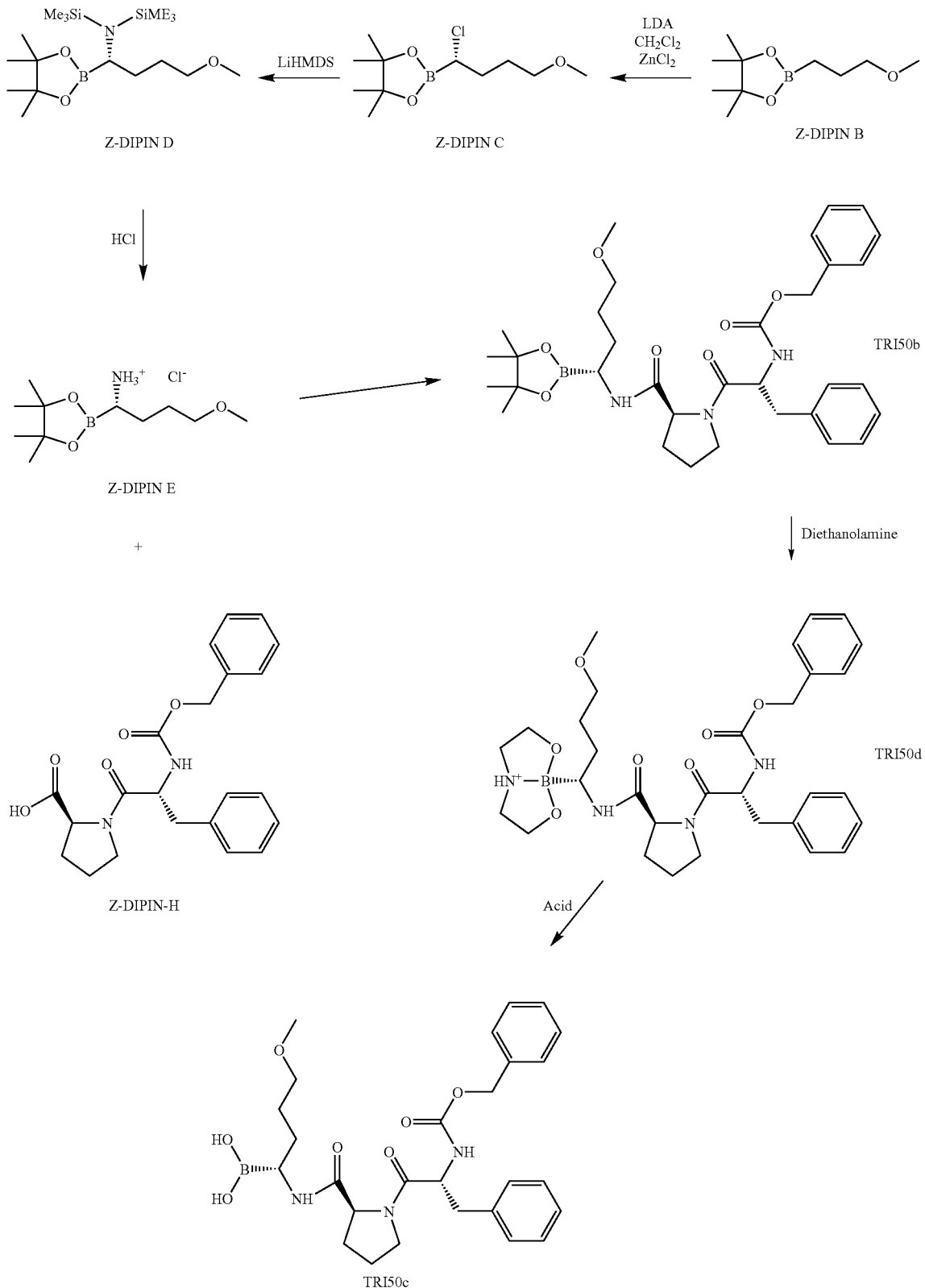
LDA = lithium diisopropylamide
LiHMDS = lithium hexamethyldisilazane, also known as lithium bis(trimethylsiyl)amide

Example 1

Synthesis of TRI 50D

Step 1: Z-DIPIN B

Procedure A 17.8 g (732.5 mmole) magnesium turnings, 0.1 g (0.4 mmole) iodine and 127 ml dry tetrahydrofuran are charged and heated to reflux. Then 15 ml of a solution of 66 g (608 mmole) 1-chloro-3-methoxypropane in 185 ml dry tetrahydrofuran are added and stirred under reflux until the vigorous reaction starts. After the initial exotherm ceases, the solution of 1-chloro-3-methoxypropane is added slowly to maintain gentle reflux until all the magnesium is consumed. After the reaction is finished, the reaction mixture is cooled to ambient temperature and slowly added to a solution of 64.4 g (620 mmole) trimethylborate in 95 ml dry tetrahydrofuran; the latter solution is cooled to below 0° C. and, if it warms up during the course of the reaction, the reaction mixture must be added to it sufficiently slowly to maintain the temperature of this solution below 65° C. Upon complete addition, the reaction mixture is allowed to warm to about 0° C. and stirred for another 60 minutes. Then a solution of 22.4 ml sulfuric acid in 400 ml water is added slowly so as to maintain the temperature below 20° C. The layers are allowed to settle and the phases are separated. The aqueous layer is rewashed three times with 200 ml tert.-butylmethylether. The combined organic layers are allowed to settle and additional water separated from this solution is removed. The organic layer is dried over magnesium sulfate, filtered and evaporated to dryness. The evaporation residue is filtered from the precipitated solid and the filtrate dissolved in 175 ml toluene. 34.8 g (292 mmole) pinacol is charged to the solution followed by stirring at ambient temperature for not less than 10 hours. The solution is evaporated to dryness, dissolved in 475 ml n-heptane and washed three times with 290 ml saturated aqueous solution of sodium hydrogen carbonate. The n-heptane solution is evaporated to dryness and the evaporation residue distilled and the fraction with Bp 40–50° C. at 0.1–0.5 mbar recovered.

Boiling point: 40–50° C./0.1–0.5 mbar

Yield: 40.9 g (70%) Z-DIPIN B (oil)

Procedure B 17.8 g (732.5 mmole) magnesium turnings, 0.1 g (0.4 mmole) iodine and 127 ml dry tetrahydrofuran are charged and heated to reflux. Then 15 ml of a solution of 66 g (608 mmole) 1-chloro-3-methoxypropane in 185 ml dry tetrahydrofuran are added and stirred under reflux until the vigorous reaction starts. After the initial exotherm ceases, the solution of 1-chloro-3-methoxypropane is added slowly to maintain gentle reflux. After the reaction is finished, the reaction mixture is cooled to ambient temperature and slowly added to a solution of 64.4 g (620 mmole) trimethylborate in 95 ml dry tetrahydrofuran, maintaining the temperature of this solution below minus 65° C. Upon complete addition, the reaction mixture is allowed to warm to about 0° C. and stirred for another 60 minutes. Then a solution of 22.4 ml sulfuric acid in 400 ml water is added slowly so as to maintain the temperature below 20° C. The organic solvent is removed by distillation under vacuum. 300 ml n-heptane is charged to the aqueous solution of the evaporation residue followed by addition of 34.8 g (292 mmole) pinacol. The two-phase-mixture is stirred at ambient temperature for not less than 2 hours. After allowing the layers to settle, the aqueous phase is separated. 300 ml n-heptane is charged to the aqueous solution and the two-phase-mixture is stirred at ambient temperature for not less than 2 hours. After allowing the layers to settle, the aqueous phase is separated. The organic layers are combined and washed once with 200 ml water, followed by 200 ml saturated sodium hydrogen carbonate solution and two further washes with 200 ml water each. The n-heptane solution is evaporated to dryness and the evaporation residue distilled and the fraction with Bp 40–50° C. at 0.1–0.5 mbar recovered.

Boiling point: 40–50° C./0.1–0.5 mbar

Yield: 40.9 g (70–85%) Z-DIPIN B (oil)

Step 2: Z-DIPIN C 16.6 g (164 mmole) diisopropylamine and 220 ml tetrahydrofuran are charged and cooled to −30 to −40° C. To this solution 41.8 g (163 mmole) n-butyl lithium, 25% in n-heptane is added, followed by stirring at 0 to −5° C. for one hour. This freshly prepared solution of lithium diisopropylamide is cooled to −30° C. and then added to a solution of 27.9 g (139 mmole) Z-DIPIN B in 120 ml tetrahydrofuran and 35.5 g (418 mmole) dichloromethane at a temperature between −60 and −75° C. The solution is stirred at that temperature for half an hour followed by addition of 480 ml (240 mmole) 0.5N anhydrous Zinc(II)-chloride in tetrahydrofuran or 32.5 g (240 mmole) anhydrous solid Zinc(II)-chloride. After stirring at −65° C. for one hour, the reaction mixture is allowed to warm to ambient temperature and stirred for another 16–18 hours. The reaction mixture is evaporated to dryness (i.e. until solvent is removed) and followed by addition of 385 ml n-heptane. The reaction mixture is washed with 150 ml 5% sulfuric acid, with 190 ml saturated sodium hydrogen carbonate solution, and 180 ml saturated sodium chloride solution. The organic layer is dried over magnesium sulfate, filtered and evaporated to dryness (i.e. until solvent is removed). The oily residue is transferred into the next step without further purification.

Yield: 19 g (55%) Z-DIPIN C

Step 3: Z-DIPIN D

To a solution of 23.8 g (148 mmole) hexamethyldisilazane in 400 ml tetrahydrofuran at −15° C. is added 34.7 g (136 mmole) n-butyl lithium, 25% in n-heptane and stirred for one hour. The solution is cooled to −55° C. followed by the addition of 30.6 g (123 mmole) Z-DIPIN C dissolved in 290 ml tetrahydrofuran and 35 ml tetrahydrofuran to this freshly prepared solution of LiHMDS. The solution is allowed to warm to ambient temperature and stirred for 12 hours. The reaction mixture is evaporated to dryness, the evaporation residue dissolved in 174 ml n-heptane, washed with 170 ml water and 75 ml saturated sodium chloride solution. The organic phase is dried over magnesium sulfate, filtered and evaporated to complete dryness (i.e. until solvent is removed). The oily residue is dissolved in 100 g n-heptane. This solution is carried over into the next step without further purification.

Yield: 32.2 g (70%) Z-DIPIN D

Step 4: Z-DIPIN (TRI50b, Crude)

A solution of 26.6 g (71 mmole) Z-DIPIN D in 82.6 g n-heptane is diluted with 60 ml n-heptane and cooled to −60° C. followed by introduction of 10.5 g (285 mmole) hydrogen chloride. The reaction mixture is subsequently evacuated and flushed with nitrogen, while the temperature is increased in increments of about 20° C. to ambient temperature. The solvent is removed from the oily precipitate and replaced several times by 60 ml fresh n-heptane. The oily residue is dissolved in 60 ml tetrahydrofuran (Solution A).

To a different flask 130 ml tetrahydrofuran, 24.5 g (61.5 mmole) Z-D-Phe-Pro-OH and 6.22 g (61.5 mmole) N-methylmorpholine are charged and cooled to −20° C. To this solution a solution of 8.4 g (61.5 mmole) isobutylchloroformate in 20 ml tetrahydrofuran is added and stirred for 30 minutes, followed by addition of Solution A at −25° C. Upon complete addition, up to 16 ml (115 mmole) triethylamine is added to adjust the pH to 9–10, measured using a pH stick. The reaction mixture is allowed to warm to ambient temperature and stirred for 3 hours, still under nitrogen. The solvent is evaporated to dryness and the evaporation residue dissolved in 340 ml tert.-butylmethylether (t-BME). The solution of Z-DIPIN in t-BME is washed twice with 175 ml 1.5% hydrochloric acid. The combined acidic washes are given a rewash with 175 ml t-BME. The combined organic layers are washed with 175 ml water, with 175 ml saturated sodium hydrogen carbonate solution, with 175 ml 25% sodium chloride solution, dried over magnesium sulfate and filtered. This solution is carried over into the next step without further purification.

Yield: 29.9 g (80%) Z-DIPIN

Example 2

Synthesis of TRI 50D (Diethanolamine Adduct of TRI 50C)

The starting material used in this Example is the solution of TRI 50b ("Z-DIPIN") obtained in Example 1. The solution is carried forward to the synthesis of TRI 50d without further purification. The solution of Z-DIPIN in t-BME (containing 7.0 g (11.5 mmole) (R,S,R) TRI50b, calculated based on HPLC results of Z-DIPIN) is evaporated to dryness and the evaporation residue dissolved in 80 ml diethylether. 1.51 g (14.4 mmole) diethanolamine is added and the mixture heated at reflux for at least 10 hours, during which process the product precipitates. The suspension is cooled to 5–10° C., filtered and the filter residue washed with diethylether.

To improve chiral and chemical purity the wet filter cake (7 g) is dissolved in 7 ml dichloromethane, cooled to 0–5° C. and the product precipitated by addition of 42 ml diethylether and filtered. The isolated wet product is dried at 35° C. in vacuum or at least 4 hours, until day.

Yield: 5.5 g (80%) Tri50d

Melting Point: 140–145° C.

Example 3

Preparation of Calcium Salt of TRI50C 1.5 kg (2.5 mole) TRI50d from Example 2 is dissolved in 10.5 L dichloromethane. 11 L 2% hydrochloric acid is added and the mixture is stirred for at most 30 minutes (optimally about 20 minutes) at room temperature. After stirring the layers are allowed to settle and separated. The aqueous layer is given a rewashed twice with 2.2 L dichloromethane. The combined organic layers are washed with a solution of 625 g ammonium chloride in 2.25 L water. The organic phase is dried over magnesium sulfate, filtered and the filtrate evaporated to dryness. An assay of the free boronic acid is performed and the amounts of the solvents and base for conversion of the acid to the salt are calculated. If 2.5 mol of the free acid is obtained, the evaporation residue is dissolved in 5 L acetonitrile followed by addition of a suspension of 93 g (1.25 mole) calcium hydroxide in 1 L water. The solution is stirred for two hours at ambient temperature (e.g. 15–30° C., optimally room temperature) and then evaporated under vacuum (of ca. 10 mmHg) at a temperature initially of about 10° C. and then increasing to a limit of about 35° C. The evaporation residue is repeatedly dissolved in 3.5 L fresh acetonitrile and evaporated to dryness to remove traces of water. If the evaporation residue is dry, it is dissolved in 6 L tetrahydrofuran and slowly added to a mixture of 32 L n-heptane and 32 L diethylether. The addition is performed slowly enough to avoid lumping or sticking of the product and is carried out over a period of not less than 30 minutes. The precipitated product is filtered off, washed with n-heptane and dried under vacuum (of ca. 10 mmHg) at a temperature below 35° C. until dry.

Yield: 0.98 kg (70%) Tri50c calcium salt.

The procedures of Examples 1 to 4 may be scaled up and, if operated carefully, will produce highly pure salts. In the diethanolamine precipitation step it is important to use 1.25 equivalents of diethanolamine per equivalent of (R,S,R) TRI 50b. In the hydrolysis of the diethanolamine ester, it is important to avoid excessively long contact with the aqueous acid. Likewise the TRI 50b should be synthesised via the Grignard reaction to Z-DIPIN A.

Example 4

Alternative Conversion of TRI 50B to TRI 50C

The synthetic procedures described in this and subsequent synthetic examples were generally performed under nitrogen and using dry solvents as supplied from commercial sources.

1. Approximately 300 g of TRI 50b, obtained by the HPLC purification of racemic TRI 50b) were dissolved in approximately 2.5 L diethylether. It is estimated that different batches of TRI 50b had isomeric purities ranging from 85% R,S,R to in excess of 95% R,S,R.
2. Approximately 54 ml diethanolamine were added (1:1 stoichiometry with total TRI 50b content), and the mixture was refluxed at 40° C.
3. The precipitated product was removed, washed several times with diethylether and dried.
4. The dry product was dissolved in $CHCl_3$. Hydrochloric acid (pH 1) was added and the mixture was stirred approximately 1 h at room temperature.
5. The organic layer was removed and washed with $NH_4Cl$ solution.
6. The organic solvent was distilled off and the residual solid product was dried.

Typical yield: Approximately 230 g

Example 5

First Alternative Preparation of Calcium Salt of TRI 50C

Cbz-Phe-Pro-BoroMpg-OH (20.00 g, 38.1 mM) obtained by the method of Example 4 is dissolved in acetonitrile (200 ml) with stirring at room temperature. To this solution is added $Ca(OH)_2$ as a 0.1M solution in distilled water (190 ml). The resultant dear solution is stirred for 2 hours at room temperature and then evacuated to dryness under vacuum with its temperature not exceeding 37° C. The resultant product is a white brittle solid.

The salt was then dried under vacuum over silica to constant weight (72 h).

Yield: 17.69 g.

Example 6

Second Alternative Preparation of Calcium Salt of TRI 50C 50.0 g TRI 50c (95.2 mmol) were dissolved under stirring in 250 ml acetonitrile at room temperature and then cooled with an ice bath. To this ice cooled solution 100 ml of an aqueous suspension of 3.5 g (47.6 mmol) calcium hydroxide was added dropwise, stirred for 2.5 hours at room temperature, filtered and the resulting mixture evaporated to dryness, the temperature not exceeding 35° C. The clear yellowish oily residue was redissolved in 200 ml acetone and evaporated to dryness. The procedure of redissolving in acetone was repeated one more time to obtain colourless foam.

This foam was redissolved in 100 ml acetone, filtered and added dropwise to an ice cooled solution of 1100 ml petrol ether 40/60 and 1100 ml diethylether. The resulting colourless precipitate was filtered, washed two times with petrol ether 40/60 and dried under high vacuum, yielding 49.48 g of a colourless solid (92%), with a purity of 99.4% according to an HPLC measurement.

Example 7

UV/Visible Spectra of Calcium Salt of TRI 50C

UV/Visible spectra of the salt resulting from the procedure of Example 5 were recorded in distilled water at 20° C. from 190 nm to 400 nm. TRI 50C and the salt gave $\lambda_{max}$ at 210 and 258 nm. The weight of the dried salt was then measured for the purposes of calculating the extinction coefficient. The $\lambda_{max}$ at 258 nm was used. The extinction coefficient was calculated using the formula:-

A=εcl where A is the absorbance

C is the concentration
l the path length of the UV cell
and ε is the extinction coefficient.
Extinction coefficient: 955.

Example 8

Aqueous Solubility of Calcium Salt of TRI 50C

The salt used in this Example was made using a modification of the process described in Example 6. The modified process differs from that described in that 100 mg of TRI 50c was used as starting material, the product of the redissolution in water was dried by freeze drying and the filtration was carried out through a 0.2 μm filter. The salt is believed to contain about 85% of R,S,R isomer.

To determine maximum aqueous solubility 25 mg of the dried salt were shaken in water at 37° C., the sample filtered and the UV spectrum measured. The salt left a white residue of undissolved material.

Solubility when dissolved at 25 mg/ml: 5 mM (5 mg/ml).

Example 9

In Vitro Activity of Calcium Salt of TRI 50C

TRI 50c calcium salt was assayed as an inhibitor of human α-thrombin by an amidolytic assay (J. Deadman et al, *J. Med. Chem.* 38:15111–1522, 1995, which reports a Ki value of 7 nM for TRI 50b).

The inhibition of human α-thrombin therefore, was determined by the inhibition of the enzyme catalysed hydrolysis of three different concentrations of the chromogenic substrate S-2238.

200 μl of sample or buffer and 50 μl of S-2238 were incubated at 37° C. for 1 minute and 50 μl of human α-thrombin (0.25 NIHμ/ml) was added. The initial rate of inhibited and uninhibited reactions were recorded at 4.5 nm. The increase in optical density was plotted according to the method of Lineweaver and Burke. The Km and apparent Km were determined and Ki was calculated using the relationship.

$$V = \frac{V\max}{1 + \frac{Km}{[S]} \cdot \left(1 + \frac{[I]}{Ki}\right)}$$

The buffer used contained 0.1M sodium phosphate, 0.2M NaCl, 0.5% PEG and 0.02% sodium azide, adjusted to pH 7.5 with orthophosphoric acid.

The samples consist of the compound dissolved in DMSO.

The reader is referred to Dixon, M and Webb, E. C., "Enzymes", third edition, 1979, Academic Press, the disclosure of which is incorporated herein by reference, for a further description of the measurement of Ki.

TRI 50c calcium salt was observed to have a Ki of 10 nM.

Example 10

Preparation of Zinc Salt of TRI 50C

The relative solubilities of the respective hydroxides of magnesium and zinc are such that, if these hydroxides had been used to prepare the corresponding TRI 50c salts using the procedure of Example 5, they would not have resulted in homogeneous salt formation. New methods were therefore developed to prepare the zinc and magnesium salts, as described in this and the next examples.

TRI 50c sodium salt (2.24 g, 4.10 mM) was dissolved in distilled water (100 ml) at room temperature and zinc chloride in THF (4.27 ml, 0.5M) was carefully added with stirring. A white precipitate that immediately formed was filtered off and washed with distilled water. This solid was dissolved in ethyl acetate and washed with distilled water (2×50 ml). The organic solution was evacuated to dryness and the white solid produced dried over silica in a desiccator for 3 days before microanalysis. Yield 1.20 g.

$^1$H NMR 400 MHz, $\delta_H$(CD$_3$OD) 7.23–7.33 (20H, m, ArH), 5.14 (4H, m, PhCH$_2$O), 4.52 (4H, m, αCH), 3.65 (2H, m), 3.31 (12H, m), 3.23 (6H, s, OCH$_3$), 2.96 (4H, d, J7.8 Hz), 2.78 (2H, m), 2.58 (2H, m), 1.86 (6H, m), 1.40 (10H, m). $^{13}$C NMR 75 MHz 393K $\delta_C$(CD$_3$OD) 178.50, 159.00, 138.05, 137.66, 130.54, 129.62, 129.50, 129.07, 128.79, 128.22, 73.90, 67.90, 58.64, 58.18, 56.02, 38.81, 30.06, 28.57, 28.36, 25.29. FTIR (KBr disc) $v_{max}$ (cm$^{-1}$) 3291.1, 3062.7, 3031.1, 2932.9, 2875.7, 2346.0, 1956.2, 1711.8, 1647.6, 1536.0, 1498.2, 1452.1, 1392.4, 1343.1, 1253.8, 1116.8, 1084.3, 1027.7, 916.0, 887.6, 748.6, 699.4, 595.5, 506.5.

Example 11

Preparation of Magnesium Salt of TRI 50C

TRI 50c (1.00 g, 1.90 mM) was dissolved in methanol (10 ml) and stirred at room temperature. To this solution was added magnesium methoxide (Mg(CH$_3$O)$_2$) in methanol (1.05 ml, 7.84 wt %). This solution was stirred for 2 hours at room temperature filtered and evacuated to 5 ml. Water (25 ml) was then added and the solution evacuated down to dryness to yield a white solid. This was dried over silica for 72 hours before being sent for microanalysis. Yield 760 mg.

$^1$H NMR 300 MHz, $\delta_H$(CD$_3$C(O)CD$_3$) 7.14–7.22 (20H, m), 6.90 (2H, m), 4.89 (4H, m, PhCH$_2$O), 4.38 (2H, m), 3.40 (2H, br s), 2.73–3.17 (20H, broad unresolved multiplets), 1.05–2.10 (16H, broad unresolved multiplets). $^{13}$C NMR 75 MHz 393K $\delta_C$(CD$_3$C(O)CD$_3$) 206.56, 138.30, 130.76, 129.64, 129.31, 129.19, 129.09, 128.20, 128.04, 74.23, 73.55, 67.78, 58.76, 56.37, 56.03, 48.38, 47.87, 39.00, 25.42, 25.29. FTIR (KBr disc) $v_{max}$ (cm$^{-1}$) 3331.3, 3031.4, 2935.3, 2876.9, 2341.9, 1956.1, 1711.6, 1639.9, 1534.3, 1498.1, 1453.0, 1255.3, 1115.3, 1084.6, 1027.6, 917.3, 748.9, 699.6, 594.9, 504.5, 467.8.

Example 12

Analysis of Calcium, Magnesium and Zinc Salts of (R,S,R) TRI 50C

The following salts were prepared using a boronate:metal stoichiometry of n:1, where n is the valency of the metal, using (R,S,R) TRI 50c of higher chiral purity than that used to prepare the salts described in Example 8.

A. Calcium Salt (Product of Example 5)

| Analytical data | | |
|---|---|---|
| HPLC or LC/MS: | HPLC betabasic C18 Column, CH$_3$CN, Water | |
| Estimated Purity: | >95% by UV ($\lambda_{215nm}$) | |
| Micro analysis: | Calcd. | Found. |
| C: | 59.27 | 55.08 |
| H: | 6.48 | 6.43 |
| N: | 7.71 | 7.08 |
| Other: B: | 1.99 | 2.01 |
| Ca: | 3.68 | 3.65 |

| Physical Properties | |
|---|---|
| Form: | Amorphous solid |
| Colour: | White |
| Melting Point: | N/A |
| Solubility: | Soluble in aqueous media ca~4 mg/ml |
| M$_w$: | 1088.89 |

B. Magnesium Salt (Product of Example 11)

| Analytical data | | |
|---|---|---|
| HPLC or LC/MS: | HPLC betabasic C18 Column, CH$_3$CN, Water | |
| Estimated Purity: | >90% by UV ($\lambda_{215nm}$) | |
| Micro analysis: | Calcd. | Found. |
| C: | 60.44 | 57.25 |
| H: | 6.57 | 6.71 |
| N: | 7.83 | 7.45 |
| Other: B: | 2.01 | 2.02 |
| Mg: | 2.26 | 2.12 |

| Physical Properties | |
|---|---|
| Form: | Amorphous solid |
| Colour: | White |
| Melting Point: | N/A |
| Solubility: | Soluble in aqueous media ca~7 mg/ml |
| M$_w$: | 1073.12 |

C. Zinc Salt (Product of Example 10)

| Analytical data | | |
|---|---|---|
| HPLC or LC/MS: | HPLC betabasic C18 Column, CH$_3$CN, Water | |
| Estimated Purity: | >95% by UV ($\lambda_{215nm}$) | |
| Micro analysis: | Calcd. | Found. |
| C: | 58.21 | 56.20 |
| H: | 6.33 | 6.33 |
| N: | 7.54 | 7.18 |
| Other: B: | 1.94 | 1.84 |
| Zn: | 5.87 | 7.26 |

| Physical Properties | |
|---|---|
| Form: | Amorphous solid |
| Colour: | White |
| Melting Point: | N/A |
| Solubility: | Soluble in aqueous media ca~2 mg/ml |
| M$_w$: | 1114.18 |

Notes. The trigonal formula of the acid boronate is used in the calculated microanalyses. It is believed that a lower calcium salt solubility is reported in example 8 because the salt tested in example 8 had lower chiral purity.

CONCLUSION

The zinc, calcium and magnesium salts have all been prepared with a stoichiometry of one metal ion to two molecules of TRI 50c. The values found for the calcium and magnesium salts are close to and thus consistent with those calculated for this 1:2 stoichiometry. For the zinc salt an excess of zinc was found; nonetheless, the zinc salt comprises a significant proportion of acid boronate.

Example 13

Stability

This Example compares the stability of TRI 50c and TRI 50c calcium salt when filled into enteric-coated hard gelatin capsules (see Example 20).

| Compound. | Packing | Climatic conditions 1.5 month[0] | Purity (HPLC % Area) T0 | Purity (HPLC % Area)[3] T1 |
|---|---|---|---|---|
| TRI50c | capsules in blister | 25° C./60% r.h.[4] | 99 | 73.9 |
| TRI50c | capsules in blister | 40° C./75% r.h | 99 | 73.9 |

-continued

| Compound. | Packing | Climatic conditions 1.5 month[0] | Purity (HPLC % Area) T0 | Purity (HPLC % Area)[3] T1 |
|---|---|---|---|---|
| TRI50c | capsules[1] | 40° C./75% r.h | 99 | 75.3 |
| TRI50c Calcium Salt | capsules in blister | 25° C./60% r.h. | 99.2[2] | 98.0 |
| TRI50c Calcium Salt | capsules in blister | 40° C./75% r.h | 99.2[2] | 97.2 |
| TRI50c Calcium Salt | capsules[1] | 40° C./75% r.h | 99.2[2] | 95.0 |

Notes:
[0]1.5 month storage at given conditions, samples were then stored at room temperature until analytical testing.
[1]capsules stored at the respective climatic conditions without blister.
[2]purity of the batch before storage.
[3]purity of the stored batch (capsules were poured out, the contents of the capsules were then analyzed).
[4]r.h. = relative humidity 2. Analytical Procedure 2.1 Sample Preparation 2.1.1 Assay of TRI 50c and Salts TRI 50c-standard (free acid) was stored in a desiccator over phosphorus pentoxide for 2 days for drying. Afterwards, the reference standard was weighed in a volumetric flask and dissolved in a mixture of acetonitrile and water (25/75 v/v %). Aliquots of the resulting solution (ST 1A) were diluted successively with water as shown in the dilution scheme of table 4.

| Stock- and Calibration solutions of Tri 50c | | | | | | |
|---|---|---|---|---|---|---|
| | Net weight mg | Purity % | Salt-Factor | Dissolved in ml | Solvent | Conc. [µg/ml] | Calibr. [µg/ml] |
| ST 1 A | 40.8 | 98.23 | 1 | 10 | ACN/water 25/75 (v/v %) | 4007.8 | C4000 |

| | ml | ST | [µg/ml] | ad ml | Solvent | [µg/ml] | |
|---|---|---|---|---|---|---|---|
| ST 2 A | 5 | 1 A | 4007.8 | 10 | water | 2003.9 | C2000 |
| ST 3 A | 5 | 2 A | 2003.9 | 10 | water | 1001.9 | C1000 |
| ST 4 A | 5 | 3 A | 1001.9 | 10 | water | 501.0 | C500 |
| ST 5 A | 5 | 4 A | 500.9 | 10 | water | 250.5 | C250 |
| ST 6 A | 1 | 3 A | 1001.9 | 10 | water | 100.2 | C100 |
| ST 7 A | 1 | 6 A | 100.2 | 10 | water | 10.0 | C10 |

2.1.2 Impurity Profile of the Stored Capsules

The stored capsules of every batch at corresponding climatic condition were removed and 10 mg of the content was weighed in a 10 ml volumetric flask and dissolved in 10 ml of a mixture of acetonitrile/water (25/75 v/v %). These solutions were injected for impurity profile analysis and for quantification respectively.

3. Data Evaluation

The quantitative evaluation and the impurity profile analysis were performed using an HPLC-PDA method. The processing wavelength was set as 258 nm.

4. Analytical Parameters

| | |
|---|---|
| Autosampler | Waters Alliance 2795 |
| Pump | Waters Alliance 2795 |
| Column oven | Waters Alliance 2795 |
| Detection | Waters 996 diode array, extracted wavelength 258 nm |
| Software version | Waters Millennium Release 4.0 |

4.2 Stationary Phase

| | |
|---|---|
| Analytical Column ID | S71 |
| Material | X-Terra™ MS $C_{18}$, 5 µm |
| Supplier | Waters, Eschborn, Germany |
| Dimensions | 150 mm × 2.1 mm (length, internal diameter) |

4.3 Mobile Phase

| Aqueous phase: | A: 0.1% HCOOH in water |
|---|---|
| Organic phase: | C: ACN |

| Gradient conditions: | | | |
|---|---|---|---|
| Time | Flow | % A | % C |
| 0.00 | 0.5 | 90 | 10 |
| 27.0 | 0.5 | 10 | 90 |
| 27.1 | 0.5 | 90 | 10 |
| 30.0 | 0.5 | 90 | 10 |

5. Impurity Profile Tables of TRI50C Ca Salt

| Capsules in blister 25° C./60% r.h. | | | | | |
|---|---|---|---|---|---|
| Name | Amount [µg/ml] | Retention Time [min.] | Area | % Area | Height |
| Benzaldeh. | | 6,058 | 7927 | 1.29 | 392 |
| Tri50c | 930,903 | 11,686 | 601551 | 98.02 | 25135 |
| | | 19,199 | 839 | 0.14 | 89 |
| | | 19,498 | 1821 | 0.30 | 105 |
| | | 20,168 | 1581 | 0.26 | 158 |

The corresponding HPLC trace is shown in FIG. 1.

Capsules in blister 40° C./75% r.h.

| Name | Amount [µg/ml] | Retention Time [min.] | Area | % Area | Height |
|---|---|---|---|---|---|
| Benzaldeh. | | 6,060 | 12270 | 2.37 | 586 |
| Tri50c | 786,223 | 11,681 | 503867 | 97.19 | 21324 |
| | | 19,517 | 707 | 0.14 | 97 |
| | | 20,185 | 1614 | 0.31 | 169 |

Figure 2:
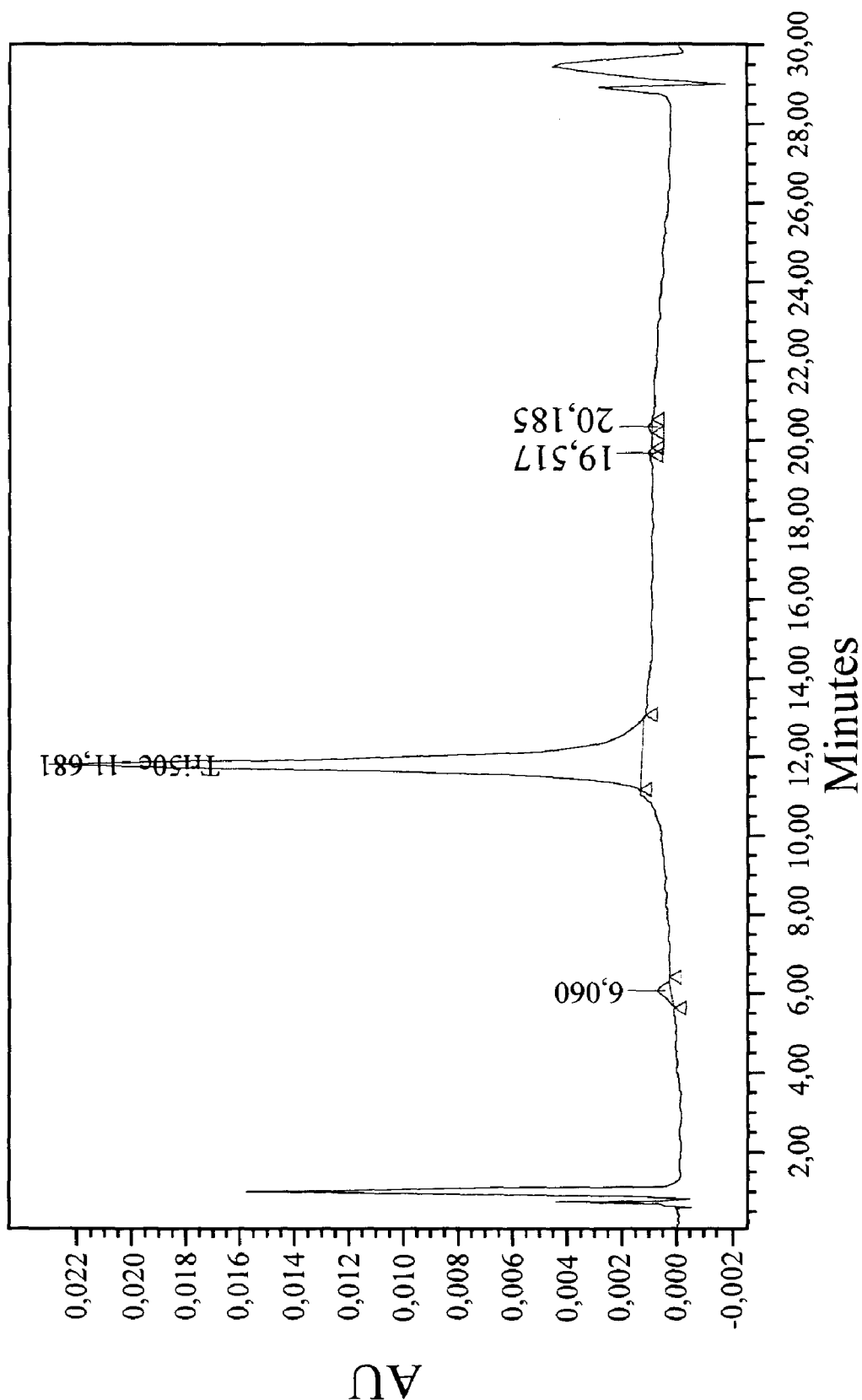
FIG. 2 is an HPLC plot referred to in Example 13, showing an impurity profile of encapsulated TRI 50c calcium salt after having been maintained in blister packaging for 1.5 month at 40° C. and 75% relative humidity.

The corresponding HPLC time is shown in FIG. 2.

Capsules (no blister) 40° C./75% r.h.

| Name | Amount [µg/ml] | Retention Time [min.] | Area | % Area | Height |
|---|---|---|---|---|---|
| Benzaldeh. | | 6,041 | 19170 | 3.64 | 992 |
| Imp.I | | 10,897 | 4433 | 0.84 | 345 |
| Tri50c | 780,097 | 11,666 | 499730 | 94.96 | 21526 |
| | | 19,494 | 805 | 0.15 | 110 |
| | | 20,156 | 2100 | 0.40 | 176 |

Figure 3:
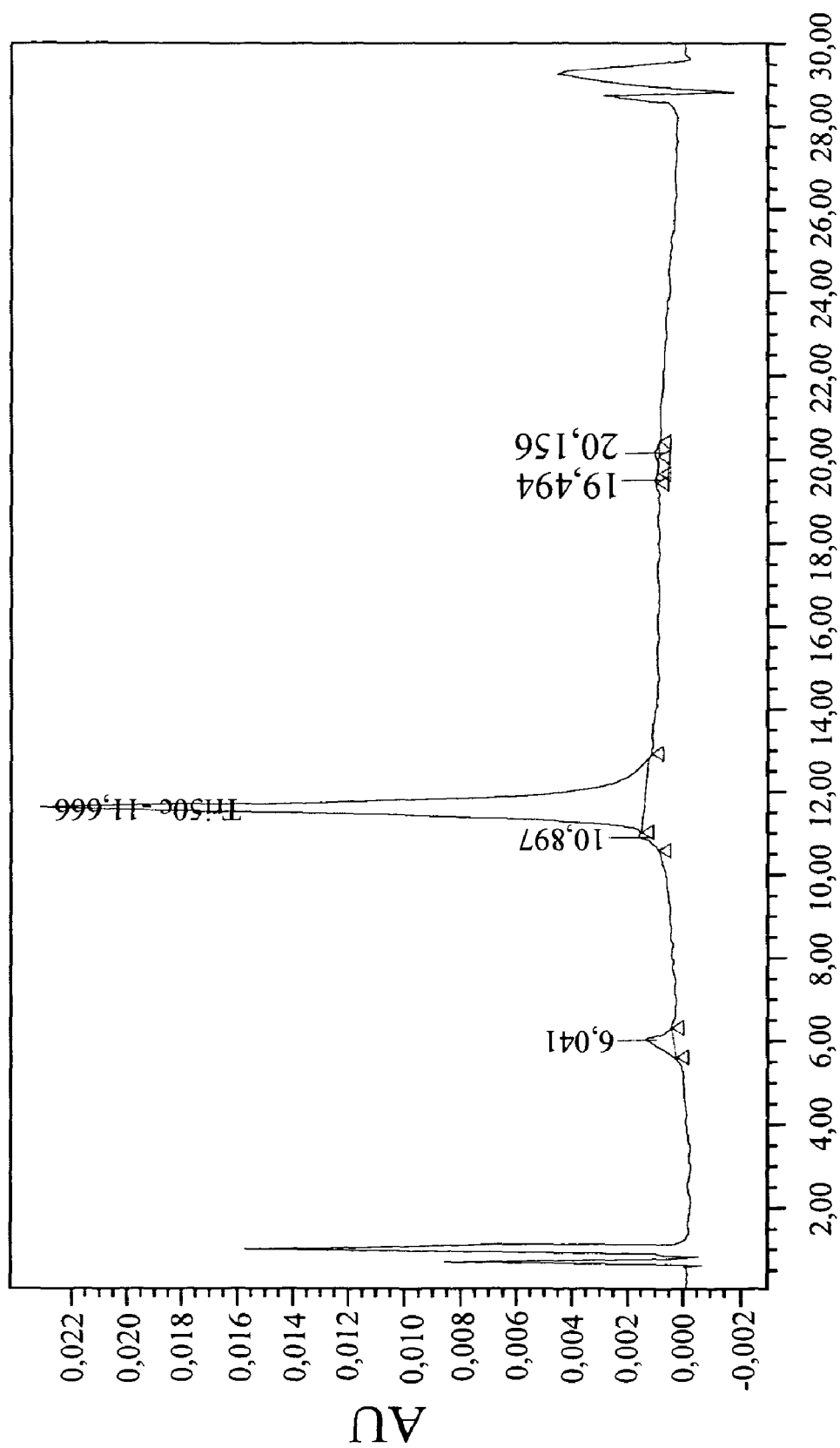
FIG. 3 is an HPLC plot referred to in Example 13, showing an impurity profile of encapsulated TRI 50c calcium salt after having been maintained absent blister packaging for 1.5 month at 40° C. and 75% relative humidity.

The corresponding HPLC trace is shown in FIG. 3.

Example 14

In-Vitro Assay as Thrombin Inhibitor of Magnesium Salt of TRI 50C

Thrombin Amidolytic Assay

TRI 50c magnesium salt (TRI 1405) was tested in a thrombin amidolytic assay.

Reagents:

Assay Buffer:
100 mM Na phosphate
200 mM NaCl (11.688 g/l)
0.5% PEG 6000 (5 g/l)
0.02% Na azide
pH 7.5

Chromogenic substrate S2238 dissolved to 4 mM (25 mg+10 ml) in water. Diluted to 50 uM with assay buffer for use in assay at 5 µM. (S2238 is H-D-Phe-Pip-Arg-pNA).

Thrombin obtained from HTI, via Cambridge Bioscience, and aliquoted at 1 mg/ml with assay buffer. Dilute to 100 ng/ml with assay buffer and then a further 1 in 3 for use in the assay.

Figure 4:
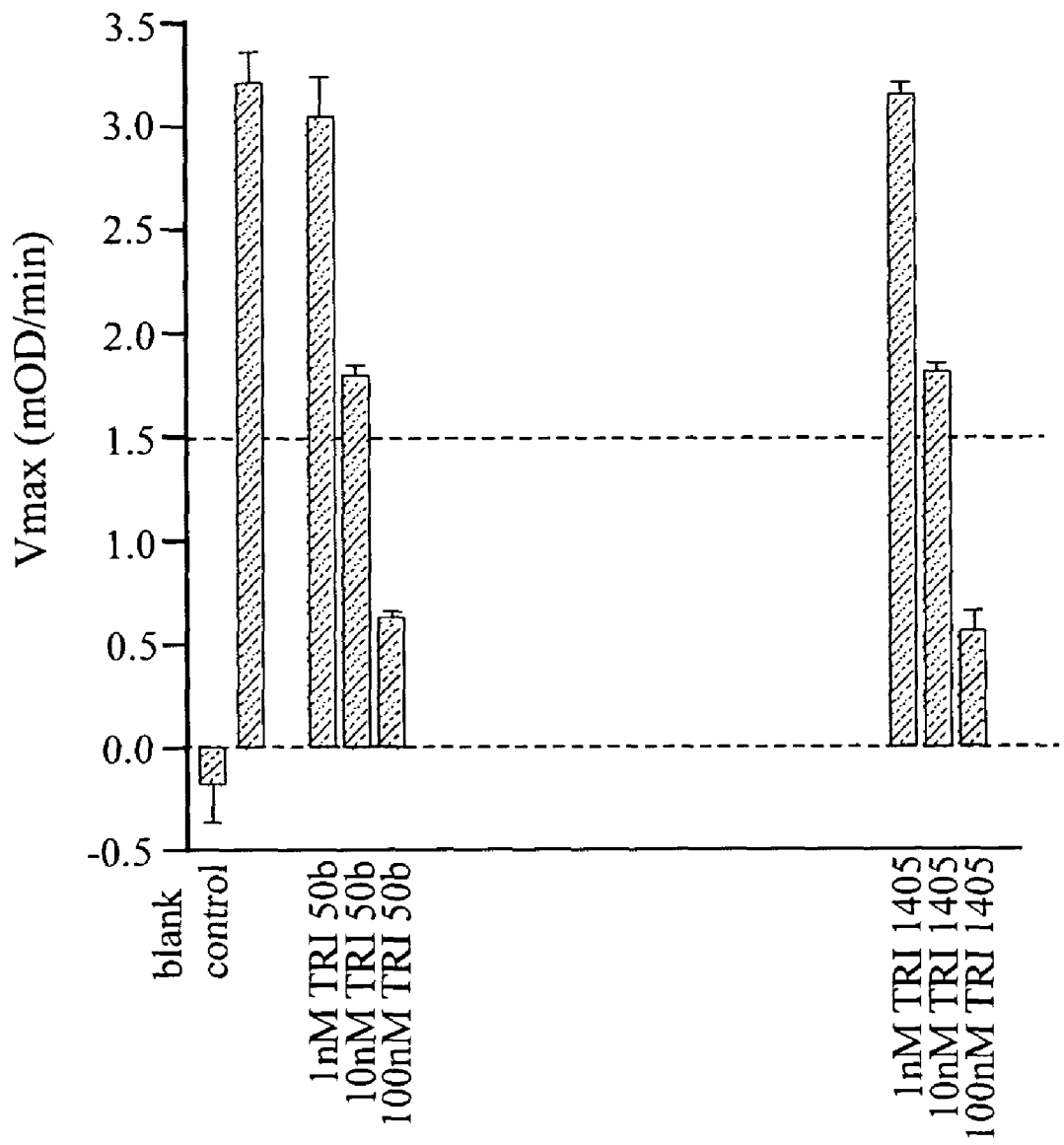
FIG. 4 is a chart referred to in Example 14, showing the results of a thrombin amidolytic assay of TRI 1405 (TRI 50c magnesium salt) and TRI 50b, where Vmax is the maximum rate of reaction measured by amidolytic assay.

Assay:
110 µl assay buffer
50ul 5 µg/ml thrombin
20 µl vehicle or compound solution
5 minutes at 37° C.
20 µl 50 µM S2238
Read at 405 nm at 37° C. for 10 minutes and record Vmax Results:
The results are presented in FIG. 4.

Discussion:
In this assay the magnesium salt of TRI 50c shows the same activity as TRI 50b as an external control.

Example 15 (Comparative)

Preparation of Potassium Salt of TRI 50C

Cbz-Phe-Pro-BoroMpg-OH (20.00 g, 38.1 mM) is dissolved in acetonitrile (200 ml) with stirring at room temperature. To this solution is added KOH as a 0.2M solution in distilled water (190 ml). The resultant clear solution is stirred for 2 hours at room temperature and then evacuated to dryness under vacuum with its temperature not exceeding 37° C. The resultant oil/tacky liquid is redissolved in 1 L distilled water with warming to 37° C. for about 2 hours. The solution is filtered through filter paper and evacuated to dryness, again with the temperature of the solution not exceeding 37° C. The resultant product is dried under vacuum overnight to normally yield a white brittle solid.

Yield: 14.45 mg.

The salt was then dried under vacuum over silica to constant weight (72 h).

Microanalysis:

| C % Found (Calc.) | H % Found (Calc.) | N % Found (Calc.) | B % Found (Calc.) | Metal % Found (Calc.) |
|---|---|---|---|---|
| 54.84 (57.55) | 6.25 (6.26) | 7.02 (7.45) | 2.01 (1.92) | K 4.29 (6.94) |

Example 16 (Comparative)

Aqueous Solubility of Potassium Salt of TRI 50C

The UV/visible spectra of TRI 50c and its solubility were obtained as described above in relation to the calcium salt. Solubility when dissolved at 25 mg/ml: 29 mM (16 mg/ml).

Example 17 (Comparative)

Solubility of TRI 50C

The UV/visible spectra of TRI 50c and its solubility were obtained as described above in relation to the calcium salt. The solubility of TRI 50c when dissolved at 50 mg/ml was 8 mM (4 mg/ml).

Example 18

Intraduodenal Absorption in Rat

A. Preparation of Liquid Formulations of TRI 50c and Salt

1. Preparation of Buffer Solution pH 4.5

Place 1.48 g of sodium acetate (anhydrous) in a 1000 mL volumetric flask, add 16 mL 2N CH$_3$COOH, then add water and mix. Adjust the pH to 4.5 using 0.2 N NaOH and fill up with water.

2. Preparation of Buffer Solution pH 6.8 (USP)

Place 50.0 mL monobasic potassium phosphate 0.2 M in a 200 mL volumetric flask add 22.4 mL NaOH 0.2 M fill up with dest. Water. Check the pH and adjust if necessary.

3. Preparation of the Formulation
   Place 10 mg of the relevant compound in an Eppendorf cup
   Add 0.5 mL ethanol and shake for 10 minutes
   Sonicate for 10 minutes
   Add 1.5 mL of buffer
   Shake for additional 15 minutes
   Resulting target concentration: 5 mg/mL B. Intraduodenal Studies The intraduodenal studies were performed using male Wistar rats, approximately 8 weeks of age and weighing between 250 and 300 g.

Food was withheld overnight prior to dosing and returned approximately 2 hours post-dose. Water was available ad libitum.

Animals were anaesthetised using gaseous halothane. A small incision was made in the abdomen and the duodenum located. Each animal received a single administration of control or test article by injection directly into the duodenum, using a constant dose volume of 4 mL/kg. Following administration the incision was closed using surgical staples.

Individual dose volumes were based on individual body weights, obtained on the day of dosing.

Treatments employed for the study were as follows:

| Treatment | Dose level (mg/kg) | Formulation concentration (mg/mL) | Number of animals |
|---|---|---|---|
| TRI 50 c control | 20 | 5 | 5 |
| Calcium salt | 20 | 5 | 5 |
| Potassium salt comparator | 20 | 5 | 5 |

Approximately 0.6 mL of blood was collected via a tail vein into 3.8% tri sodium citrate tubes approximately 48 hours prior to dosing and again at 0.5, 1, 2, 4 and 8 hours post-dose.

Plasma was prepared by centrifugation at 3000 rpm for 10 minutes at 4° C. Plasma was stored frozen (nominally −20° C.) prior to analysis in an automated coagulometer.

C. Results

TABLE 2

Mean thrombin time for intraduodenally dosed rats

| Treatment | Dose (mg/kg) | Group mean thrombin time (s ± sd) at time (hour) | | | | | |
|---|---|---|---|---|---|---|---|
| | | −48 | 0.5 | 1 | 2 | 4 | 8 |
| TRI 50 c control | 20 | 21.3 ± 2.69 | 42.1 ± 19.54 | 27.5 ± 9.42 | 23.5 ± 6.40 | 21.8 ± 2.33 | 21.5 ± 2.67 |
| Calcium salt | 20 | 21.6 ± 1.77 | 42.0 ± 6.74 | 34.0 ± 1.89 | 22.6 ± 5.10 | 24.4 ± 2.41 | 22.4 ± 1.73 |
| Potassium salt comparator | 20 | 20.0 ± 1.92 | 26.5 ± 3.64 | 24.4 ± 3.35 | 23.2 ± 0.83 | 23.2 ± 2.36 | 21.6 ± 0.70 | sd = standard deviation

Example 19

Oral Absorption in Rat

A. Preparation of Liquid Formulations of TRI 50c and Salt
   The procedure of Example 18 was followed.

B. Oral Studies

The per-oral studies were performed using male Wistar rats, approximately 8 weeks of age and weighing between 250 and 300 g.

Food was withheld overnight prior to dosing and returned approximately 2 hours post-dose. Water was available ad libitum.

Each animal received a single administration of control or test article by oral gavage, using a constant dose volume of 4 mL/kg.

Individual dose volumes were based on individual body weights, obtained on the day of dosing.

Treatments employed for the study were as follows:

| Treatment | Dose level (mg/kg) | Formulation concentration (mg/mL) | Number of animals |
|---|---|---|---|
| TRI 50c control | 20 | 5 | 5 |
| Calcium salt | 20 | 5 | 5 |
| Potassium salt comparator | 20 | 5 | 5 |

Approximately 0.6 mL of blood was collected via a tail vein into 3.8% tri sodium citrate tubes approximately 48 hours prior to dosing and again at 0.5, 1, 2, 4 and 8 hours post-dose.

Plasma was prepared by centrifugation at 300 rpm for 10 minutes at 4° C. Plasma was stored frozen (nominally −20° C.) prior to analysis in an automated coagulometer.

C. Results

TABLE 3 mean thrombin times in the rat following oral administration

| Treatment | Dose (mg/kg) | Group mean thrombin times (s ± sd) at time (hour) | | | | | |
|---|---|---|---|---|---|---|---|
| | | −48 | 0.5 | 1 | 2 | 4 | 8 |
| TRI 50c control | 20 | 22.9 ± 2.28 | 26.8 ± 1.96 | 23.3 ± 3.68 | 23.9 ± 2.25 | 23.1 ± 2.70 | 25.1 ± 0.33 |
| Calcium salt | 20 | 23.4 ± 1.25 | 25.9 ± 3.05 | 25.7 ± 1.94 | 24.3 ± 0.98 | 25.0 ± 1.31 | 22.9 ± 3.46 |
| Potassium salt comparator | 20 | 22.0 ± 1.40 | 24.7 ± 2.18 | 24.1 ± 1.87 | 22.9 ± 3.29 | 23.2 ± 1.24 | 23.8 ± 1.79 | sd = standard deviation

Example 20

Intraduodenal Variation

The thrombin times determined in example 18 were analysed to determine the standard deviation for increase in thrombin time, expressed as a percentage of the mean value (this is sometimes called the 'coefficient of variation'). The variation for the Ca salt was calculated to be less than for TRI 50c, as shown in Table 4 below.

TABLE 4

Thrombin times in rats dosed intraduodenally

| Product | Time | | | | |
|---|---|---|---|---|---|
| | 0 h | 0.5 h | increase | | |
| TRI 50c | 23.70 | 40.02 | 16.32 | | |
| | 23.10 | 40.20 | 17.10 | | |
| | 16.85 | 23.60 | 6.75 | | |
| | 21.67 | 62.55 | 40.88 | SD | SD % |
| | | Mean | 20.26 | 14.53 | 71.7% |
| Ca Salt | 21.97 | 35.32 | 13.35 | | |
| | 18.75 | 45.98 | 27.23 | | |
| | 23.57 | 37.27 | 13.70 | | |
| | 21.57 | 49.30 | 27.73 | SD | SD % |
| | | Mean | 20.50 | 8.06 | 39.3% |

CONCLUSION

Examples 18 and 19 indicate that multivalent metal salts of boronic acids have a high oral bioavailability involving an unknown technical effect not linked to solubility.

Example 20 indicates that multivalent metal salts of boronic acids have a low variation in oral bioavailability involving an unknown technical effect not linked to solubility.

It is speculated that the technical effects may in some way involve coordination between the boronate group and the metal ion.

Example 21

Oral Administration in Dog

The pharmacokinetics (PK) and pharmacodynamics (PD) of TRI 50c (free acid) and its calcium salt were studied in beagle dogs following oral administration. Three female and three male dogs were used for each leg of the study. The weight range of the dogs was 8–18 kg.

The PD was measured as thrombin time and APTT using an automated coagulometer. Plasma concentrations were measured using an LCMS/MS method.

The calcium salt and TRI 50c were filled into gelatine capsules and enterically coated (HPMCP 55). The dose was tailored on an individual basis for each dog. Blood samples were taken into tri-sodium citrate as previously at pre dose, 0.5, 1, 1.5, 2, 3, 6, 8, 12, 16 and 24 hours post dose.

A. RESULTS

A.1 Tolerance

The TRI 50c and the calcium salt were both tolerated well with no adverse events for the total duration of the study.

A.2 Calcium Salt

Unexpectedly high mean thrombin-clotting times were noted in dogs receiving the calcium salt. C max was observed three hours post dose with a mean thrombin clotting time of 80.5 seconds (raised from a base line of 15 seconds). There was still elevation of mean thrombin clotting times 8 hours post dose (mean of 20.2 seconds). All dogs responded dynamically following oral administration of the calcium salt, although there was some variability in response. All dogs dosed with the calcium salt achieved peak thrombin clotting times of up to 148 seconds, although the majority of animals (four out of six) achieved at least a four times elevation in peak thrombin time.

A.3 TRI 50c

Absorption as estimated by examination of dynamic response (TT) was variable. A peak thrombin time was noted 1.5 hours post dose (34.2 seconds from a base line of 15.4 seconds). Two animals failed to significantly absorb TRI 50c as estimated from their dynamic responses.

B. Activated Partial Thromboplastin Times

There were no significant changes in APTT from base line following administration of TRI 50c. There was a very slight mean elevation in APTT at 3 hours following administration of the calcium salt (14.5 seconds to 18 seconds at peak) this rise was deemed not to be clinically relevant.

C. Bioavailability

An estimation of bioavailability was achieved by a conversion of thrombin clotting times following administration of the calcium salt to estimated plasma concentrations.

Unexpectedly high absorption of the calcium salt was seen following oral absorption although there was some variability in responses; mean estimated bioavailability including two lower responders was 25% and as high as 50% in some animals. TRI 50c was also well tolerated orally although the dynamic responses were significantly less than those for the calcium salt.

Example 22

TRI 50B Inhibition of Platelet Procoagulant Activity

Platelet pro-coagulant activity may be observed as the increase, in rate of activation of prothrombin by factor Xa in the presence of factor Va upon the addition of platelets pretreated with thrombin, caused by thrombin alone, collagen alone or a mixture of thrombin and collagen. This property is due to an increase in anionic phospholipid on the surface of the platelet with concomitant release of microvesicle from the surface. This is an essential physiological reaction and people whose platelets have reduced ability to generate procoagulant activity (Scott syndrome) show an increased tendency for bleeding.

Method:

Washed platelets were treated with either 1.15 nM thrombin, 23 μg/ml collagen or a mixture of both at the same concentration at 37° C. TRI 50b was added either for 1 minute prior to the addition of activator or immediately after the incubation with activator. Platelet procoagulant activity was determined as described previously (Goodwin C A et al, Biochem J. 8(308):15–21, 1995).

TRI 50b proved to be a potent inhibitor of platelet procoagulant activity with $IC_{50}$'s as summarised below:

Table 5: Influence of TRI 50b on the induction of platelet procoagulant activity by various agonists:

TABLE 5

| Agonist | Fold acceleration without TRI 50b | IC50 plus pre-incubation (nM) | IC50 without incubation (nM) |
|---|---|---|---|
| Thrombin | 30 | 8 | 3000 |
| Collagen | 45 | 200 | 300 |
| Thrombin/Collagen | 110 | 3 | 80 |

Table 5 records, for example, that when platelets were treated with thrombin they caused a 30-fold acceleration of the rate of activation of prothrombin in comparison with control platelets. Treatment with TRI 50 reduced such acceleration by half at the various TRI 50 concentration levels given. The significant potency of TRI 50 is evidenced by the fact that the $IC_{50}$ values are in the nanomolar range.

TRI 50b does not have an effect on ADP, collagen or epinephrine induced aggregation of washed platelets.

Example 23

Rabbit Extracorporeal Shunt Model

Introduction

The technique describes an animal model in which a platelet rich thrombus is produced. The activity of TRI 50b and heparin are compared.

The carotid artery and jugular vein of anaesthetised rabbits were used to create an extracorporeal circuit containing a suspended foreign surface (silk thread). Thrombus deposition is initiated by creation of high sheer stress turbulent arterial blood flow, platelet activation, followed by coagulation in the presence of thrombogenic surfaces. Histopathological studies have shown that the thrombus is platelet rich.

Materials and Methods

Animals:

NZW rabbits (males 2.5–3.5 kg) were used. The animals were allowed food and water up to the induction of anaesthesia.

Anaesthesia:

Animals were premedicated with fontanel/fluanisone (Hypnorm) 0.15 ml total by intramuscular injection. General anaesthesia was induced with methohexitone (10 mg/ml) to effect, followed by endotracheal intubation. Anaesthesia was maintained with isoflurane (1–2.0%) carried in oxygen/nitrous oxide.

Surgical Preparation:

The animals were placed in dorsal recumbency and the ventral cervical region prepared for surgery. The left carotid artery and right jugular vein were exposed. The artery was cannulated with a large Portex® catheter (yellow gauge), cut to a suitable length. The vein was cannulated with a Silastic® catheter. The shunt comprised of a 5 cm length of 'auto analyser' line (purple/white gauge). Joins to the shunt on the arterial side were made with intermediate size Silastic® tubing. The shunt was filled with saline before exposure to the circulation. The right femoral artery was cannulated for the measurement of blood pressure.

Thread Preparation and Insertion:

The central section of the shunt contained a thread 3 centimeters in length. This consisted of 000 gauge Gutterman sewing silk so as to give four strands with a single knot at the end. (The knot section was outside the shunt).

Blood Flow

Blood flow velocity was determined by use of 'Doppler' probes (Crystal Biotech). A silastic probe was positioned over the carotid artery at the point of insertion of the arterial catheter. Flow was recorded on a chart recorder using heat sensitive paper.

Results

TABLE 6

| TREATMENT | DOSE | THROMBUS WEIGHT AFTER 20 minute run | ANTI-THROMBOTIC ACTIVITY |
|---|---|---|---|
| Control | N/A | 22.4 ± 2.2 mg (n = 5) | |
| TRI 50b | 10 mg/kg iv | 9.78 ± 1.9 mg (n = 5) | Active |
|  | 3.0 mg/kg iv | 15.3 ± 2.2 mg (n = 5) | Active |
| HEPARIN | 100 u/kg iv | 22.9 ± 1.65 mg (n = 4) | Inactive |
|  | 300 u/kg iv | 10.5 ± 1.4 mg (n = 4) | Active (Severe bleeding) |

Discussion

Table 6 shows that, under high arterial shear conditions, a TRI 50b dose of 3 mg/kg to 10 mg/kg iv significantly inhibits thrombus formation without bleeding, whereas a heparin dose within the normal clinical range for treating venous thrombosis (100 u/kg iv heparin) was ineffective. The higher dose of heparin, though active, caused severe bleeding. These results, which show TRI 50b effectively inhibiting arterial thrombosis without causing bleeding, are consistent with TRI 50b inhibiting platelet procoagulant activity. In contrast, the thrombin inhibitor heparin, when administered at an approximately equi-effective dose (in terms of inhibition of arterial thrombosis), produced the severe bleeding normal when thrombin inhibitors are used to treat arterial thrombosis.

Example 24

Comparison of Bleeding Times

The aim of the study was to compare the bleeding times of heparin with TRI 50b in a suitable model. It is accepted that heparin is a poor inhibitor of platelet procoagulant activity (*J. Biol. Chem.* 253(19):6908–16, 1978; Miletich J P, Jackson C M, Majerus PW1: *J. Clin. Invest.* 71(5): 1383–91, 1983).

Bleeding times were determined in a rat tail bleeding model following intravenous administration of heparin and TRI 50b. The doses employed were chosen on the basis of their efficacy in the rat Wessler and dynamic models and were as follows:

| | |
|---|---|
| TRI 50b: | 5 and 10 mg/kg |
| Heparin: | 100 units/kg |

Materials and Methods

Anaesthesia

Rats were anaesthetised with sodium pentabarbitone at 60 mg/kg (2.0 ml/kg of 30 mg/ml solution by ip. injection). Supplemental anaesthetic was given ip. as required.

Surgical Preparation

A jugular vein was cannulated for the administration of test compound. The trachea was also cannulated with a suitable cannula and the animals allowed to breathe 'room air' spontaneously.

Compound Administration

These were given in the appropriate vehicle at 1.0 ml/kg intravenously. Heparin was administered in saline, whilst TRI 50b was dissolved in ethanol, and then the resultant solution added to water for injection (1 part ethanol to 5 parts water).

Technique

Two minutes following compound administration the distal 2 mm of the animal's tail was sectioned with a new scalpel blade and the tail immersed in warm saline (37° C.) contained in a standard 'universal' container, so that the blood stream was clearly visible. The bleeding time recording was started immediately following transection until the cessation of blood flow from the tip of the tail. A period of 30 seconds was allowed after the blood flow from the tail had stopped to ensure that bleeding did not re-commence, if bleeding did start again the recording time was continued for up to a maximum of 45 minutes.

Results

Table 7 gives a summary of the bleeding results and shows the increases above base line values.

TABLE 7

Summary table of bleeding results

| Treatment | Bleeding time min (± SEM[†]) |
|---|---|
| Saline | 5.1 ± 0.6 |
| Heparin 100 u/kg iv | >40* |
| TRI 50b 5 mg/kg iv | 11.3 ± 1.2 |
| TRI 50b 10 mg/kg iv | 30.4 ± 5.2 |

*Severe bleeding in all animals, with no cessation after 40 minutes.
[†]SEM = standard error of the mean Discussion The results show that TRI 50b was superior to heparin (produced less bleeding) at all doses. It should be noted that when 100 u/kg heparin is compared with 5 mg/kg TRI 50b, heparin-treated animals bled more extensively than those receiving TRI 50b; it was previously established (Example 23) that heparin at a dose of 100 u/kg is a less effective inhibitor of arterial thrombosis than TRI 50b at a dose of 3.0 mg/kg. Heparin is primarily a thrombin inhibitor and a poor inhibitor of platelet procoagulant activity; the results are therefore consistent with TRI 50b exerting anti-coagulant activity by inhibition of platelet coagulant activity in addition to thrombin inhibiting activity.

Example 25

TRI 50B as a Prodrug for TRI 50C: Pharmacokinetics and Absorption

Materials and Methods

Animals

Rats, body weight circa 250–300 g were used. The animals were fasted only on the day of use for the iv stage. Animals were fasted on the night prior to study for the oral and intraduodenal studies, water was allowed up to the time of anaesthesia.

TABLE 8 oral phase

| Treatment | Dose mg/kg po | n |
|---|---|---|
| TRI 50b | 20 mg/kg | 2 |
| TRI 50c | 20 mg/kg | 2 |

TABLE 9 intraduodenal phase

| Treatment | Dose mg/kg po | n |
|---|---|---|
| TRI 50b | 20 mg/kg | 3 |
| TRI 50c | 20 mg/kg | 3 |

Dose

Formulation (TRI 50b/TRI 50c)

These were dosed in a formulation prepared as follows: 48 mg/ml of TRI 50b is dissolved in ethanol: PEG 300 (2:3 vol:vol). Just before administration, 5 volumes of this solution is mixed with 3 volumes of 5% kollidon 17 8F.

Both compounds were dosed by oral gavage, or directly into the duodenum, at 20 mg/kg.

The compounds were dosed in a PEG/ethanol/kollidon formulation which was prepared immediately before, as described immediately under the heading "Dose": Stock 15.0 mg/ml. This was dosed at 1.33 ml/kg (equivalent to 30 mg/kg).

Methods

Oral Gavage

Rats were dosed at 20 mg/kg. Approximately 30 minutes following dosing the rats were anaesthetised.

Intraduodenal Administration

The compounds were instilled directly into the duodenum after anaesthesia and surgical procedures had been completed.

Blood Sampling

Oral Phase

Blood (0.81 ml) was taken from the carotid cannula into (0.09 ml) of 3.8% w/v tri sodium citrate following anaesthesia and surgery. The first samples were taken one-hour post dose. Then at, 1.5, 2, 4 hours post dose.

Intraduodenal Phase

Blood samples were taken: Pre dose, then at 0.25, 0.5, 0.75, 1.0, 2, 3 and 4 hours post dosing.

Plasma

This was obtained by centrifugation (3000 RPM for 10 minutes) and stored at −20° C. prior to analysis.

Results

Pharmacokinetic Analysis

Figure 5:
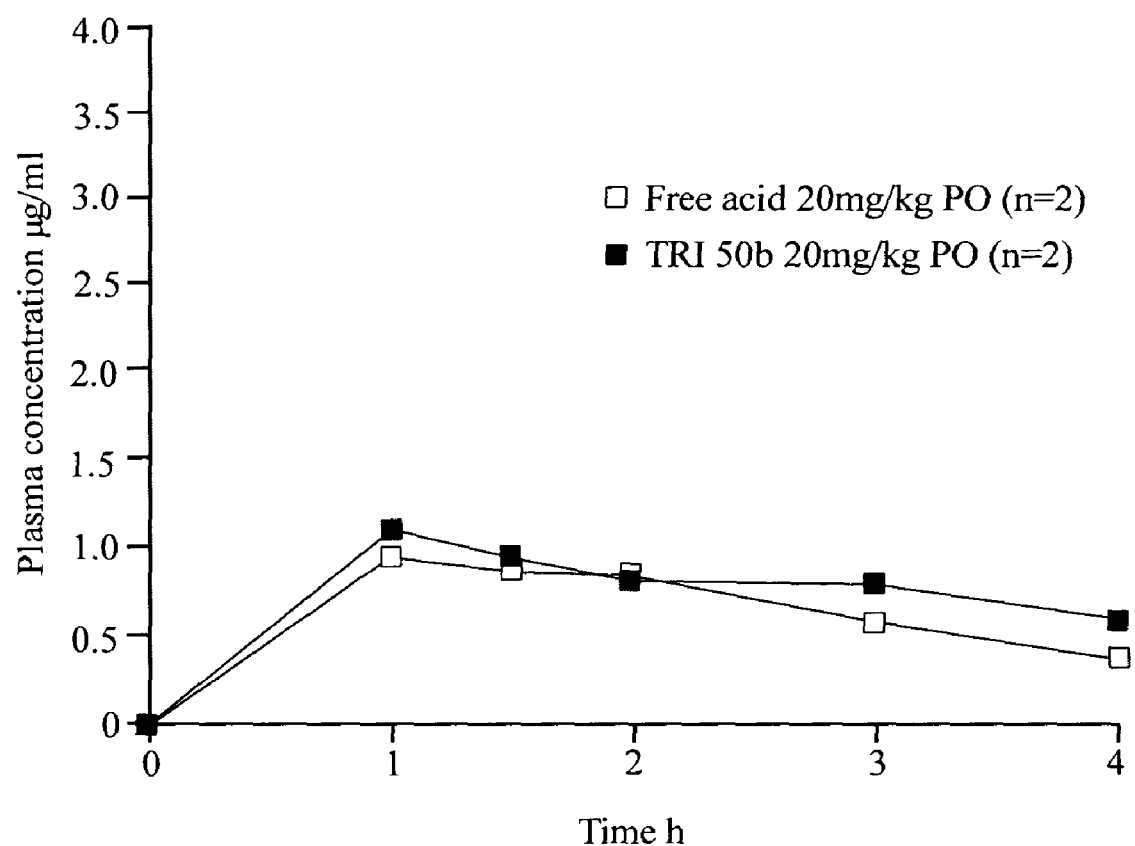
FIG. 5 is a plot referred to in Example 25, showing oral phase clearance and kinetics following p.o. dosing with TRI 50b or TRI 50c.

FIG. 5: oral phase clearance and kinetics following dosing with TRI 50b or its free acid (TRI 50c).

Figure 6:
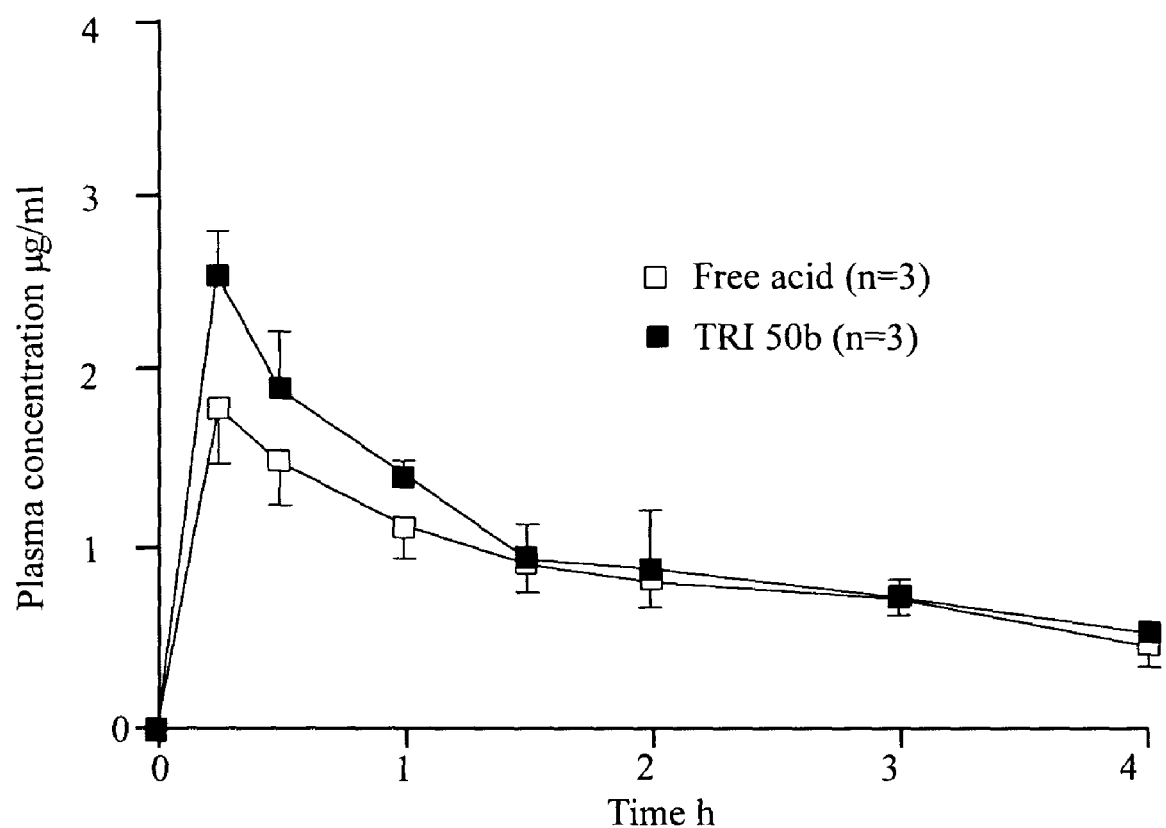
FIG. 6 is a second plot referred to in Example 25, showing oral phase clearance and kinetics following intraduodenal dosing with TRI 50b or TRI 50c.

FIG. 6: oral phase clearance and kinetics following intraduodenal dosing with TRI 50b or its free acid (TRI 50c).

CONCLUSION

When given by the intraduodenal route TRI 50b achieved a higher bioavailability (peak plasma concentration) than the free acid. The data are consistent with TRI 50b being rapidly hydrolysed in plasma to TRI 50c and with TRI 50c being the active principle.

Taken together with the data from examples 18 to 21, the results of examples 22 to 25 indicate that oral administration of TRI 50c as the calcium salt will provide an excellent way to treat arterial thrombosis and/or venous thrombosis.

Example 26

Human Clinical Studies

In human clinical volunteer studies with doses of up to 2.5 mg/kg i.v. (dosages which significantly prolong the thrombin clotting time), TRI 50b had no effect on Simplate bleeding time (i.e. bleeding time measured using a Simplate® bleeding time device).

It will be appreciated from the foregoing that boronic acid salts are described that are useful for pharmaceutical purposes and which feature one or more of the following attributes: (1) improved amount of oral bioavailability; (2) improved consistency of oral bioavailability; (3) improved stability; and (4), in any event, not suggested by the prior art.

The selection of active ingredient for a pharmaceutical composition is a complex task, which requires consideration not only of biological properties (including bioavailability) but also of physicochemical properties desirable for processing, formulation and storage. Bioavailability itself is dependent on various factors, often including in vivo stability, solvation properties and absorption properties, each in turn potentially dependent on multiple physical, chemical and/or biological behaviours.

The present disclosure includes the subject matter of the following paragraphs:

1. An oral pharmaceutical formulation comprising a salt of a pharmaceutically acceptable multivalent metal and an organoboronic acid drug.

2. A formulation of paragraph 1 wherein the metal is a Group II or Group III metal or zinc.

3. A formulation of paragraph 1 or paragraph 2 wherein the metal is divalent.

4. A formulation of paragraph 1 wherein the metal is calcium.

5. A formulation of paragraph 1 wherein the metal is magnesium.

6. A formulation of any of paragraphs 1 to 5 wherein the organoboronic acid is hydrophobic.

7. A formulation of any of paragraphs 1 to 6 wherein the organoboronic acid comprises a boropeptide or boropeptidomimetic.

8. A formulation of any of paragraphs 1 to 6 wherein the organoboronic acid is of the formula (I):

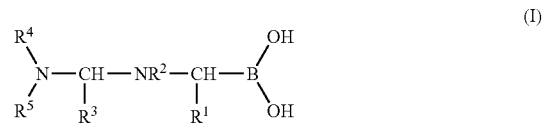

where:

$R^1$ is H or a non-charged side group;

$R^2$ is H or $C_1$–$C_{13}$ hydrocarbyl optionally containing in-chain oxygen or sulfur and optionally substituted by a substituent selected from halo, hydroxy and trifluoromethyl;

or $R^1$ and $R^2$ together form a $C_1$–$C_{13}$ moiety which in combination with N—CH forms a 4–6 membered ring and which is selected from alkylene (whether branched or linear) and alkylene containing an in-chain sulfur or linked to N—CH through a sulfur;

$R^3$ is the same as or different from $R^1$ provided that no more than one of $R^1$ and $R^2$ is H, and is H or a non-charged side group;

$R^4$ is H or $C_1$–$C_{13}$ hydrocarbyl optionally containing in-chain oxygen or sulfur and optionally substituted by a substituent selected from halo, hydroxy and trifluoromethyl;

or $R^3$ and $R^4$ together form a $C_1$–$C_{13}$ moiety which in combination with N—CH forms a 4–6 membered ring and which is selected from alkylene (whether branched or linear) and alkylene containing an in-chain sulfur or linked to N—CH through a sulfur; and $R^5$ is X-E- wherein E is nothing or a hydrophobic moiety selected from the group consisting of amino acids (natural or unnatural) and peptides of two or more amino acids (natural or unnatural) of which more than half are hydrophobic and X is H or an amino-protecting group.

9. A formulation of paragraph 8 where $R^2$ and $R^4$ are H, or $R^2$ is H and $R^3$ and $R^4$ together form a said $C_1$–$C_{13}$ moiety.

10. A formulation of paragraph 8 or paragraph 9 wherein said hydrocarbyl optionally containing in-chain oxygen or sulfur is selected from the group consisting of alkyl; alkyl substituted by cycloalkyl, aryl or heteroaryl; cycloalkyl; aryl; and heteroaryl.

11. A formulation of any of paragraphs 8 to 10 wherein E is nothing.

12. A formulation of any of paragraphs 8 to 10 wherein E is a hydrophobic amino acid.

13. A formulation of any of paragraphs 1 to 6 wherein the organoboronic acid is of the formula (II):

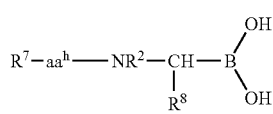
(II)

wherein $R^7$ is X-E'- wherein X is hydrogen or an amino-protecting group and E' is absent or is a hydrophobic amino acid;

$R^8$ is an optionally substituted moiety containing from 1 to 5 carbon atoms and selected from the group consisting of alkyl, alkoxy and alkoxyalkyl, the optional substituents being hydroxy and halogen (F, Cl, Br, I); and $aa^h$ is a hydrophobic amino acid, or is glycine N-substituted by a $C_1$–$C_{13}$ hydrocarbyl group optionally containing in-chain oxygen or sulfur and optionally substituted by a substituent selected from halo, hydroxy and trifluoromethyl.

14. A formulation of any of paragraphs 8 to 13 where X is $R^6$—$(CH_2)_p$—C(O)—, $R^6$—$(CH_2)_p$—S(O)$_2$—, $R^6$—$(CH_2)_p$—NH—C(O)— or $R^6$—$(CH_2)_p$—O—C(O)— wherein p is 0, 1, 2, 3, 4, 5 or 6 and $R^6$ is H or a 5 to 13-membered cyclic group optionally substituted by 1, 2 or 3 substituents selected from halogen, amino, nitro, hydroxy, a $C_5$–$C_6$ cyclic group, $C_1$–$C_4$ alkyl and $C_1$–$C_4$ alkyl containing, and/or linked to the cyclic group through, an in-chain 0, the aforesaid alkyl groups optionally being substituted by a substituent selected from halogen, amino, nitro, hydroxy and a $C_5$–$C_6$ cyclic group.

15. A formulation of paragraph 14 wherein said 5 to 13-membered cyclic group is aromatic or heteroaromatic.

16. A formulation of paragraph 15 wherein said 5 to 13-membered cyclic group is phenyl or a 6-membered heteroaromatic group.

17. A formulation of any of paragraphs 14 to 16 wherein X is $R^6$—$(CH_2)_p$—C(O)— or $R^6$—$(CH_2)_p$—O—C(O)— and p is 0 or 1.

18. A formulation of any of paragraphs 1 to 6 wherein the organoboronic acid is a serine protease inhibitor.

19. An oral pharmaceutical formulation comprising a salt of a pharmaceutically acceptable multivalent metal and an organoboronic acid inhibitor of a coagulation serine protease.

20. A formulation of paragraph 19 wherein the organoboronic acid is a peptide boronic acid.

21. A formulation of paragraph 19 or paragraph 20 wherein the organoboronic acid is a thrombin inhibitor.

22. A formulation of paragraph 21 wherein the thrombin inhibitor has a neutral thrombin S1-binding moiety linked to a hydrophobic thrombin S2/S3-binding moiety.

23. A formulation of paragraph 21 wherein the organoboronic acid is of Formula (III):

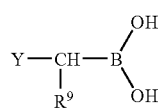
(III)

wherein

Y comprises a moiety which, together with the fragment —CH($R^9$)—B(OH)$_2$, has affinity for the substrate binding site of thrombin; and $R^9$ is a straight chain alkyl group interrupted by one or more ether linkages and in which the total number of oxygen and carbon atoms is from 3 to 6, or is —(CH$_2$)$_m$—W where m is from 2 to 5 and W is —OH or halogen (F, Cl, Br or I).

24. A formulation of paragraph 23 wherein Y comprises an amino add which binds to the S2 subsite of thrombin and is linked to —CH($R^9$)—B(OH)$_2$ by a peptide linkage, the amino acid being N-terminally linked to a moiety which binds the S3 subsite of thrombin.

25. A formulation of paragraph 23 wherein Y is an optionally N-terminally protected dipeptide residue which binds to the S3 and S2 binding sites of thrombin and is linked to —CH($R^9$)—B(OH)$_2$ by a peptide linkage, the peptide linkages in the acid optionally and independently being N-substituted by a $C_1$–$C_{13}$ hydrocarbyl group optionally containing in-chain oxygen or sulfur and optionally substituted by a substituent selected from halo, hydroxy and trifluoromethyl.

26. A formulation of paragraph 25 wherein the N-terminal protecting group is a group X as defined in any of paragraphs 13 to 17 (other than hydrogen).

27. A formulation of paragraph 25 or paragraph 26, wherein the organoboronic acid has an N-terminal protecting group and unsubstituted peptide linkages.

28. An oral pharmaceutical formulation comprising a salt of a pharmaceutically acceptable multivalent metal and a peptide boronic acid of formula (IV):

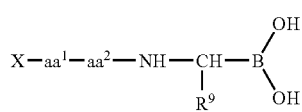
(IV)

where:

X is H (to form NH$_2$) or an amino-protecting group;

$aa^1$ is an amino acid residue having a hydrocarbyl side chain containing no more than 20 carbon atoms and comprising at least one cyclic group having up to 13 carbon atoms;

$aa^2$ is an imino acid residue having from 4 to 6 ring members;

$R^9$ is a straight chain alkyl group interrupted by one or more ether linkages and in which the total number of oxygen and carbon atoms is from 3 to 6, or is —(CH$_2$)$_m$—W where m is from 2 to 5 and W is —OH or halogen (F, Cl, Br or I).

29. A formulation of paragraph 28 wherein $aa^1$ has a hydrocarbyl side chain containing up to 13 C atoms.

30. A formulation of paragraph 28 wherein the cyclic group(s) of $aa^1$ is/are aryl groups.

31. A formulation of paragraph 28 wherein the cyclic group(s) of aa$^1$ is/are phenyl.

32. A formulation of paragraph 28 wherein aa$^1$ has a hydrocarbyl side chain containing one or two cyclohydrocarbyl groups.

33. A formulation of paragraph 28 wherein aa$^1$ is Phe, Dpa or a wholly or partially hydrogenated analogue thereof.

34. A formulation of paragraph 28 wherein aa$^1$ is selected from Dpa, Phe, Dcha and Cha.

35. A formulation of any of paragraphs 28 to 34 wherein aa$^1$ is of R-configuration.

36. A formulation of paragraph 35 wherein aa$^1$ is (R)-Phe (that is, D-Phe) or (R)-Dpa (that is, D-Dpa).

37. A formulation of paragraph 35 wherein aa$^1$ is (R)-Phe.

38. A formulation of any of paragraphs 28 to 37 wherein aa$^2$ is a residue of an imino acid of formula (V)

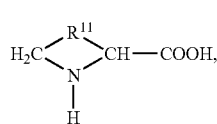     (V)

where R$^{11}$ is —CH$_2$—, CH$_2$—CH$_2$—, —S—CH$_2$— or —CH$_2$—CH$_2$—CH$_2$—, which group, when the ring is 5-6-membered, is optionally substituted at one or more —CH$_2$— groups by from 1 to 3 C$_1$–C$_3$ alkyl groups.

39. A formulation of paragraph 38 wherein aa$^2$ is of S-configuration.

40. A formulation of paragraph 38 wherein aa$^2$ is (S)-Pro.

41. A formulation of paragraph 28, wherein aa$^1$-aa$^2$ is (R)-Phe-(S)-Pro (that is, D-Phe-L-Pro).

42. A formulation of any of paragraphs 28 to 41 wherein R$^9$ is 2-bromoethyl, 2-chloroethyl, 2-methoxyethyl, 3-bromopropyl, 3-chloropropyl or 3-methoxypropyl.

43. A formulation of any of paragraphs 28 to 41 wherein R$^9$ is 3-methoxypropyl.

44. A formulation of paragraph 28 wherein the peptide boronic acid is a compound of formula (IX):

X—(R)-Phe-(S)-Pro-(R)-Mpg-B(OH)$_2$     (IX), where X is as defined in paragraph 28 or paragraph 24.

45. A formulation of any of paragraphs 28 to 44 wherein X is R$^{6'}$—(CH$_2$)$_p$—C(O)— or R$^{6'}$—(CH$_2$)$_p$—O—C(O)—, where R$^{6'}$ is phenyl or a 6-membered heteroaromatic group and p is 0 or 1.

46. A formulation of any of paragraphs 28 to 44 wherein X is benzyloxycarbonyl.

47. A formulation of any of paragraphs 28 to 46 wherein the salt is a divalent metal salt of the peptide boronic acid.

48. A formulation of paragraph 47 wherein the metal is calcium.

49. A formulation of paragraph 47 wherein the metal is magnesium.

50. A formulation of any of paragraphs 28 to 46 wherein the metal is a Group III metal salt of the peptide boronic acid.

51. A formulation of paragraph 50 wherein the metal is aluminium.

52. A formulation of paragraph 50 wherein the metal is gallium.

53. A formulation of any of paragraphs 1 to 52 which has a stoichiometry consistent with the boronate groups in the formulation predominantly carrying a single native charge.

54. A pharmaceutical composition adapted for oral administration and comprising a calcium salt of the compound:

Cbz-(R)-Phe-(S)-Pro-(R)-Mpg-B(OH)$_2$.

55. A formulation of paragraph 54 wherein the salt is an acid salt.

56. A formulation of any of paragraphs 1 to 55 wherein the salt comprises a boronate ion derived from the boronic acid and a counterion and wherein the salt consists essentially of a salt having a single type of counterion.

57. A formulation of any of paragraphs 1 to 56 which is in the form of a tablet or capsule.

58. A pharmaceutical formulation in oral dosage form comprising a salt as defined in any of paragraphs 1 to 56 and a pharmaceutically acceptable diluent, excipient or carrier.

59. A formulation of any of paragraphs 1 to 58 which is adapted to release the salt or the product in the duodenum.

60. A formulation of paragraph 59 which is enterically coated.

61. A salt of a pharmaceutically acceptable multivalent (at least divalent) metal and an organoboronic acid drug (where the term "drug" embraces prodrugs), wherein the observed stoichiometry is consistent with a predominant portion of the salt having a notional drug:metal stoichiometry of n:1, wherein n is the valency of the metal.

62. A salt of paragraph 61 wherein the observed stoichiometry is consistent with the salt consisting essentially of a salt having a notional drug:metal stoichiometry of V:1.

63. A salt of paragraph 61 or paragraph 62 which is as further defined by any of paragraphs 1 to 53 or 55.

64. A salt of a pharmaceutically acceptable multivalent metal and an organoboronic acid of Formula (III) as defined in any of paragraphs 23 to 27.

65. A salt of a pharmaceutically acceptable multivalent metal and a peptide boronic acid of formula (IV):

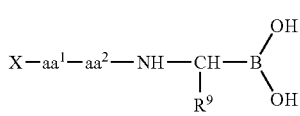     (IV)

where:

X is H (to form NH$_2$) or an amino-protecting group;

aa$^1$ is an amino acid residue having a hydrocarbyl side chain containing no more than 20 carbon atoms and comprising at least one cyclic group having up to 13 carbon atoms;

aa$^2$ is an imino acid residue having from 4 to 6 ring members;

R$^9$ is a straight chain alkyl group interrupted by one or more ether linkages and in which the total number of oxygen and carbon atoms is from 3 to 6, or is —(CH$_2$)$_m$—W where m is from 2 to 5 and W is —OH or halogen (F, Cl, Br or I).

66. A salt of paragraph 65 which is as further defined by the features of any of paragraphs 29 to 52, or a permissible combination thereof.

67. A calcium salt of the compound Cbz-(R)-Phe-(S)-Pro-(R)-Mpg-B(OH)$_2$.

68. A calcium salt of paragraph 67 which has an observed stoichiometry (compound:calcium) substantially of 2:1.

69. A composition of matter for use in preparing a salt of any of paragraphs 65 to 68 comprising an alkali metal salt of an organoboronic acid as defined in any of paragraphs 28 to 46 or 54.

70. A sodium salt of a compound of Formula (IV) as defined in any of paragraphs 23 to 46 or 54.

71. A potassium salt of a compound of Formula (IV) as defined in any of paragraphs 23 to 46 or 54.

72. A salt of any of paragraphs 57 to 59 when in aqueous solution.

73. A method of inhibiting a coagulation serine protease in the treatment of disease comprising orally administering to a mammal a therapeutically effective amount of a product selected from the group consisting of the formulations of any of paragraphs 19 to 60 and the salts of any of paragraphs 64 to 68.

74. A method of paragraph 73 wherein the active agent is in a formulation adapted to release the active agent in the duodenum.

75. The use of a salt of any of paragraphs 64 to 68 for the manufacture of an oral medicament for treating, for example preventing, thrombosis.

76. A method of treating venous and/or arterial thrombosis by prophylaxis or therapy, comprising administering to a mammal suffering from, or at risk of suffering from, venous and/or arterial thrombosis a therapeutically effective amount of a product selected from the formulation of any of paragraphs 23 to 60 and the salt of any of paragraphs 64 to 68.

77. A method of paragraph 76 wherein the disease is an acute coronary syndrome.

78. A method of paragraph 76 wherein the disease is acute myocardial infarction.

79. A method of paragraph 76 wherein the disease is a venous thromboembolic event, selected from the group consisting of deep vein thrombosis and pulmonary embolism.

80. A method for preventing thrombosis in a haemodialysis circuit of a patient, comprising administering to the patient a therapeutically effective amount of a product selected from the formulations of any of paragraphs 23 to 60 and the salt of any of paragraphs 64 to 68.

81. A method for preventing a cardiovascular event in a patient with end stage renal disease, comprising administering to the patient a therapeutically effective amount of a product selected from the formulations of any of paragraphs 23 to 60 and the salt of any of paragraphs 64 to 68.

82. A method for preventing venous thromboembolic events in a patient receiving, or intended to receive, chemotherapy through an indwelling catheter, comprising administering to the patient a therapeutically effective amount of a product selected from the formulations of any of paragraphs 23 to 60 and the salt of any of paragraphs 64 to 68.

83. A method for preventing thromboembolic events in a patient undergoing, or intended to undergo, a lower limb arterial reconstructive procedure, comprising administering to the patient a therapeutically effective amount of a product selected from the formulation of any of paragraphs 23 to 60 and the salt of any of paragraphs 64 to 68.

84. A method of inhibiting platelet procoagulant activity, comprising administering to a mammal at risk of, or suffering from, arterial thrombosis a therapeutically effective amount of a product selected from the formulations of any of paragraphs 23 to 60 and the salt of any of paragraphs 64 to 68.

85. A method of paragraph 84 wherein the disease is an acute coronary syndrome.

86. A method of treating by way of therapy or prophylaxis an arterial disease selected from acute coronary syndromes, cerebrovascular thrombosis, peripheral arterial occlusion and arterial thrombosis resulting from atrial fibrillation, valvular heart disease, arterio-venous shunts, indwelling catheters or coronary stents, comprising administering to a mammal a therapeutically effective amount of a product selected from the formulations of any of paragraphs 23 to 60 and the salt of any of paragraphs 64 to 68.

87. A method of paragraph 86 wherein the disease is an acute coronary syndrome.

88. The use of a salt of any of paragraphs 64 to 68 for the manufacture of an oral medicament for a treatment recited in any of paragraphs 73 and 75 to 87.

89. A pharmaceutical formulation comprising a combination of (i) a salt of any of paragraphs 64 to 68 and (ii) a further pharmaceutically active agent.

90. A pharmaceutical formulation comprising a combination of (i) a salt of any of paragraphs 64 to 68 and (ii) another cardiovascular treatment agent.

91. A formulation of paragraph 90 wherein the other cardiovascular treatment agent comprises a lipid-lowering drug, a fibrate, niacin, a statin, a CETP inhibitor, a bile acid sequestrant, an anti-oxidant, a IIb/IIIa antagonist, an aldosterone inhibitor, an adenosine A2 receptor antagonist, an adenosine A3 receptor agonist, a beta-blocker, acetylsalicylic acid, a loop diuretic, an ace inhibitor, an antithrombotic agent with a different mechanism of action, an antiplatelet agent, a thromboxane receptor and/or synthetase inhibitor, a fibrinogen receptor antagonist, a prostacyclin mimetic, a phosphodiesterase inhibitor, an ADP-receptor ($P_2$.T) antagonist, a thrombolytic, a cardioprotectant or a COX-2 inhibitor.

92. The use of a salt as defined in any of paragraphs 23 to 60 for the manufacture of a medicament for treating, for example preventing, a cardiovascular disorder in co-administration with another cardiovascular treatment agent.

93. A product comprising an adduct of a compound of Formula (IX) as defined in paragraph 44 and diethanolamine.

94. A composition of matter comprising:
(i) a species of formula (X)

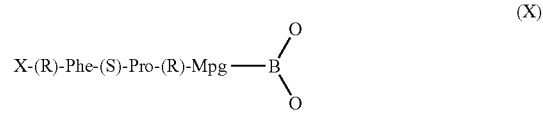

wherein X is H or an amino protecting group, the boron atom is optionally coordinated additionally with a nitrogen atom, and the valency status of the terminal oxygens is open (they may be attached to a second covalent bond, be ionised as —O⁻, or have some other, for example intermediate, status); and, in bonding association therewith (ii) a species of formula (XI)

wherein the valency status of the nitrogen atom and the two oxygen atoms is open.

95. A composition of paragraph 94, wherein the terminal oxygen atoms of the species of formula (X) and the oxygen atoms of the species of formula (XI) are the same oxygen atoms, i.e. the species of formula (XI) forms a diol ester with the species of formula (X).

96. A medicament comprising a salt of a pharmaceutically acceptable divalent metal and an organoboronic acid which is a selective thrombin inhibitor and has a neutral thrombin S1 subsite-binding moiety.

97. A medicament of paragraph 96 wherein the selective thrombin inhibitor is an organoboronic acid of Formula (III) as defined in any of paragraphs 23 to 27.

98. A medicament of paragraph 96 or paragraph 97 wherein the selective thrombin inhibitor has a Ki for thrombin of about 100 nM or less.

99. A medicament of paragraph 98 wherein the selective thrombin inhibitor has a Ki for thrombin of about 20 nM or less.

100. A method of stabilising an organoboronic acid, comprising providing it in the form of a multivalent salt thereof.

101. A method of formulating an organoboronic acid drug to increase the stability of the drug species, comprising formulating the acid in the form of an acid salt thereof with a multivalent metal.

What is claimed is:

1. A salt of a pharmaceutically acceptable multivalent metal and an organoboronic acid inhibitor of thrombin having a neutral thrombin S1-binding moiety linked to a hydrophobic thrombin S2/S3-binding moiety.

2. A salt of claim 1 wherein the organoboronic acid is of Formula (III):

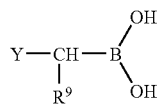

(III)

wherein
Y comprises a moiety which, together with the fragment —CH($R^9$)—B(OH)$_2$, has affinity for the substrate binding site of thrombin; and
$R^9$ is a straight chain alkyl group interrupted by one or more ether linkages and in which the total number of oxygen and carbon atoms is from 3 to 6, or is —(CH$_2$)$_m$—W where m is from 2 to 5 and W is —OH or halogen (F, Cl, Br or I).

3. A salt of claim 2 wherein $R^9$ is an alkoxyalkyl group.

4. A salt of claim 2 wherein Y comprises an amino acid which binds to the S2 subsite of thrombin and is linked to —CH(R9)—B(OH)$_2$ by a peptide linkage, the amino acid being N-terminally linked to a moiety which binds the S3 subsite of thrombin.

5. A salt of claim 4 wherein Y comprises an N-terminally protected dipeptide residue which binds to the S3 and S2 binding sites of thrombin and is linked to —CH(R9)—B (OH)$_2$ by a peptide linkage.

6. The salt of claim 1 wherein the boronic acid has a Ki for thrombin of about 100 nM or less.

7. The salt of claim 5 wherein the Y dipeptide is N-terminally protected or N-terminally unprotected, and the peptide linkages in the dipeptide are unsubstituted or independently N-substituted by a C$_1$–C$_{13}$ hydrocarbyl, wherein the C$_1$–C$_{13}$ hydrocarbyl contains no heteroatoms or at least one in-chain or in-ring nitrogen, oxygen or sulfur atom, and the C$_1$–C$_{13}$ hydrocarbyl is unsubstituted or substituted by a substituent selected from halo, hydroxy and trifluoromethyl.

8. The salt of claim 1 wherein the multivalent metal comprises calcium, magnesium or zinc.

9. The salt of claim 1 wherein the salt consists essentially of an acid salt in which one B—OH group of formula (I), when trigonally represented, remains protonated.

10. The salt of claim 7 wherein the salt comprises boronate ions derived from the peptide boronic acid and has a stoichiometry consistent with the boronate ions carrying a single negative charge.

11. The salt of claim 3 wherein the salt consists essentially of a hemicalcium or hemimagnesium salt of the boronic acid.

12. The salt of claim 1 wherein the peptide boronic acid is of formula (IV):

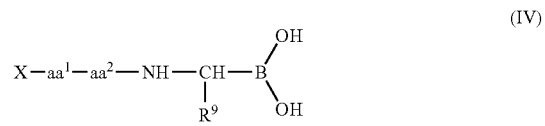

(IV)

where:
X is H or an amino-protecting group;
aa$^1$ is an amino acid having a hydrocarbyl side chain containing no more than 20 carbon atoms and comprising at least one cyclic group having up to 13 carbon atoms;
aa$^2$ is an imino acid having from 4 to 6 ring members;
$R^9$ is a straight chain alkyl group interrupted by one or more ether linkages and in which the total number of oxygen and carbon atoms is from 3 to 6, or is —(CH$_2$)$_m$—W where m is from 2 to 5 and W is —OH or halogen.

13. The salt of claim 12 wherein aa$^1$ is selected from Phe, Dpa and wholly or partially hydrogenated analogues thereof.

14. The salt of claim 13 wherein aa$^1$ is of R-configuration.

15. The salt of claim 12 wherein aa$^2$ is a residue of an imino acid of formula (V)

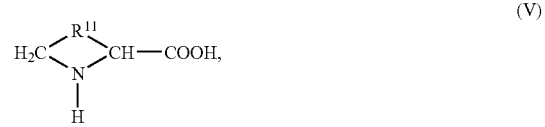

(V)

where $R^{11}$ is —CH$_2$—, —CH$_2$—CH$_2$—, —S—CH$_2$—, —S—C(CH$_3$)$_2$— or —CH$_2$—CH$_2$—CH$_2$—, and, when the formula (V) ring is 5- or 6-membered, the formula (V) ring is unsubstituted or is substituted at one or more —CH$_2$— groups by from 1 to 3 C$_1$–C$_3$ alkyl groups.

16. The salt of claim 15 wherein aa$^2$ is of S-configuration.

17. The salt of claim 12, wherein aa$^1$-aa$^2$ is (R)-Phe-(S)-Pro and the fragment —NH—CH(R$^1$)—B(OH)$_2$ is of R-configuration.

18. The salt of claim 13 wherein the boronic acid is of formula (IX):

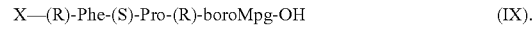

X—(R)-Phe-(S)-Pro-(R)-boroMpg-OH            (IX).

wherein X is $R^6$—(CH$_2$)$_p$—C(O)—, $R^6$—(CH$_2$)$_p$—S(O)$_2$—, $R^6$—(CH$_2$)$_p$—NH—C(O)— or $R^6$—(CH$_2$)$_p$—O—C(O)— wherein p is 0, 1, 2, 3, 4, 5 or 6 and $R^6$ is H or a 5 to 13-membered cyclic group which is unsubstituted or substituted by 1, 2 or 3 substituents selected from halogen; amino; nitro; hydroxy; a C$_5$–C$_6$ cyclic group; C$_1$–C$_4$ alkyl and $C_1$–$C_4$ alkyl containing, or linked to the cyclic group through, an in-chain O atom, the aforesaid alkyl groups optionally being substituted by a substituent selected from halogen, amino, nitro, hydroxy and a $C_5$–$C_6$ cyclic group; and boroMpg-OH is a residue of an aminoboronic acid of the formula $H_2N$—$CH((CH_2)_3OMe)B(OH)_2$.

19. The salt of claim 12 which comprises a divalent metal salt of the peptide boronic acid.

20. A pharmaceutical formulation adapted for oral administration which comprises a salt of claim 1.

21. The salt of claim 1 wherein the organoboronic acid is of formula (III) below when included in a pharmaceutical formulation adapted for oral administration and comprising
a) a first species selected from a boronic acid of formula (III), or said boronic acid when in the form of boronate ions thereof, or equilibrium forms of said boronic acid and of said boronate ions, or combinations thereof:

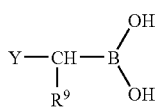
(III)

wherein
Y comprises a moiety which, together with the aminoboronic acid residue —NHCH($R^9$)—B(OH)$_2$, has affinity for the substrate binding site of thrombin; and
$R^9$ is a straight chain alkyl group interrupted by one or more ether linkages and in which the total number of oxygen and carbon atoms is 3, 4, 5 or 6 or $R^9$ is —(CH$_2$)$_m$—W where m is from 2, 3, 4 or 5 and W is —OH or halogen; and
(b) a second species selected from multivalent metal ions having a valency n,
wherein the formulation has an observed stoichiometry of first to second species essentially consistent with a notional stoichiometry of n:1.

22. A method of inhibiting thrombin comprising parenterally administering to a mammal suffering from thrombosis a therapeutically effective amount of the salt defined in claim 1.

23. A medicament adapted for oral administration and comprising a therapeutically effective amount of a salt of claim 1.

24. A medicament of claim 23 which is in solid dosage form.

25. A medicament of claim 24 wherein the boronic acid has a Ki for thrombin of about 100 nM or less.

26. The salt of claim 12, wherein:
aa$^1$ is selected from Phe, Dpa and wholly or partially hydrogenated analogues thereof;
aa$^2$ is a residue of an imino acid of formula (V);

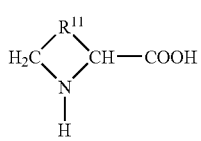
(V)

where $R^{11}$ is —CH$_2$—, —CH$_2$—CH$_2$—, —S—CH$_2$—, —S—C(CH$_3$)$_2$— or —CH$_2$—CH$_2$—CH$_2$—, and, when the formula (V) ring is 5- or 6-membered, the formula (V) ring is unsubstituted or is substituted at one or more —CH$_2$— groups by from 1 to 3 $C_1$–$C_3$ alkyl groups;
$R^9$ is a straight chain alkyl group interrupted by one or more ether linkages and in which the total number of oxygen and carbon atoms is from 3 to 6.

27. The salt of claim 26 wherein aa$^1$ is of (R)-configuration, aa$^2$ is of (S)-configuration, and chiral centre —NH—CH($R^9$)—B(OH)$_2$ is of (R)-configuration.

28. The salt of claim 27 wherein $R^9$ is alkoxyalkyl containing 4 carbon atoms, aa$^1$ is Phe or a wholly or partially hydrogenated analogue thereof and aa$^2$ is azetidine-2-carboxylic acid or proline.

29. The salt of claim 28 wherein $R^9$ is 3-methoxypropyl.

30. The salt of claim 27 wherein the multivalent metal is calcium, magnesium or zinc.

31. The salt of claim 28 which is a hemicalcium, hemimagnesium or hemizinc salt.

32. The salt of claim 29 which is a hemicalcium salt.

33. The salt of claim 18 wherein X is $R^6$—(CH$_2$)$_p$—O—C(O)—, where $R^6$ is 5 to 13-membered aromatic or heteroaromatic group and p is 0 or 1.

34. The salt of claim 1 wherein the boronic acid is of the formula:

Cbz-(R)-Phe-(S)-Pro-(R)-Mpg-B(OH)$_2$.

35. The salt of claim 34 wherein the multivalent metal is calcium, magnesium or zinc.

36. The salt of claim 34 which is a hemicalcium salt.

37. The salt of claim 4 wherein $R^9$ is 3-methoxypropyl and the carbon atom to which $R^9$ is bonded comprises a chiral centre of (R)-configuration.

38. The salt of claim 37 which consists essentially of a hemicalcium, hemimagnesium or hemizinc salt.

39. The salt of claim 37 which comprises a hemicalcium or hemimagnesium salt.

40. The salt of claim 34 which comprises a hemicalcium or hemimagnesium salt and which comprises anhydride species of the acid.

41. The salt of claim 1 which comprises the boronic acid in anhydride form.

42. The salt of claim 11 which comprises the boronic acid in the form of an anhydride.

43. The salt of claim 21 wherein the first species comprises the organoboronic acid in the form of an anhydride.

44. The salt of claim 36 which comprises the boronic acid in the form of an anhydride.

45. The pharmaceutical formulation of claim 20 wherein the formulation is in the form of a tablet or a capsule.

46. The pharmaceutical formulation of claim 45 wherein the tablet or capsule is enterically coated.

47. The pharmaceutical formulation of claim 45 wherein the tablet or capsule is not enterically coated.

48. The pharmaceutical formulation of claim 20 further comprising at least one further pharmaceutically active agent in addition to the salt of claim 1.

49. The pharmaceutical formulation of claim 48 wherein the further pharmaceutically active agent comprises a cardiovascular treatment agent.

50. A pharmaceutical formulation adapted for oral administration which comprises at least one salt of claim 11.

51. A pharmaceutical formulation adapted for oral administration which comprises at least one salt of claim 37.

52. The pharmaceutical formulation of claim 51 wherein the salt comprises the boronic acid in anhydride form.

53. The pharmaceutical formulation of claim 52 wherein said at least one salt consists essentially of a single said metal and a single said boronic acid, the metal being selected from calcium and magnesium.

54. The pharmaceutical formulation of claim 51 wherein the formulation is in the form of a tablet that is not enterically coated or a capsule that is not enterically coated.

55. A pharmaceutical formulation adapted for oral administration which comprises as an active agent a salt of claim 34.

56. The pharmaceutical formulation of claim 55 wherein the salt is selected from the hemicalcium and hemimagnesium salts of a boronic acid of the formula Cbz-(R)-Phe-(S)-Pro-(R)-boroMpg-OH;
wherein boroMpg-OH is a residue of an aminoboronic acid of the formula $H_2N-CH((CH_2)_3OMe)B(OH)_2$.

57. The pharmaceutical formulation of claim 56 wherein the active agent is the hemicalcium salt.

58. The pharmaceutical formulation of claim 57 wherein the salt comprises the boronic acid in anhydride form.

59. The pharmaceutical formulation of claim 57 which is in the form of an enterically coated tablet or capsule.

60. The pharmaceutical formulation of claim 57 which is in the form of a tablet or capsule which is not enterically coated.

61. A method of inhibiting thrombin comprising orally administering to a mammal suffering from thrombosis a therapeutically effective amount of the salt of claim 1.

62. A method of inhibiting thrombin comprising orally administering to a mammal suffering from thrombosis a therapeutically effective amount of the salt of claim 11.

63. A method of inhibiting thrombin comprising orally administering to a mammal suffering from thrombosis a therapeutically effective amount of the salt of claim 34.

64. A method of inhibiting thrombin comprising orally administering to a mammal suffering from thrombosis a therapeutically effective amount of the pharmaceutical formulation of claim 56.

65. A method of inhibiting thrombin comprising orally administering to a mammal suffering from thrombosis a therapeutically effective amount of the pharmaceutical formulation of claim 57.

66. A method of inhibiting thrombin comprising orally administering to a mammal suffering from thrombosis a therapeutically effective amount of the pharmaceutical formulation of claim 58.

67. A method of inhibiting thrombin comprising orally administering to a mammal suffering from thrombosis a therapeutically effective amount of the pharmaceutical formulation of claim 59.

68. A method of inhibiting thrombin comprising orally administering to a mammal suffering from thrombosis a therapeutically effective amount of the pharmaceutical formulation of claim 60.

69. The method of claim 64 wherein the salt is in solid dosage form.

70. The method of claim 65 wherein the salt is in solid dosage form and comprises the boronic acid in anhydride form.

71. The salt of claim 1 wherein the salt comprises anhydride species.

72. The salt of claim 11 wherein the salt comprises anhydride species.

73. The salt of claim 36 wherein the salt comprises anhydride species.

74. The salt of claim 1 which is substantially anhydride-free.

75. The salt of claim 11 which is substantially anhydride-free.

76. The salt of claim 36 which is substantially anhydride-free.

77. The pharmaceutical formulation of claim 20 wherein the salt is substantially anhydride-free.

78. The method of claim 64 wherein the salt is substantially anhydride-free.

79. The salt of claim 1 wherein the salt comprises an acid salt in which both B—OH groups of formula (I), when trigonally represented, are deprotonated.

80. The pharmaceutical formulation of claim 20 which comprises a mixture of multivalent metals.

81. The salt of claim 12 wherein the salt is of formula (VI)

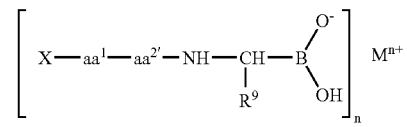

(VI)

where $M^{n+}$ is a divalent or trivalent metal cation, and n is 2 or 3, and the trigonally represented boronyl group —B(O)(OH) may comprise tetrahedral species.

82. The salt of claim 81 wherein $M^{n+}$ is $Ca^{2+}$.

83. A pharmaceutical formulation adapted for oral administration which comprises at least one salt of claim 81.

84. The pharmaceutical formulation of claim 83 which comprises a mixture of cations.

85. The salt of claim 1 wherein the organoboronic acid is of the formula Cbz-(R)-Phe-(S)-Pro-(R)-boroMpg-OH wherein boroMpg-OH is a residue of an aminoboronic acid of the formula $H_2N-CH((CH_2)_3OMe)B(OH)_2$, and is included in a pharmaceutical formulation adapted for oral administration, the salt comprising
a) a first species selected from (i) said boronic acid or (ii) said boronic acid when in the form of boronate ions thereof, or equilibrium forms of said boronic acid and of said boronate ions, or combinations thereof and
b) a second species selected from multivalent metal ions.

86. The salt of claim 85 wherein the pharmaceutical formulation further comprises one or more additional components selected from a) fillers or extenders; b) binders; c) humectants; d) disintegrating agents; e) solution retarding agents; f) absorption accelerators; g) wetting agents; h) absorbents; i) lubricants; and j) dissolution aids, or mixtures thereof.

87. The pharmaceutical formulation of claim 53 wherein the metal is calcium.

88. A composition of matter comprising the salt of claim 1 wherein the organoboronic acid is of the formula Cbz-(R)-Phe-(S)-Pro-(R)-boroMpg-OH wherein boroMpg-OH is a residue of an aminoboronic acid of the formula $H_2N-CH((CH_2)_3OMe)B(OH)_2$, the salt consisting essentially of:
a) a first species selected from (i) said boronic acid or (ii) said boronic acid when in the form of boronate ions thereof, or equilibrium forms of said boronic acid and of said boronate ions, or combinations thereof; and
b) a second species selected from calcium and magnesium ions, the composition of matter optionally further comprising one or more additional components selected from at least one pharmaceutically acceptable, orally suitable adjuvant, diluent or carrier; and at least one cardiovascular treatment agent.

89. The composition of claim 88 wherein the second species is calcium ions and the first species comprises boronate species having the characteristics of boronate species derived at least from a molecule of the boronic acid which has been singly deprotonated.

90. The composition of claim 88 wherein the second species is magnesium ions and the first species comprises boronate species having the characteristics of boronate species derived at least from a molecule of the boronic acid which has been singly deprotonated.

91. The composition of claim 89 which is adapted for oral administration.

92. A method for making a salt of claim 12, comprising:
combining in a solvent diethanolamine and an ester of a boronic acid as defined in claim 12;
allowing or causing a precipitate to form and recovering the precipitate;
converting the precipitated material into the free organoboronic acid by contacting the precipitated material with an aqueous acid or base; and
reacting the organoboronic acid with a base of a pharmaceutically acceptable multivalent metal to form to a salt as defined in claim 12.

* * * * *